(12) United States Patent
Doyle et al.

(10) Patent No.: US 6,458,816 B1
(45) Date of Patent: Oct. 1, 2002

(54) MODIFIED PRODRUG FORMS OF AP/AMP

(75) Inventors: Terrence W. Doyle, Killingworth; Srinivasa Karra, Hamden; Zujin Li, Orange; Xu Lin, Branford; John Mao, Guilford, all of CT (US); Qi Qiao, Nutley, NJ (US); Yang Xu, Cheshire, CT (US)

(73) Assignee: Vion Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 09/977,659

(22) Filed: Oct. 15, 2001

Related U.S. Application Data

(60) Provisional application No. 60/240,529, filed on Oct. 13, 2000.

(51) Int. Cl.⁷ ................. C07D 213/02; A61K 31/44
(52) U.S. Cl. ................. 514/353; 546/305; 546/306
(58) Field of Search ................. 546/305, 306; 514/353

(56) References Cited

U.S. PATENT DOCUMENTS 5,767,134 A * 6/1998 Li et al. ................. 514/353

FOREIGN PATENT DOCUMENTS

WO  WO98/51669  11/1998

\* cited by examiner

Primary Examiner—Zinna Northington Davis
(74) Attorney, Agent, or Firm—Henry D. Coleman; Coleman, Sudol, Sapone, P.C.

(57) ABSTRACT

The present invention relates to compounds according to the structure:

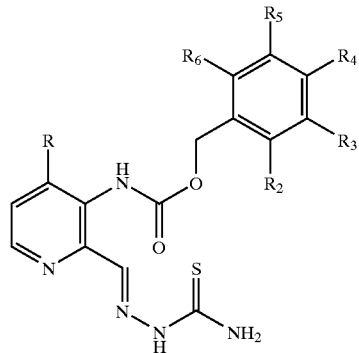

Where
R is H or $CH_3$;
$R_2$ is phosphate which can be free acid or salt;
$R_3$ is H, F, Cl, Br, I, $OCH_3$, $OCF_3$, $CF_3$ or a $C_1$–$C_3$ alkyl group;
$R_4$ is H, F, Cl, Br, I, $OCH_3$, $OCF_3$ or $CF_3$; and
$R_5$ and $R_6$ are each independently H, F, Cl, Br, I, $OCH_3$, $OCF_3$ or $CF_3$, with the proviso that when any two of $R_3$, $R_4$, $R_5$ or $R_6$ are other than H, the other two of $R_3$, $R_4$, $R_5$ or $R_6$ are H which may be used to treat neoplasia, including cancer.

59 Claims, 28 Drawing Sheets

FIGURE 3 (CONT'D)

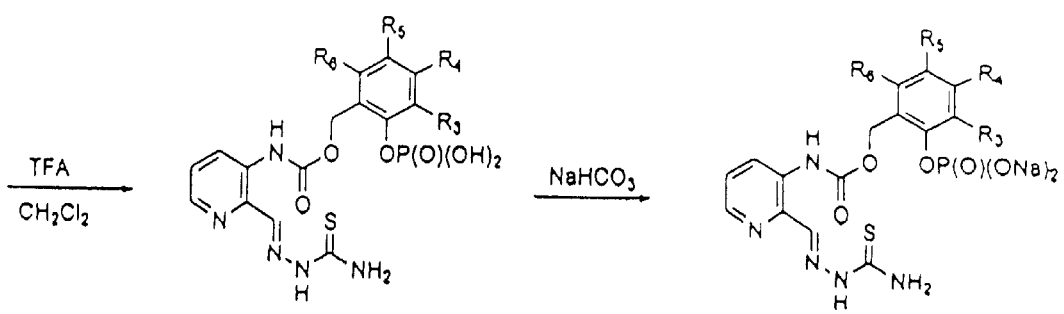

7  $R_3 = R_4 = R_6 = H, R_5 = F$
8  $R_3 = R_4 = R_6 = H, R_5 = NO_2$
9  $R_3 = R_4 = R_6 = H, R_5 = OCH_3$
10 $R_3 = R_4 = R_6 = H, R_6 = OCF_3$
11 $R_3 = R_4 = R_6 = H, R_6 = CF_3$
12 $R_4 = R_5 = H, R_3 = R_6 = Cl$
13 $R_3 = R_6 = H, R_4 = R_5 = Cl$
14 $R_3 = R_4 = H, R_5 = R_6 = Cl$
15 $R_4 = R_5 = R_6 = H, R_3 = CH_3$
16 $R_3 = R_5 = R_6 = H, R_4 = Cl$
17 $R_3 = R_5 = R_6 = H, R_4 = OCH_3$

30a $R_3 = R_4 = R_6 = H, R_5 = F$ (59%)
30b $R_3 = R_4 = R_6 = H, R_5 = NO_2$ (73%)
30c $R_3 = R_4 = R_6 = H, R_5 = OCH_3$ (43%)
30d $R_3 = R_4 = R_6 = H, R_6 = OCF_3$ (31%)
30e $R_3 = R_4 = R_6 = H, R_6 = CF_3$ (45%)
30f $R_4 = R_5 = H, R_3 = R_5 = Cl$ (24%)
30g $R_3 = R_5 = H, R_4 = R_6 = Cl$ (23%)
30h $R_3 = R_4 = H, R_5 = R_6 = Cl$ (64%)
30i $R_4 = R_5 = R_6 = H, R_3 = CH_3$ (57%)
30j $R_3 = R_5 = R_6 = H, R_4 = Cl$ (48%)
30k $R_3 = R_5 = R_6 = H, R_4 = OCH_3$ (64%)

Figure 4. Triapine Serum Peak Concentration (Cmax) vs Dose in Dogs

Figure 5. Triapine Serum AUC vs Dose in Dogs

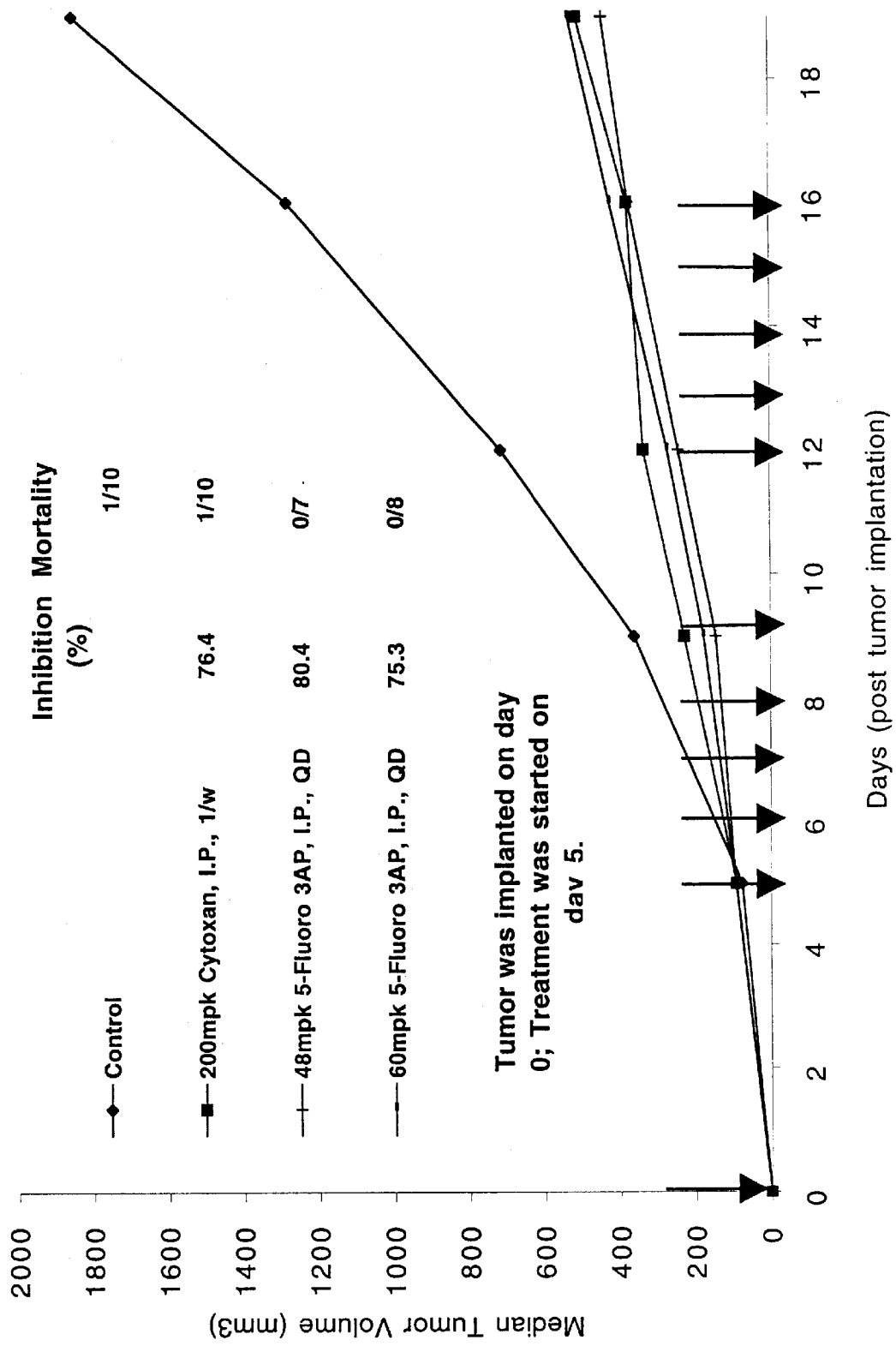

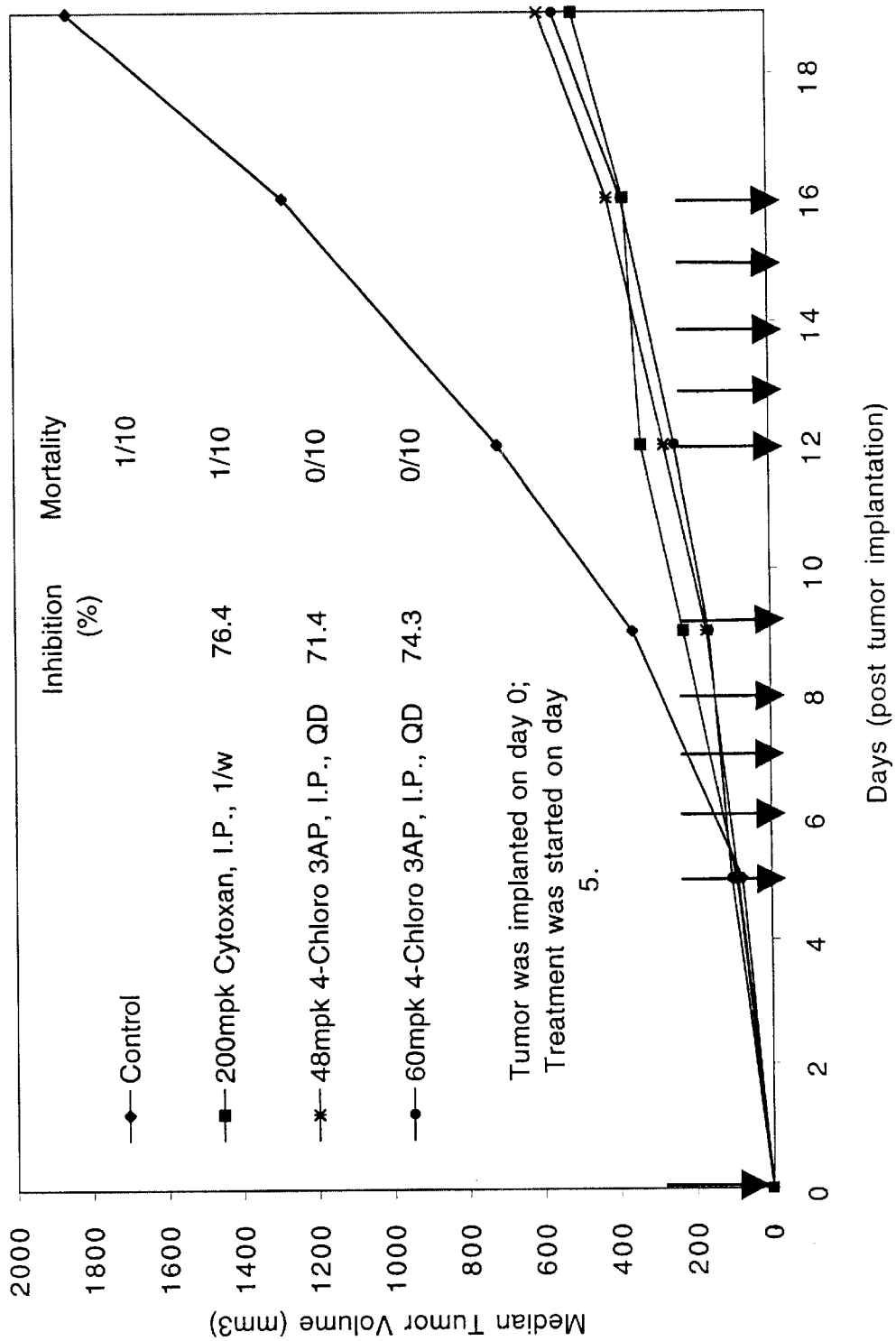

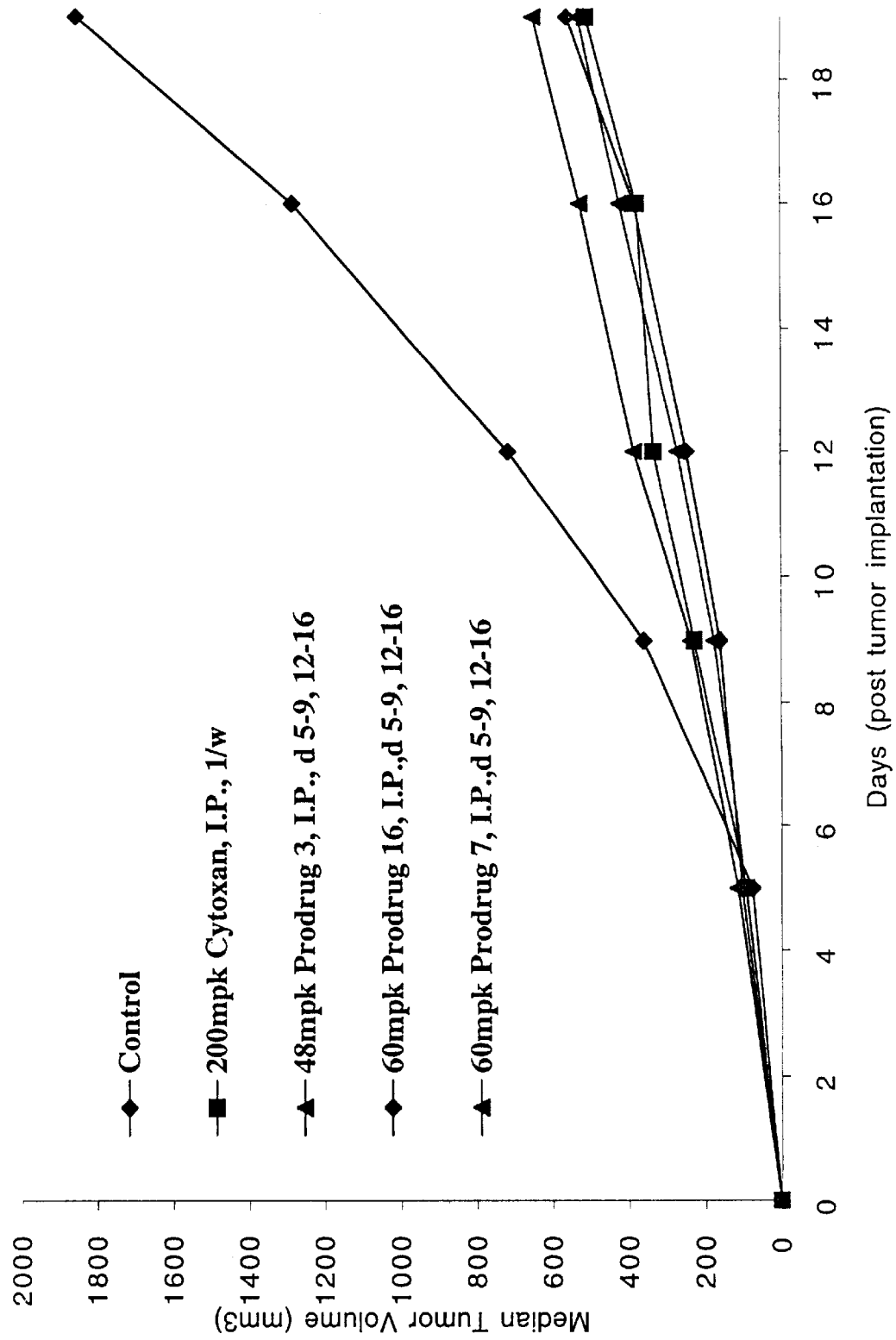

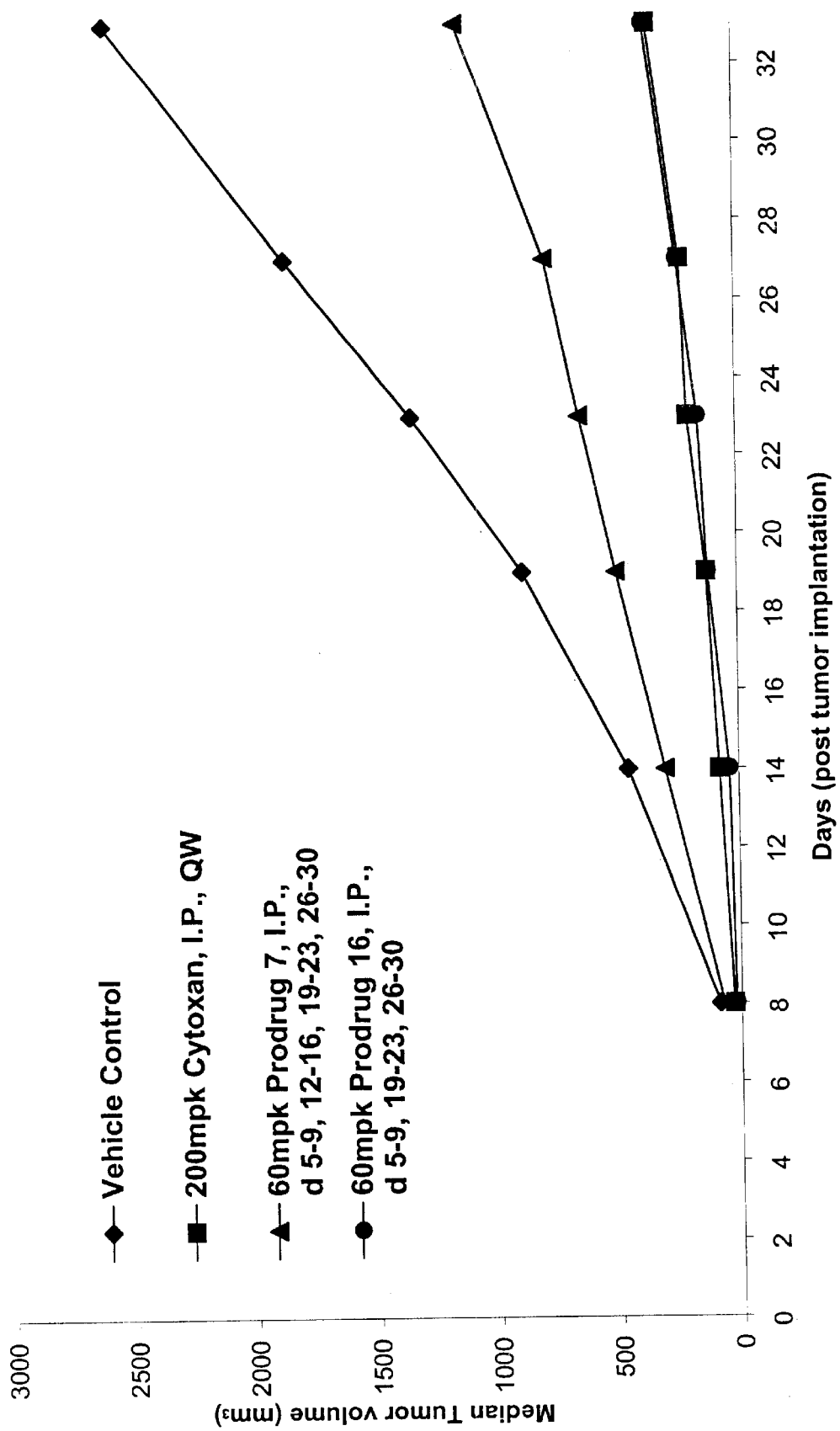
Figure 7D. Efficacy of Prodrugs 12 and 21 on HTB177 Human Lung Carcinoma

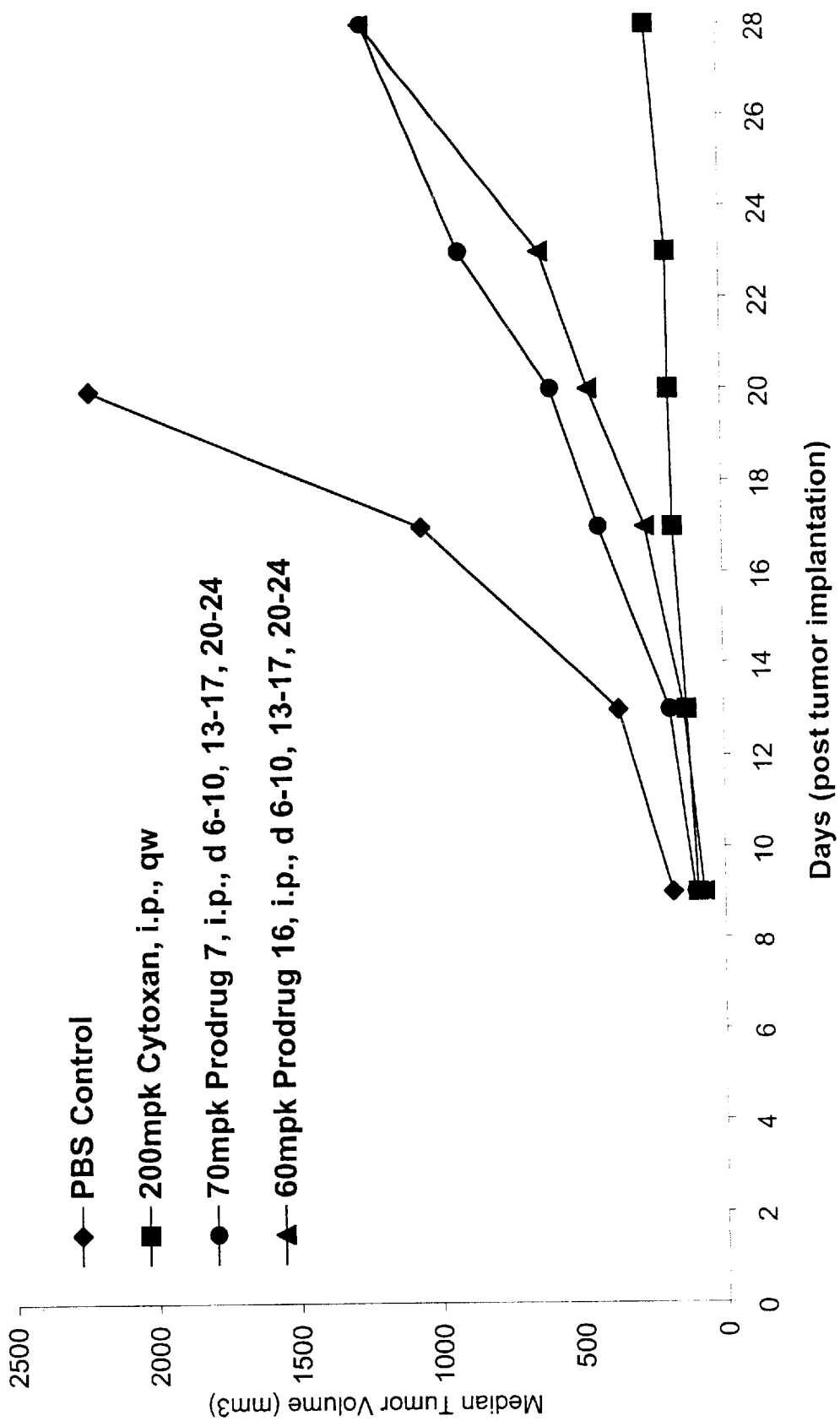
Figure 7E. Efficacy of Prodrugs 12 and 21 on B16-F10 Melanoma

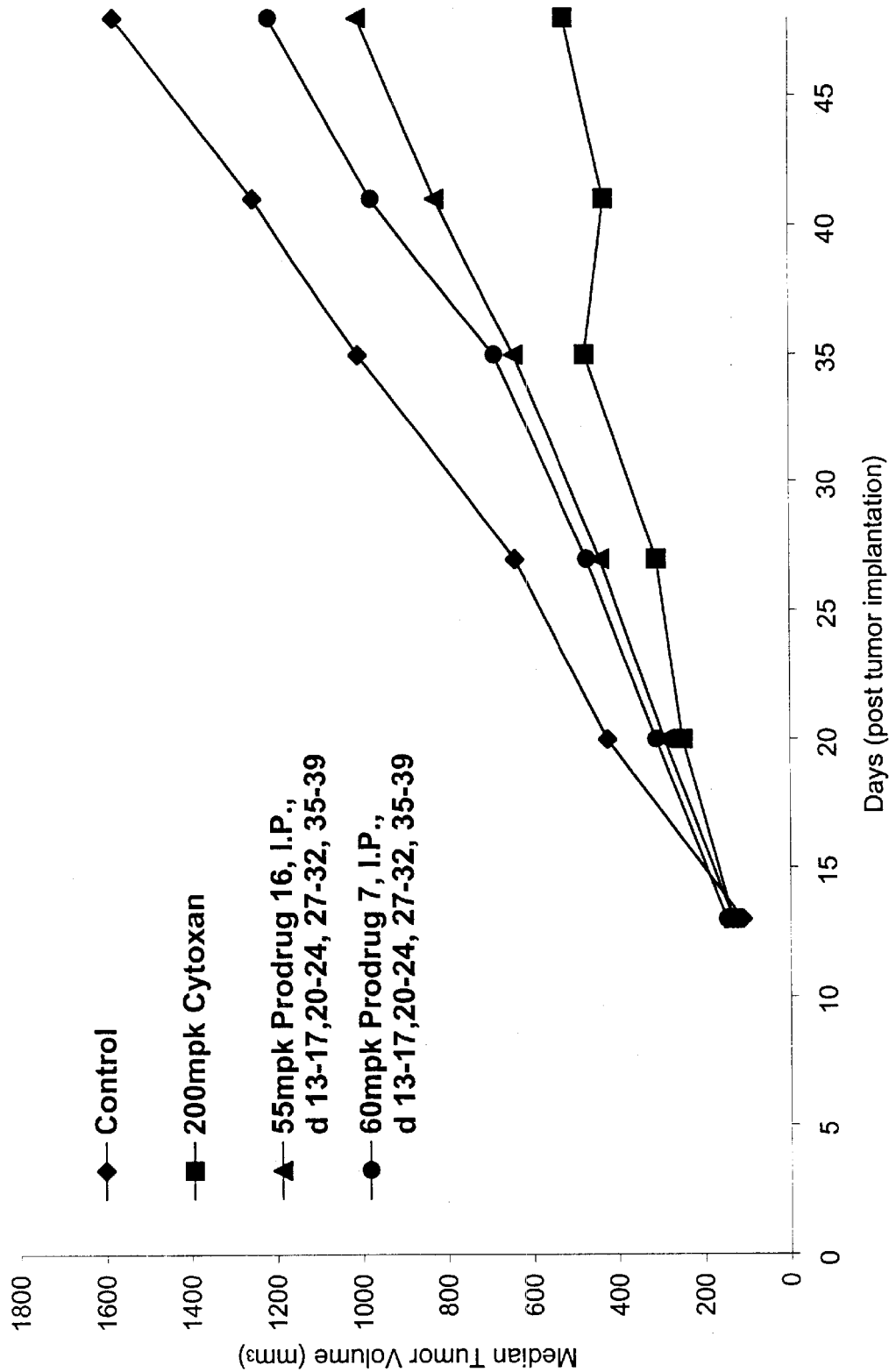

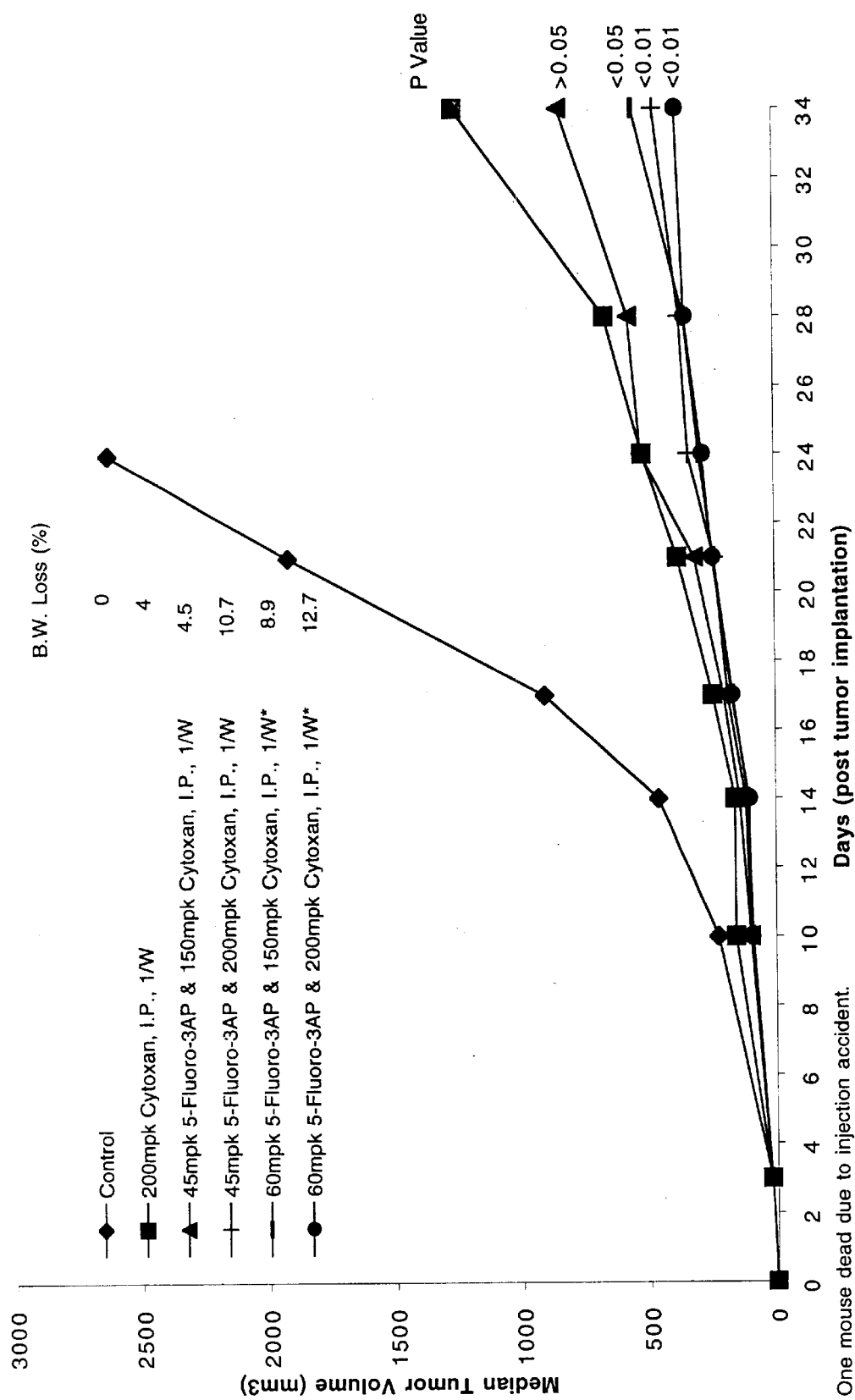
Figure 8A. Efficacy of 5-Fluoro-3AP Based Combination Chemotherapy on M109 Lung Carcinoma in Balb/c Mice
* One mouse dead due to injection accident.

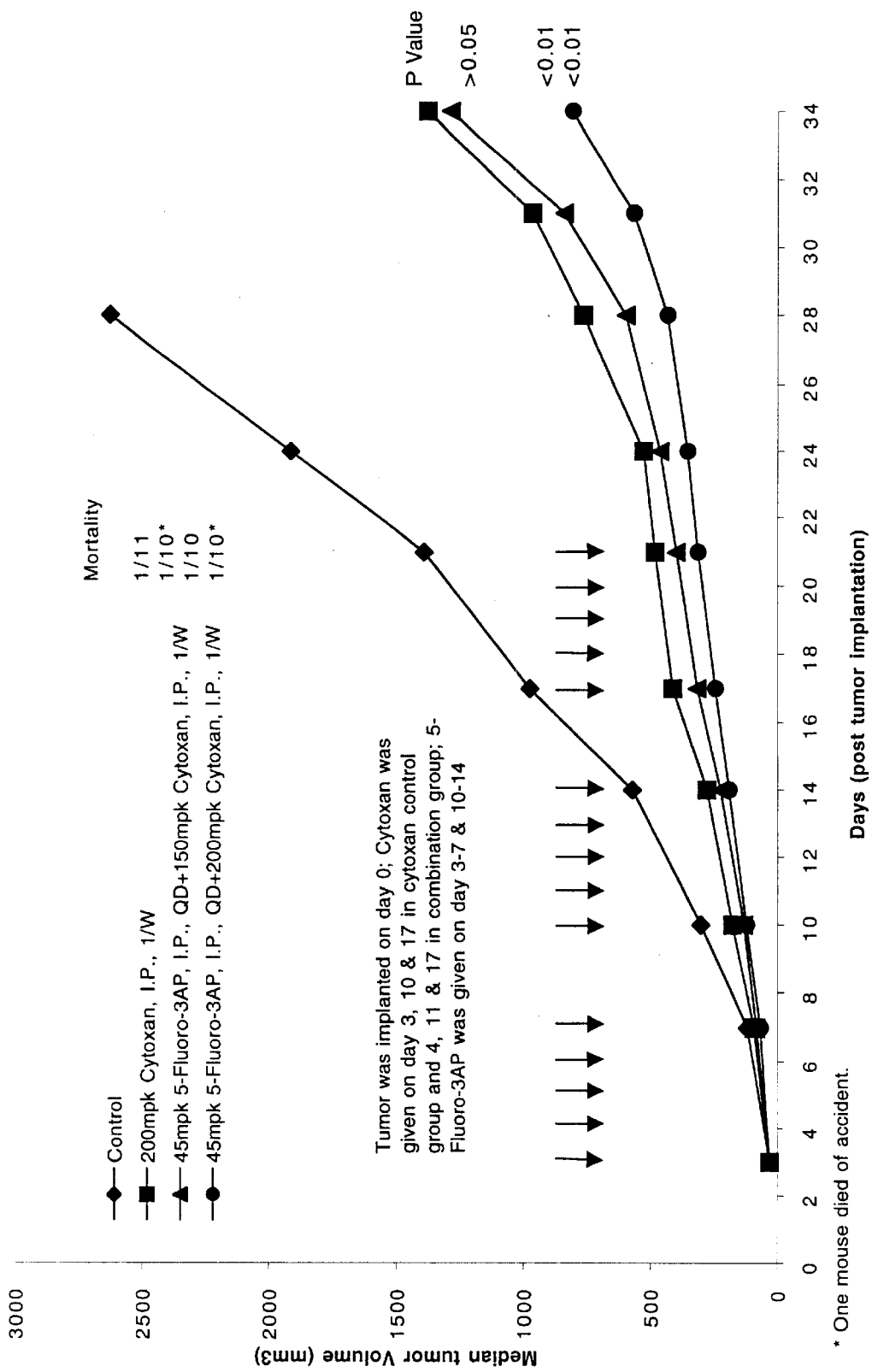

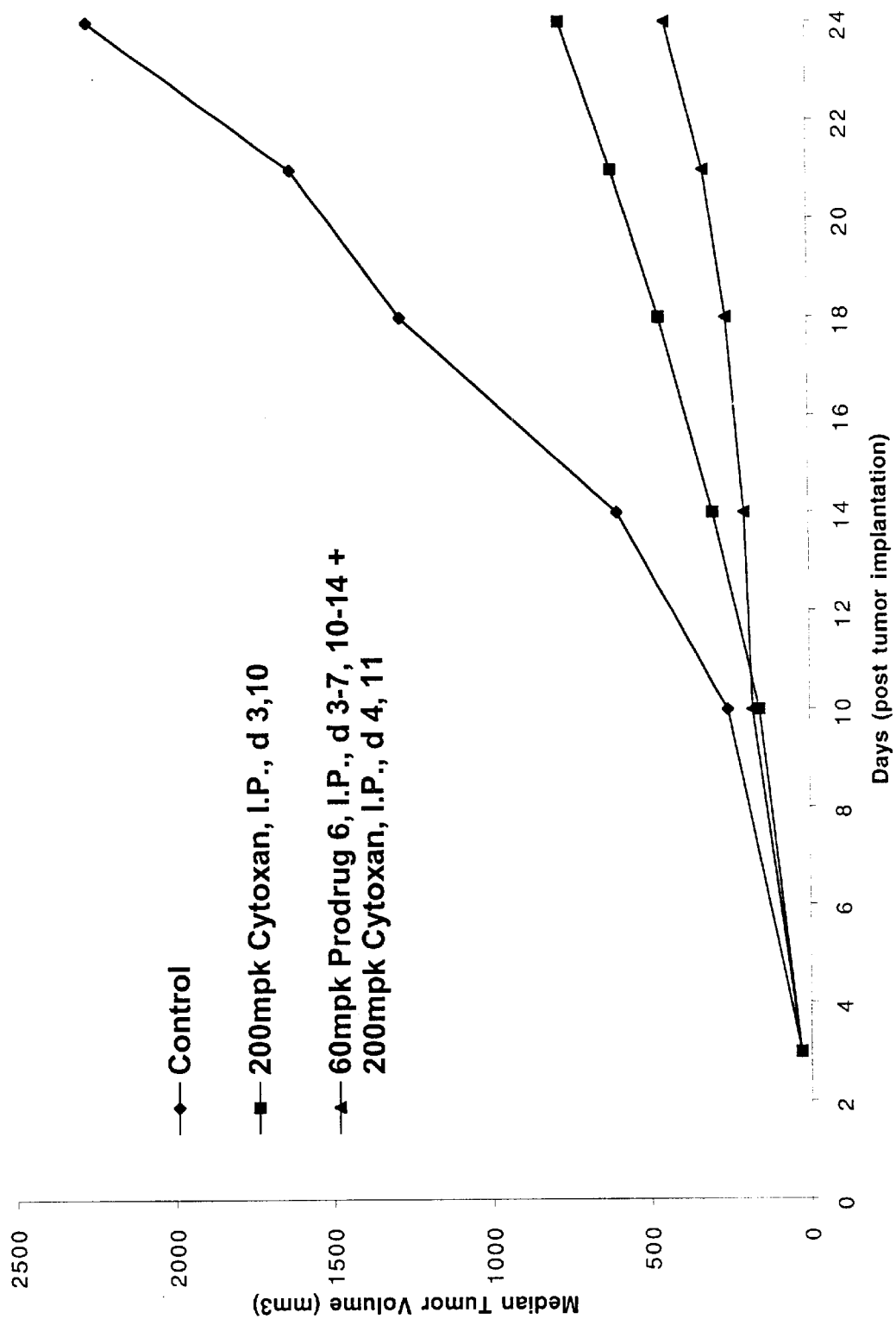

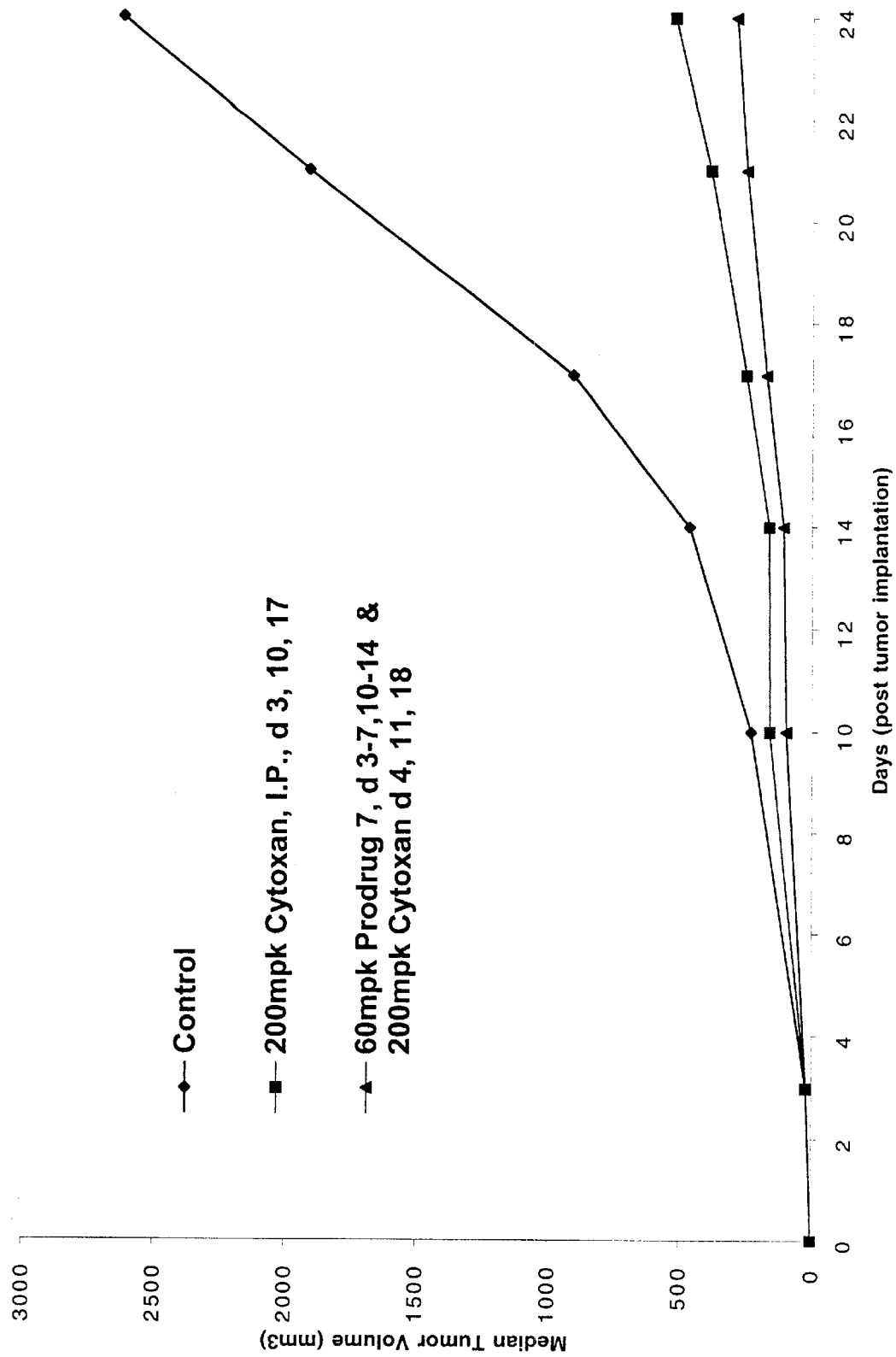

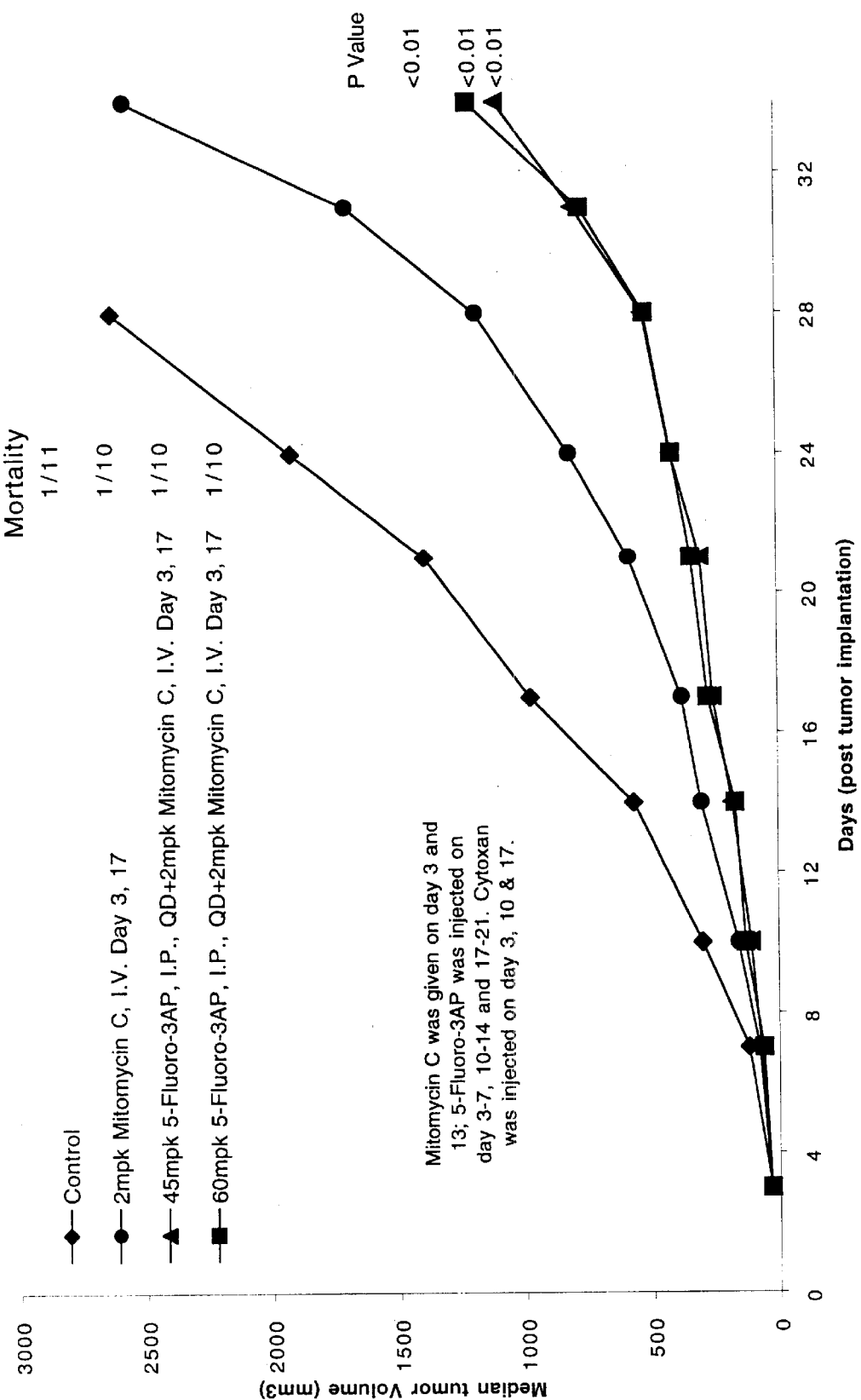
Figure 9A. Efficacy of 5-Fluoro-3AP/mitomycin C Combination Chemotherapy on M109 Lung Carcinoma in Balb/c Mice (Day 34)

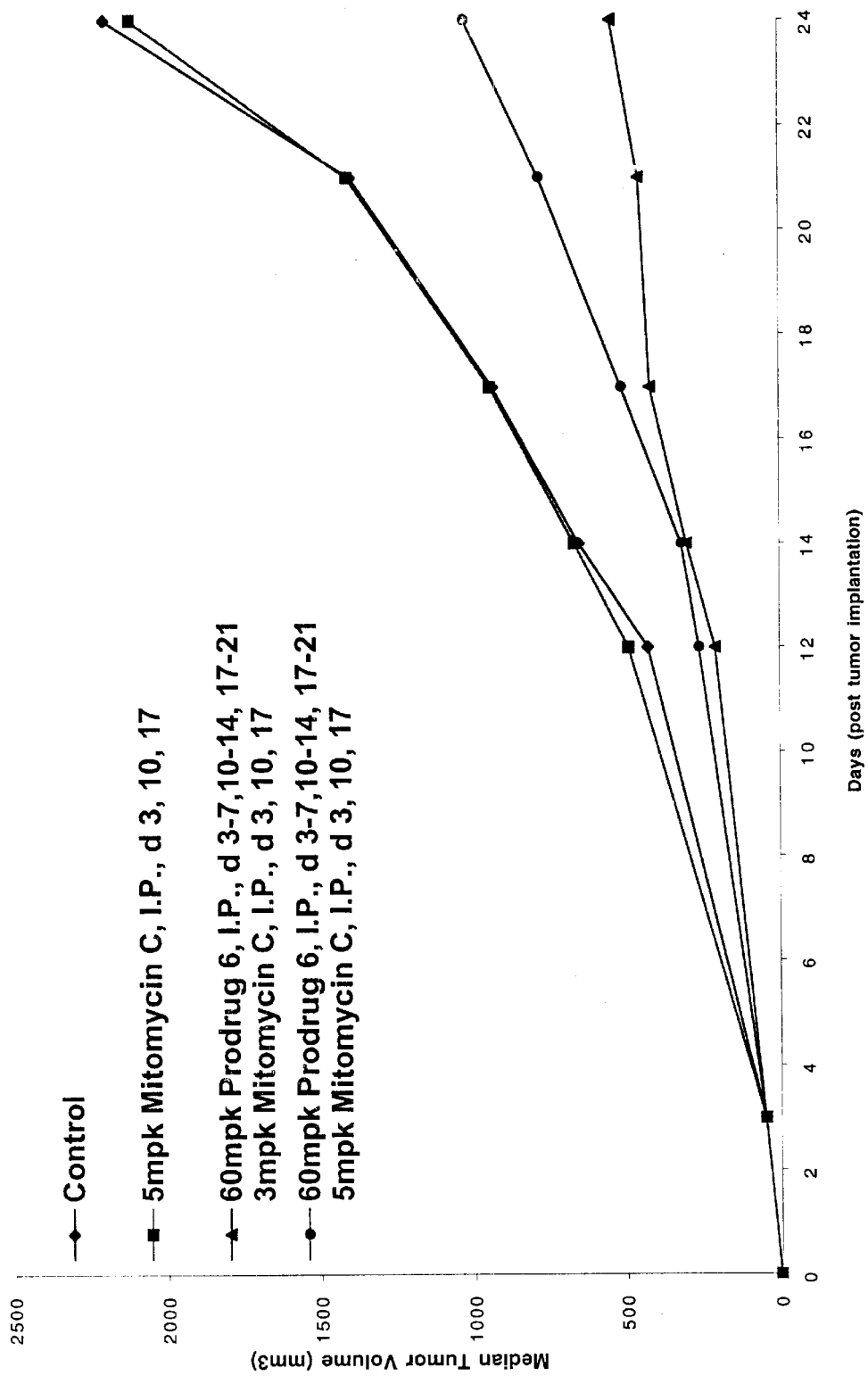

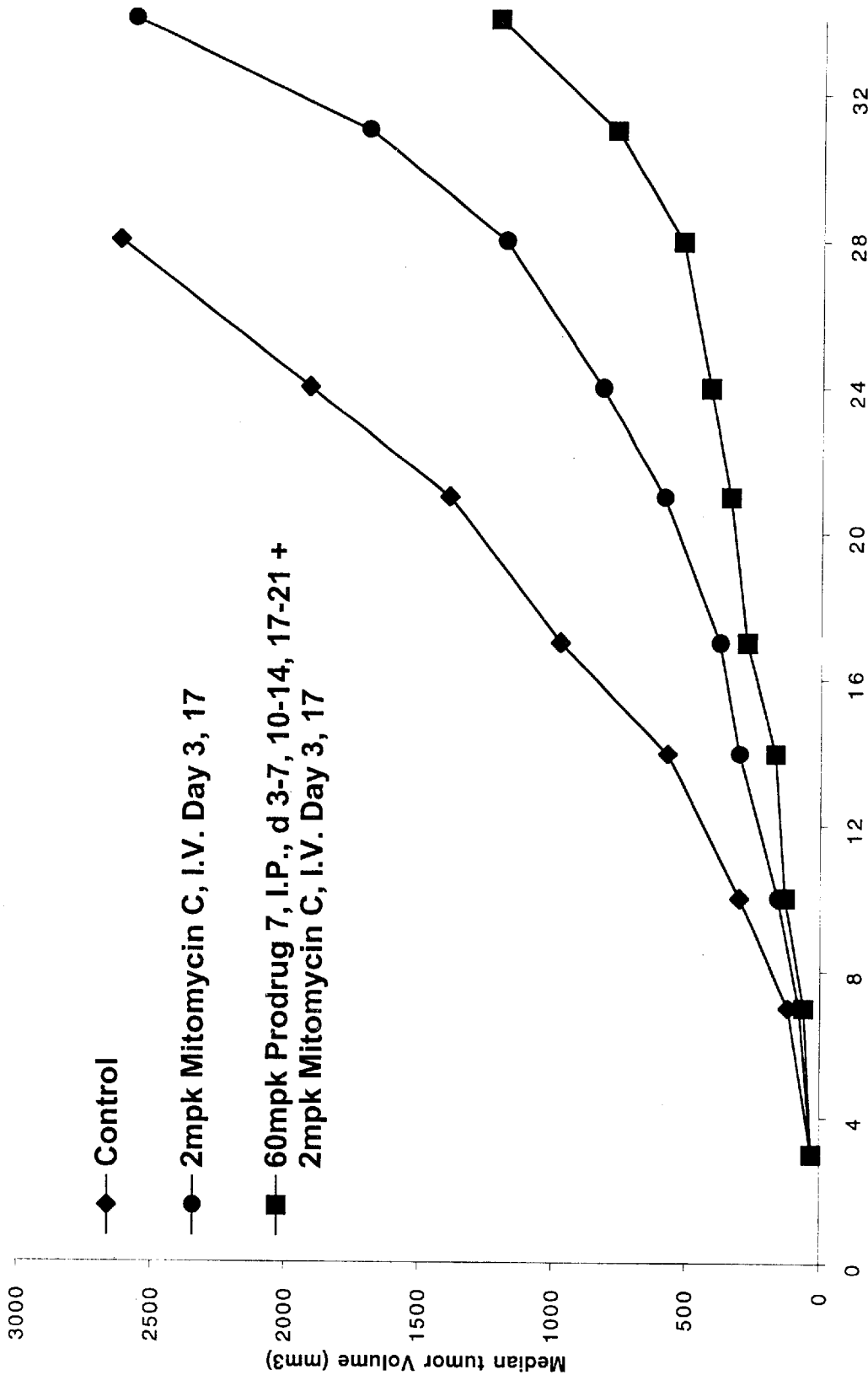

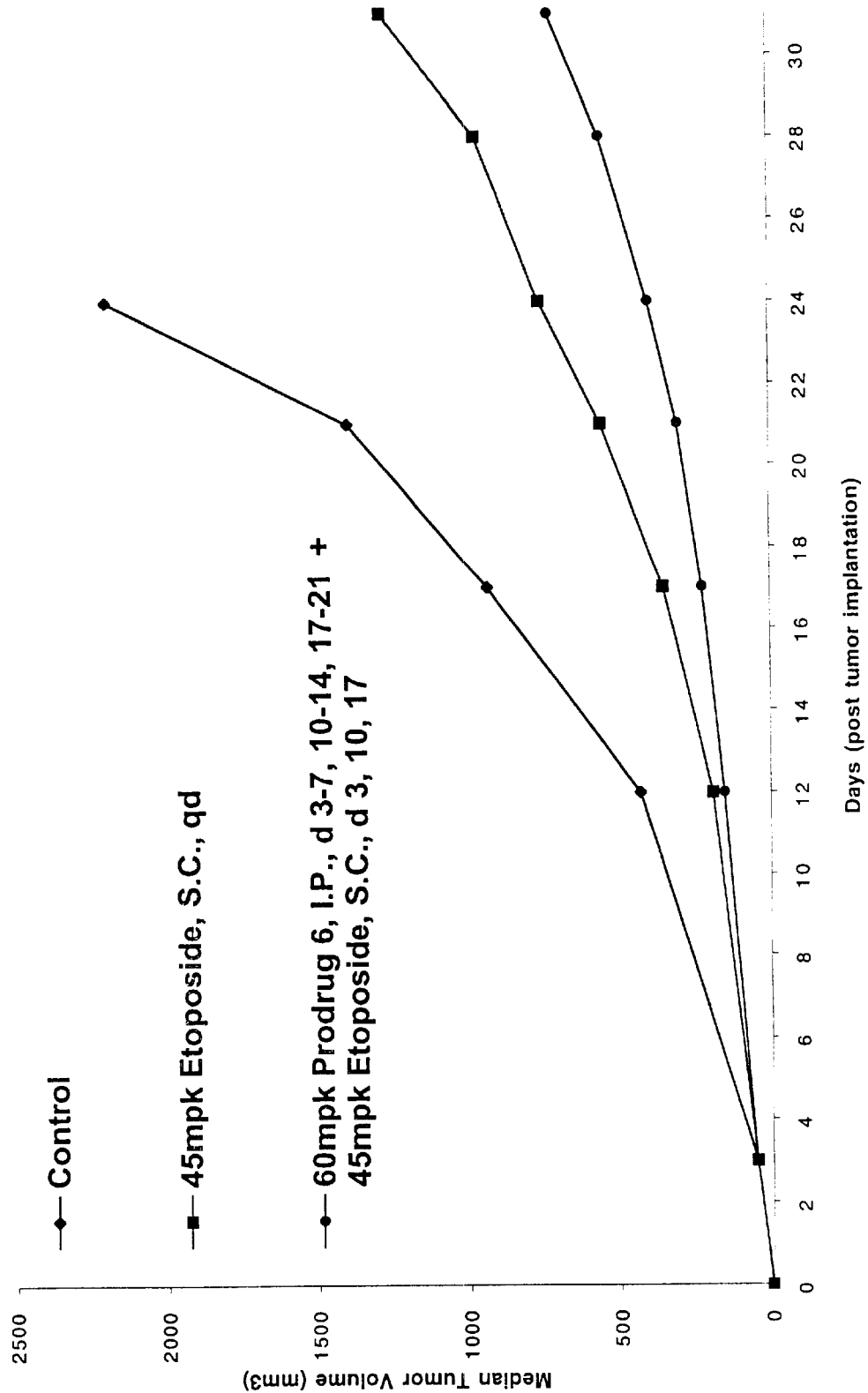

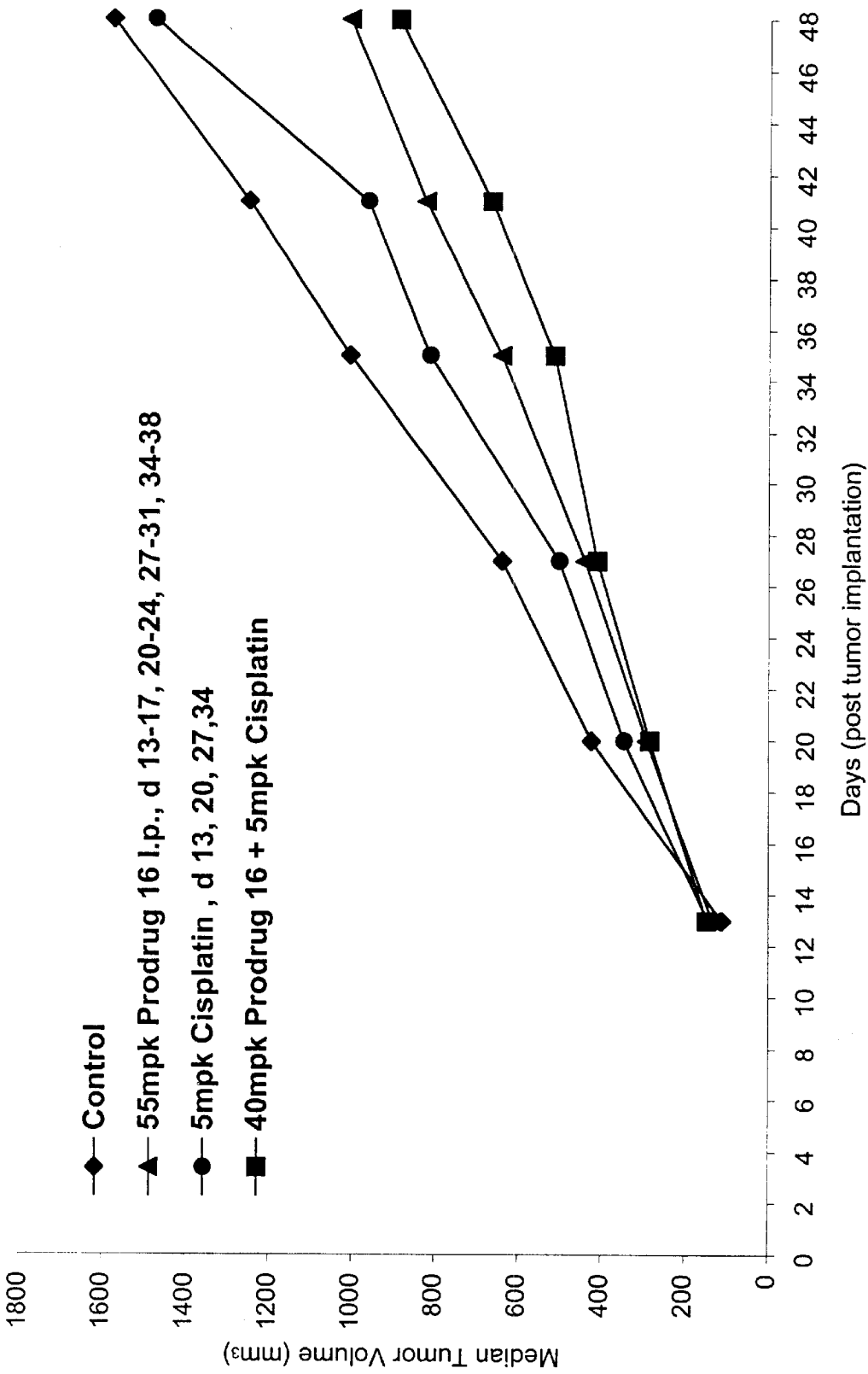
Exp.10A. Efficacy of Prodrug 16/Cisplatin Combination on DLD1 Human Colon Carcinoma

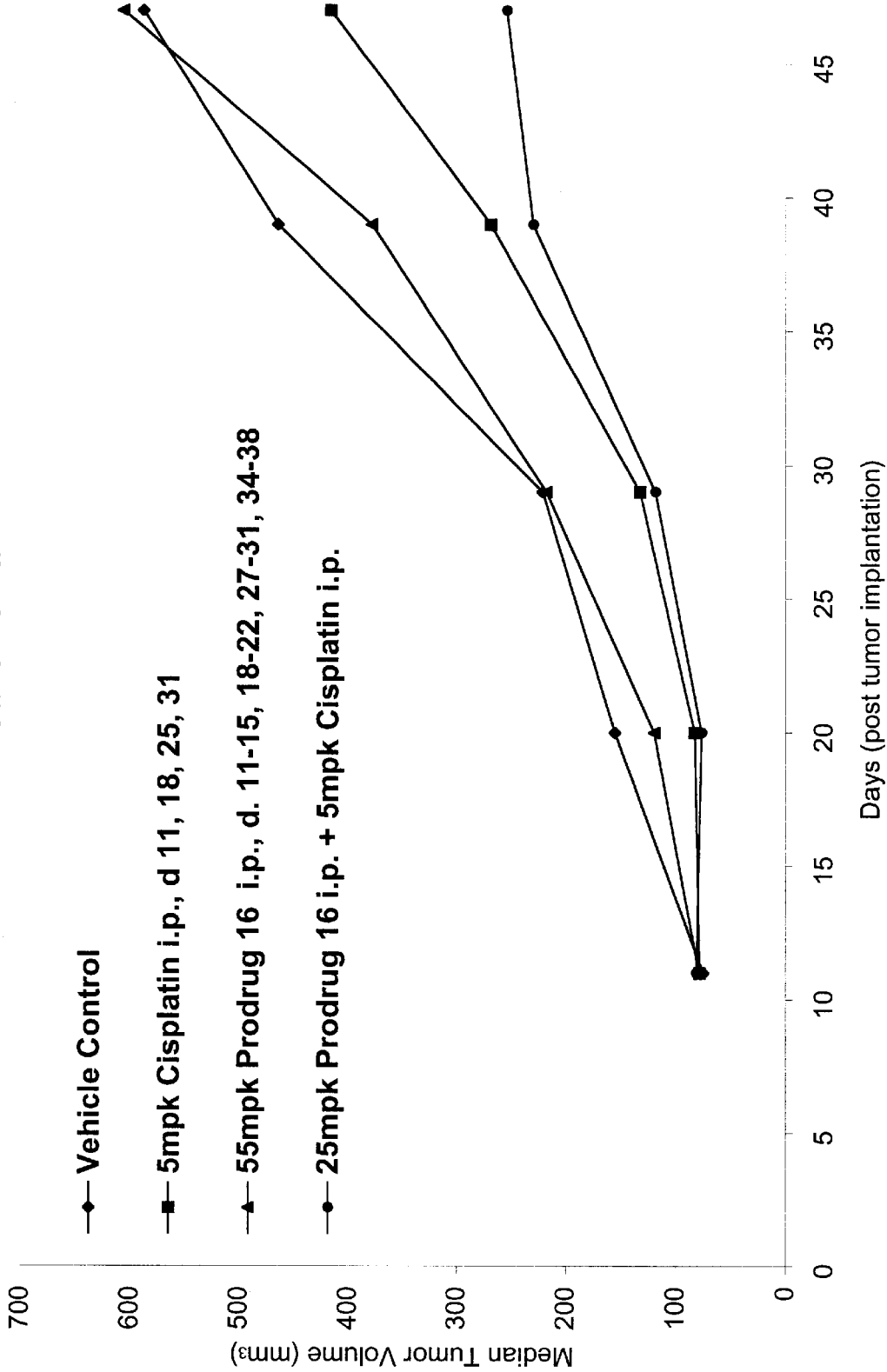

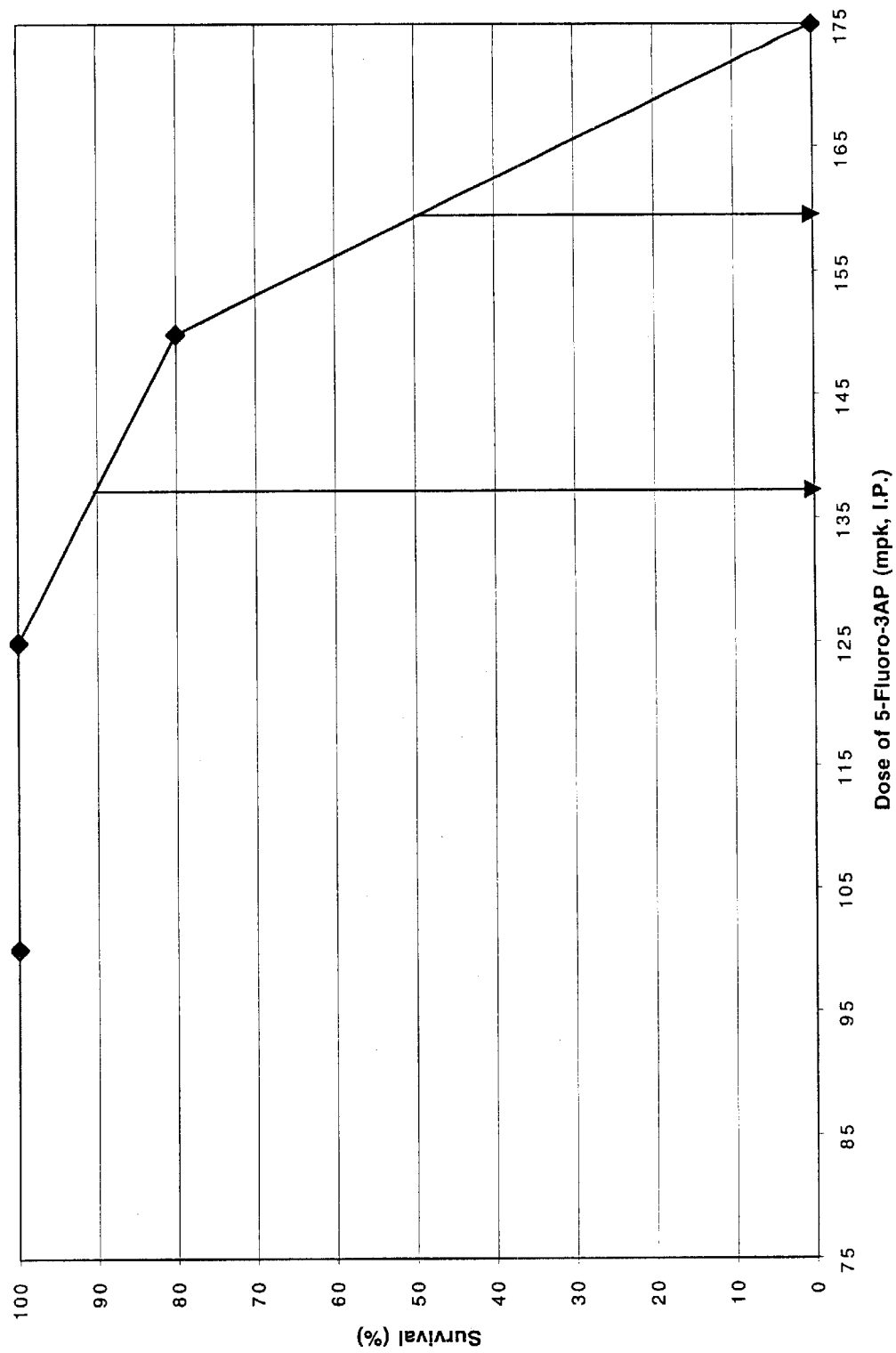

MODIFIED PRODRUG FORMS OF AP/AMP

RELATED APPLICATIONS

This application claims the benefit of priority from U.S. provisional application serial No. 60/240,529 of same title filed Oct. 13, 2000.

BACKGROUND OF THE INVENTION

The reductive conversion of ribonucleotides to deoxyribonucleotides by the enzyme Ribonuclcotide Reductase (RR) is a crucial, rate-controlling step in the pathway leading to the biosynthesis of DNA. (Cory, J. G. In "Inhibitors of Ribonucleotide Diphosphate Reductase Activity", *International Encyclopedia of Pharmacology and Therapeutics,* Cory, J. G.; Cory, A. H., Eds.; Pergamon Press: New York, (1989); Section 128, pp 1–16). Since deoxyribonucleotides are present in extremely low levels in mammalian cells, an excellent correlation exists between tumor growth rate and specific activity of ribonucleotide reductase (Elford, et al., *J. Biol. Chem.* (1970), 245, 5228). Mammalian Ribonucleotide Reductase is composed of two dissimilar proteins, often referred to as R1, which binds the ribonucleotide substrate, and R2, which contains non-heme iron and a free tyrosyl radical (Reichard, P.; Ehrenberg, A. *Science,* (1983), 221, 514). Both R1 and R2 contribute to the activity of the enzyme.

Currently, there are two broad classes of RR inhibitors. The first class includes nucleoside analogs whose mechanism of action involves binding to the R1 subunit of the enzyme; several of these are in clinical development. Among these, 2',2'-difluoro-2'-deoxycytidine (Gemcitabine, Trade name: Gemzar, Eli Lilly) was recently approved by the FDA for the treatment of pancreatic cancer (Baker, et al., *J. Med. Chem.* (1991), 34, 1879), and 2'-fluoromethylene-2'-deoxycytidine is being evaluated in clinical trials for the treatment of various tumors (McCarthy, J. R. and Sunkara, P. S. In *Design, Synthesis, and Antitumor Activity of An Inhibitor of Ribonucleotide Reductase,* Weiner, D. B.; Williams, W. V. Eds.; CRC Press:Boca Raton, (1994), 68 1364). The second class of RR inhibitors includes N-hydroxyurea (Reichard & Ehrenberg, *Science,* (1983), 221, 514 and Wright, et al., *Cell Biol.* (1990), 68, 1364) and HCTs [N-Heterocyclic Carboxaldehyde Thiosemicarbazones], which act by destroying the free radical of the R2 subunit. HCTs have been demonstrated to be the most potent inhibitors of ribonucleotide reductase, being 80–5000 fold more effective than N-hydroxyurea in vitro (See, Liu, et al., *J. Med. Chem.* (1992), 35, 3672 and *J. Med. Chem.* (1995), 38, 4234).

It is also broadly accepted that HCTs exert their enzyme inhibitory effect through their high binding affinity for iron on the R2 subunit, since iron is an essential element at the active site of ribonucleotide reductase. Several years ago, a phase 1 clinical evaluation of the lead compound in this series, 5-HP ( DeConti, et al., *Cancer Res.* (1972), 32, 1455 and Moore, et al., *Cancer Res.* (1971), 31, 235) demonstrated that, while the compound gave good activity in animal models it was inactive in patients with solid tumors presumably due to its rapid metabolism in humans. Modification of 5-HP through the introduction of steric hindrance and replacement of the hydroxy group with an amino moiety has resulted in a series of 3-amino-bearing compounds (e.g., 1A (3-AP) and 1B (3-AMP) (See Below)). Among these agents, 3-AP possesses excellent antitumor activity (Liu, et al., *J. Med. Chem.* (1992), 35, 3672) and drastically reduced clearance rates. It is currently in Phase 1 clinical trials. A single dose clinical trial was halted once the drug reached a pharmacokinetic endpoint without displaying any drug related toxicities. Additional Phase 1 studies of extended dosing schedules (daily times 5 and 96 hour continuous infusion) are in progress.

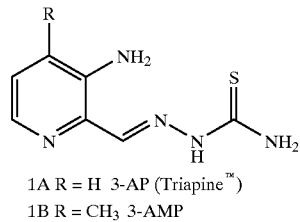

1A R = H 3-AP (Triapine™)
1B R = CH₃ 3-AMP

Despite the in vivo activity displayed by 3-AP, the therapeutic potential of this compound may be limited by its poor water-solubility. Therefore, to improve its water solubility and therapeutic index, the synthesis of two phosphate-bearing water-soluble prodrugs 2 (para 3-AP prodrug) and 3 (ortho 3-AP prodrug) was developed. The phosphate-bearing prodrugs were designed to give good water-solubility at neutral pH and increased bioavailability.

Preliminary in vitro evaluation of the 3-AP prodrugs showed that they were rapidly converted to 3-AP by alkaline phosphatase enzyme. In contrast the in vivo PK studies in Beagle dogs showed that 3-AP released from ortho phosphate-bearing prodrug 3 with a half-life of 14.2h, whereas para prodrug 2 has a half-life of 1.5h. Prodrugs 2 and 3 were also evaluated in the M-109 solid tumorbearing mice in vivo against 3-AP and cytoxan. The results from these experiments showed that the ortho prodrug 3 has better efficacy with reduced toxicity than the parent 3-AP and has comparable activity to that of cytoxan. With the aim to further improve the biological and pharmaceutical profiles and to maximize the therapeutic utility of the 3-AP prodrugs, a series of ortho phosphate-bearing prodrugs were

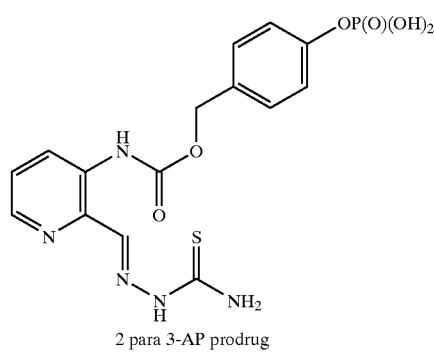

2 para 3-AP prodrug

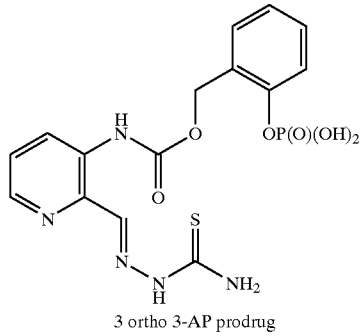

3 ortho 3-AP prodrug

OBJECTS OF THE INVENTION

In one aspect of the invention, an object of the present invention is to provide compounds, pharmaceutical compositions and methods for the treatment of neoplasia, including cancer, in patients.

In another aspect of the invention, an object of the present invention is to provide methods of treating neoplasia utilizing compositions which exhibit favorable and enhanced characteristics of activity, pharmacokinetics, bioavailability and reduced toxicity.

It is yet another object of the invention to provide compositions and methods for the treatment of cancers which are resistant to treatment with traditional chemotherapeutic agents.

One or more of these and/or other objects of the invention may be readily gleaned from the description of the invention which follows.

BRIEF DESCRIPTION OF THE INVENTION

The present invention relates to compounds according to the structure:

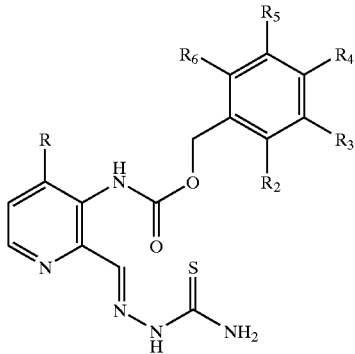

Where
R is H or $CH_3$;
$R_2$ is phosphate which can be the free acid or salt;
$R_3$ is H, F, Cl, Br, I, $OCH_3$, $OCF_3$, $CF_3$ or a $C_1$–$C_3$ alkyl group;
$R_4$ is H, F, Cl, Br, I, $OCH_3$, $OCF_3$,$CF_3$, $NO_2$, CN, $SO_2CF_3$, $COOCH_3$, $SF_5$, $SO_2CH_3$, $COCH_3$, $NH_2$, $N(CH_3)_2$, $SCH_3$, OH; and
$R_5$ and $R_6$ are each independently H, F, Cl, Br, I, $OCH_3$, $OCF_3$, $CF_3$, $NO_2$, CN, $SO_2CF_3$, $COOCH_3$, $SF_5$, $SO_2CH_3$, $COCH_3$, $NH_2$, $N(CH_3)_2$, $SCH_3$ or OH, with the proviso that when any two of $R_3$, $R_4$, $R_5$ or $R_6$ are other than H, the other two of $R_3$, $R_4$, $R_5$ or $R_6$ are H.

In particularly preferred aspects of compounds according to the present invention, $R_4$ is Cl, F or Br (preferably, Cl) when $R_3$, $R_5$ and $R_6$ are H. In other preferred aspects according to the present invention, $R_5$ is F, Cl, $OCH_3$ or $OCF_3$ (preferably F) when $R_3$, $R_4$ and $R_6$ are H. Still in other preferred aspects according to the present invention when two of $R_3$, $R_4$, $R_5$ or $R_6$ are selected from F, Cl, Br or I, (preferably, both substituents are the same and more preferably, both substituents are Cl), the other two of $R_3$, $R_4$, $R_5$ or $R_6$ are H. In still other preferred aspects of the present invention, when $R_4$ and $R_5$ or $R_5$ and $R_6$ are both F or Cl (preferably, both are Cl), then the other of $R_3$ and $R_6$ or $R_3$ and $R_4$ are both H. Compounds according to the present invention and especially the preferred compositions according to the present invention, as set forth above, are extremely effective compounds for the treatment of neoplasia, including cancer, and exhibit at least one or more of significantly enhanced anti-neoplasia activity, enhanced higher maximum tolerated doses (MTD) with reduced toxicity and prolonged half-life consistent with favorable pharmacokinetics compared to para or ortho 3-AP prodrugs 2 and 3. This represents an unexpected result. Thus, preferred compounds according to the present invention may be used at much higher doses, to greater effect against neoplasia, including cancer and with enhanced half-life in the blood stream and reduced toxicity.

Compounds according to the present invention may be used in pharmaceutical compositions having biological/pharmacological activity for the treatment of, for example, neoplasia, including cancer, as well as a number of other conditions and/or disease states, as intermediates in the synthesis of compounds exhibiting biological activity as well as standards for determining the biological activity of the present compounds as well as other biologically active compounds. In some applications, the present compounds may be used for treating microbial infections, especially including viral infections. These compositions comprise an effective amount of any one or more of the compounds disclosed hereinabove, optionally in combination with a pharmaceutically acceptable additive, carrier or excipient.

A further aspect of the present invention relates to the treatment of neoplasia, including cancer, comprising administering to a patient in need thereof an effective amount of a compound as described hereinabove, optionally in combination with a pharmaceutically acceptable additive, carrier or excipient. The present invention also relates to methods for inhibiting the growth of neoplasia, including a malignant tumor or cancer comprising exposing the neoplasia to an inhibitory or therapeutically effective amount or concentration of at least one of the disclosed compounds. This method may be used therapeutically, in the treatment of neoplasia, including cancer or in comparison tests such as assays for determining the activities of related analogs as well as for determining the susceptibility of a patient's cancer to one or more of the compounds according to the present invention. Primary utility resides in the treatment of neoplasia, including cancer, especially including lung cancer, breast cancer and prostate cancer, among others.

BRIEF DESCRIPTION OF THE FIGURES

FIGS. 4–15 are representations of experimental results which are presented in the present application related to the efficacy, pharmacokinetics, bioavailability, combination chemotherapy, and toxicity of certain preferred embodiments according to the present invention.

DETAILED DESCRIPTION OF THE INVENTION

Figure 1:
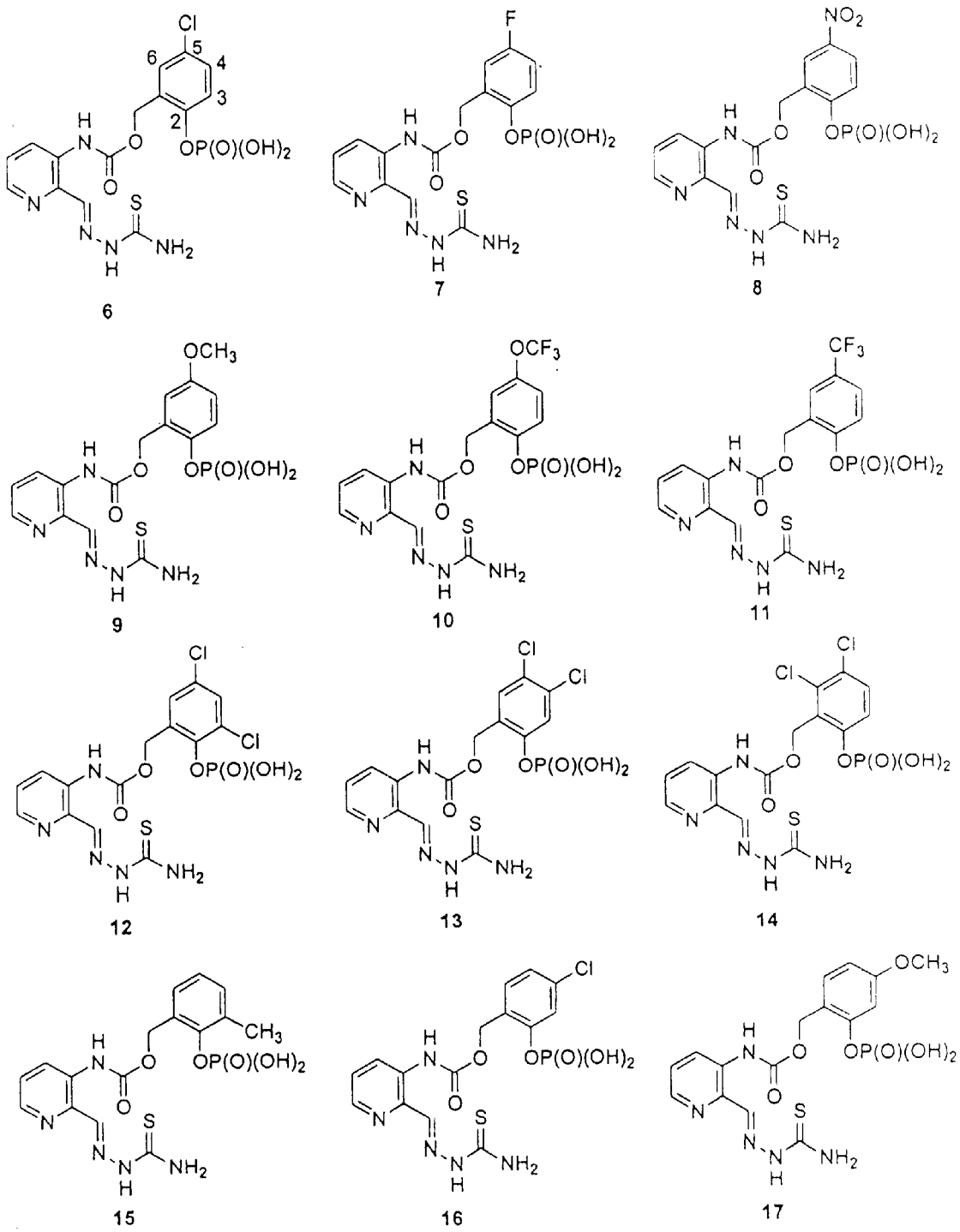
FIG. 1 is a representation of certain chemical embodiments according to the present invention.

The following terms shall be used throughout the specification to describe the present invention.

The term "patient" is used throughout the specification to describe an animal, including a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

The term "effective amount" is used throughout the specification to describe concentrations or amounts of compounds according to the present invention which may be used to produce a favorable change in the disease or condition treated, whether that change is a remission, a decrease in growth or size of cancer or a tumor, a favorable physiological result, a reduction in the growth or elaboration of a microbe, or the like, depending upon the disease or condition treated.

The term "alkyl" is used throughout the specification to describe a hydrocarbon radical containing between one and three carbon units. Alkyl groups for use in the present invention include linear or branched-chain groups, such as methyl, ethyl, propyl and isopropyl.

The term "salt" shall mean any salt consistent with the use of the compounds according to the present invention. In the case where the compounds are used in pharmaceutical indications, including the treatment of neoplasia, including cancer, the term "salt" shall mean a pharmaceutically acceptable salt, consistent with the use of the compounds as pharmaceutical agents.

The term "neoplasia" is used to describe the pathological process that results in the formation and growth of a neoplasm, i.e., an abnormal tissue that grows by cellular proliferation more rapidly than normal tissue and continues to grow after the stimuli that initated the new growth cease. Neoplasia exhibits partial or complete lack of structural organization and functional coordination with the normal tissue, and usually forms a distinct mass of tissue which may be benign (benign tumor) or malignant (carcinoma). The term "cancer" is used as a general term to describe any of various types of malignant neoplasms, most of which invade surrounding tissues, may metastasize to several sites and are likely to recur after attempted removal and to cause death of the patient unless adequately treated. As used herein, the term cancer is subsumed under the term neoplasia.

A preferred therapeutic aspect according to the present invention relates to methods for treating neoplasia, including benign and malignant tumors and cancer in animal or human patients, and in preferred embodiments, cancers which have developed drug resistance, such as multiple drug resistant breast cancer comprising administering therapeutically effective amounts or concentrations of one or more of the compounds according to the present invention to inhibit the growth or spread of or to actually shrink the neoplasia in the animal or human patient being treated.

Cancers which may be treated using compositions according to the present invention include, for example, stomach, colon, rectal, liver, pancreatic, lung, breast, cervix uteri, corpus uteri, ovary, prostate, testis, bladder, renal, brain/cns, head and neck, throat, Hodgkins disease, non-Hodgkins leukemia, multiple myeloma leukemias, skin melanoma, acute lymphocytic leukemia, acute mylogenous leukemia, Ewings Sarcoma, small cell lung cancer, choriocarcinoma, rhabdomyosarcoma, Wilms Tumor, neuroblastoma, hairy cell leukemia, mouth/pharynx, oesophagus, larynx, melanoma, kidney and lymphoma, among others. Compounds according to the present invention are particularly useful in the treatment of lung cancer, breast cancer and prostate cancer.

In the present methods, in certain preferred embodiments, it has been found advantageous to coadminister at least one additional anti-neoplastia agent for the treatment of neoplasia, including cancer. In these aspects according to the present invention, an effective amount of one or more of the compounds according to the present invention is co-administered along with an effective amount of at least one additional anti-neoplastia/anti-cancer agent such as, for example, cytoxan (cylophosphamide), mitomycin C, and Etoposide, among numerous others, including topo I and topo II agents, such as adriamycin, topotecan and irinotecan, other agents such as gemcitabine, campothecin and agents based upon campothecin and cis-platin, among other alkylating agents, including chlorambucil and melphalan. It has unexpectedly been found that the present compounds (as well the compound where $R_3$, $R_4$, $R_5$ and $R_6$ are H), which act by a mechanism to reduce or prevent DNA repair, will act synergistically with compounds which act by damaging DNA. Thus, the present compounds may be advantageously combined with any compound which acts by damaging DNA, especially including alkylating agents and platinating agents. By "co-administer" it is meant that the present compounds are administered to a patient such that the present compounds as well as the co-administered compound may be found in the patient's bloodstream at the same time, regardless when the compounds are actually administered, including simultaneously. In many instances, the co-administration of the present compounds with traditional anti-cancer agents produces a synergistic (i.e., more than additive) result which is unexpected.

Pharmaceutical compositions based upon the present novel chemical compounds comprise the above-described compounds in a therapeutically effective amounts for the treatment of a condition or disease such as neoplasia, including cancer, optionally in combination with a pharmaceutically acceptable additive, carrier or excipient.

Certain of the compounds, in pharmaceutical dosage form, may be used as prophylactic agents for preventing a disease or condition from manifesting itself.

The present compounds or their derivatives can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts inlcude the sodium and potassium salts of phosphate, among others. Modifications of the active compound can affect the solubility, bioavailability and rate of metabolism of the active species, thus providing control over the delivery of the active species. Further, the modifications can affect the anticancer activity of the compound, in some cases increasing the activity over the parent compound. This can easily be assessed by preparing the derivatives and testing the anticancer activity according to known methods well within the routineer's skill in the art.

The compounds of this invention may be incorporated into formulations for all routes of administration including for example, oral and parenteral, including intravenous, intramuscular, intraperitoneal, intrabuccal, transdermal and in suppository form. Parenteral administration and in particular, intravenous or intramuscular administration is preferred.

Pharmaceutical compositions based upon these novel chemical compounds comprise the above-described compounds in a therapeutically effective amount for treating neoplasia, cancer and other diseases and conditions which have been described herein, optionally in combination with a pharmaceutically acceptable additive, carrier and/or excipient. One of ordinary skill in the art will recognize that a therapeutically effective amount of one of more compounds according to the present invention will vary with the infection or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition parenterally and in particular, in intravenously or intramuscular dosage form, but a number of formulations may be administered via other parenteral routes, such as transdermal, buccal, subcutaneous, suppository or other route, including via an oral route of administration. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (such as salt formulation, etc.) which are well within the ordinary skill in the art. It is also well within the routineer's skill to modify the route of administration and dosage regimen of a particular compound in order to manage the pharmacokinetics of the present compounds for maximum beneficial effect to the patient.

The routineer will take advantage of favorable pharmacokinetic parameters of the pro-drug forms of the present invention, where applicable, in delivering the present compounds to a targeted site within the host organism or patient to maximize the intended effect of the compound.

The amount of compound included within therapeutically active formulations according to the present invention is an effective amount for treating the infection or condition. In its most preferred embodiment, the present compounds, and in particular, compounds where $R_4$ is Cl or $R_5$ is F, Cl, $OCH_3$ or $OCF_3$ and the remaining substituents on the benzene ring (other than the phosphate and urethane moiety) are H, preferably are used for treating neoplasia, and in particular, cancer, including, in certain instances, drug resistant cancers. In general, a therapeutically effective amount of the present preferred compound in dosage form usually ranges from slightly less than about 0.025 mg./kg. to about 2.5 g./kg., preferably about 2.5–5 mg/kg to about 100 mg/kg of the patient or considerably more, even more preferably about 20–50 mg/kg, more preferably about 25 mg/kg, depending upon the compound used, the condition or infection treated and the route of administration, although exceptions to this dosage range may be contemplated by the present invention. In the case of the preferred compositions according to the present invention as described above where $R_4$ is Cl or $R_5$ is F, Cl, $OCH_3$ or $OCF_3$ and the remaining substituents on the benzene (other than the phosphate and urethane moiety) are H, because the compounds exhibit enhanced anti-cancer activity, combined with reduced overall toxicity non-cancerous host cells and the bioavailability of the compounds is also high, these compounds may be administered at levels 3–10 fold higher than triapine 1A with significantly less toxicity. At these doses, the AUC (area under the curve) of triapine delivered from the prodrug form is about 5 to 25 times greater than that achieveable by the administration of triapine in non-prodrug form. The compounds according to the present invention, therefore, represent an unexpected result and are exceptional agents for the treatment of neoplasia, especially cancer. The dosage range chosen for these agents as set forth above is effective to generally produce effective blood level concentrations of active compound, which may range from less than about 0.04 to about 400 micrograms/cc or more of blood in the patient. The more favorable bioavailablility characteristics, coupled with the reduced toxicity and greater activity of the present compounds on a molar basis compared to the prior art Triapine™, evidences the present compounds as unexpectedly favorable compounds for use in the treatment of neoplasia, including cancer.

Administration of the active compound may range from continuous (intravenous drip), including bolus administration, intravenously or intramuscularly even less frequently than once a day to several administrations per day and may include topical, parenteral, intramuscular, intravenous, sub-cutaneous, transdermal (which may include a penetration enhancement agent), buccal and suppository administration, among other routes of administration, including, in certain instances, oral administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., intravenous or intramuscular. In preparing pharmaceutical compositions in the appropriate dosage form, any of the usual pharmaceutical media may be used. For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

The present compounds may be used to treat animals, and in particular, mammals, including humans, as patients. Thus, humans, equines, canines, bovines and other animals, and in particular, mammals, suffering from tumors, and in particular, cancer, or other diseases as disclosed herein, can be treated by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents, depending upon the disease to be treated). This treatment can also be administered in conjunction with other conventional cancer therapies, such as radiation treatment or surgery.

The active compound is included in the pharmaceutically acceptable carrier or diluent in an amount sufficient to deliver to a patient a therapeutically effective amount for the desired indication, without causing serious toxic effects in the patient treated.

The compound is conveniently administered in any suitable unit dosage form, including but not limited to one containing 1 to 3000 mg, preferably 5 to 500 mg of active ingredient per unit dosage form.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The active compound according to the present invention can also be mixed with other active materials that do not impair the desired action, or with materials that supplement the desired action, such as other anticancer agents, and in certain instances depending upon the desired therapy or target, antibiotics, antifungals, antinflammatories, or antiviral compounds, among others agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, preferred carriers include, for example, physiological saline or phosphate buffered saline (PBS).

In one embodiment, the active compounds may be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art. For example, liposome formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

A wide variety of biological assays have been used and are accepted by those skilled in the art to assess anti-cancer activity of compounds. Any of these methods can be used to evaluate the activity of the compounds disclosed herein.

One common method of assessing activity is through the use of test panels of cancer cell lines. These tests evaluate the in vitro anti-cancer activity of particular compounds in cancer cell lines, and provide predictive data with respect to the use of tested compounds in vivo. Other assays include in vivo evaluations of the compound's effect on human or in an appropriate animal model, for example, using mouse tumor cells implanted into or grafted onto mice or in other appropriate animal models.

Chemical Synthesis

Preliminary in vitro evaluation of the 3-AP prodrugs showed that they were rapidly converted to 3-AP by alkaline phosphatase enzyme. In contrast, the in vivo PK studies in Beagle dogs showed that 3-AP released from ortho phosphate-bearing prodrug with a half-life of 14.2 h, whereas para prodrug has a half-life of 1.5 h. Prodrugs 2 and 3 were also evaluated in the M-109 solid tumor bearing mice in vivo against 3-AP and cytoxan. The results from these experiments showed that the ortho prodrug 3 has better efficacy with reduced toxicity than the parent 3-AP (1A) and has comparable activity to that of cytoxan. With the aim to further improve the biological and pharmaceutical profiles and to maximize the therapeutic utility of the 3-AP prodrugs, a series of ortho phosphate-bearing prodrugs were designed based on the following rationale.

The rationale for the new prodrug design was that the 3-AP phosphate-linked prodrugs can release 3-AP via a sequence of dephosphorylation to give 4 and subsequent benzyl group fragmentation to give quinone methide 5 which can act as a biological alkylating agent.

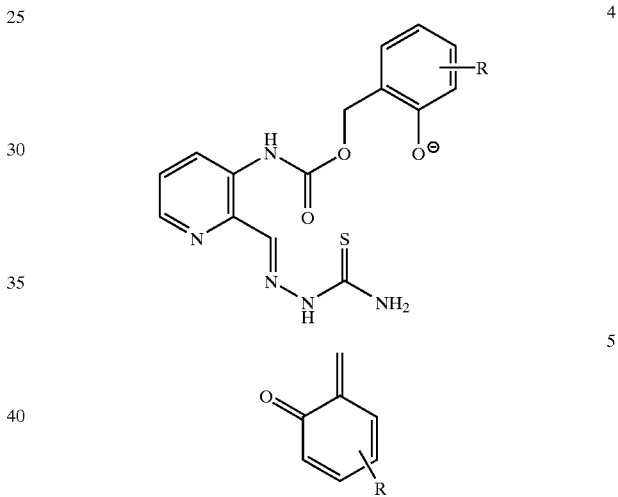

While not being limited by way of theory, it is theorized that the rate-determining step in this prodrug activation process would appear to be the P—O bond cleavage step, which is catalyzed by alkaline phosphatase. The subsequent fragmentation step is usually rapid. It is possible that 3-AP prodrugs with longer half-lives in circulation, allowing them to act as a 3-AP depot; or prodrugs with a different distribution than that of the parent drug, may have desirable properties. One approach to this goal is to slow down the dephosphorylation step, the rate-limiting step in the bioactivation of 3-AP phosphate-bearing prodrugs by introducing bulky substituents at the position alpha to the phosphate group. These alkyl groups may impose steric hindrance by the close proximity to the P—O bond cleavage site, thereby slowing down the enzymatic dephosphorylation event. Another approach is to introduce electron-releasing or electron-withdrawing groups in the phenyl ring which may effect the rate of P—O bond cleavage. Similarly, the subsequent fragmentation step also may be effected by substitution at other positions with electron-releasing and electron-withdrawing groups.

Based on these considerations, a number of phosphate bearing prodrugs (FIG. 1) were synthesized readily in good quantities and evaluated. The disodium salts of these prodrugs were very soluble in water.

Figure 2:
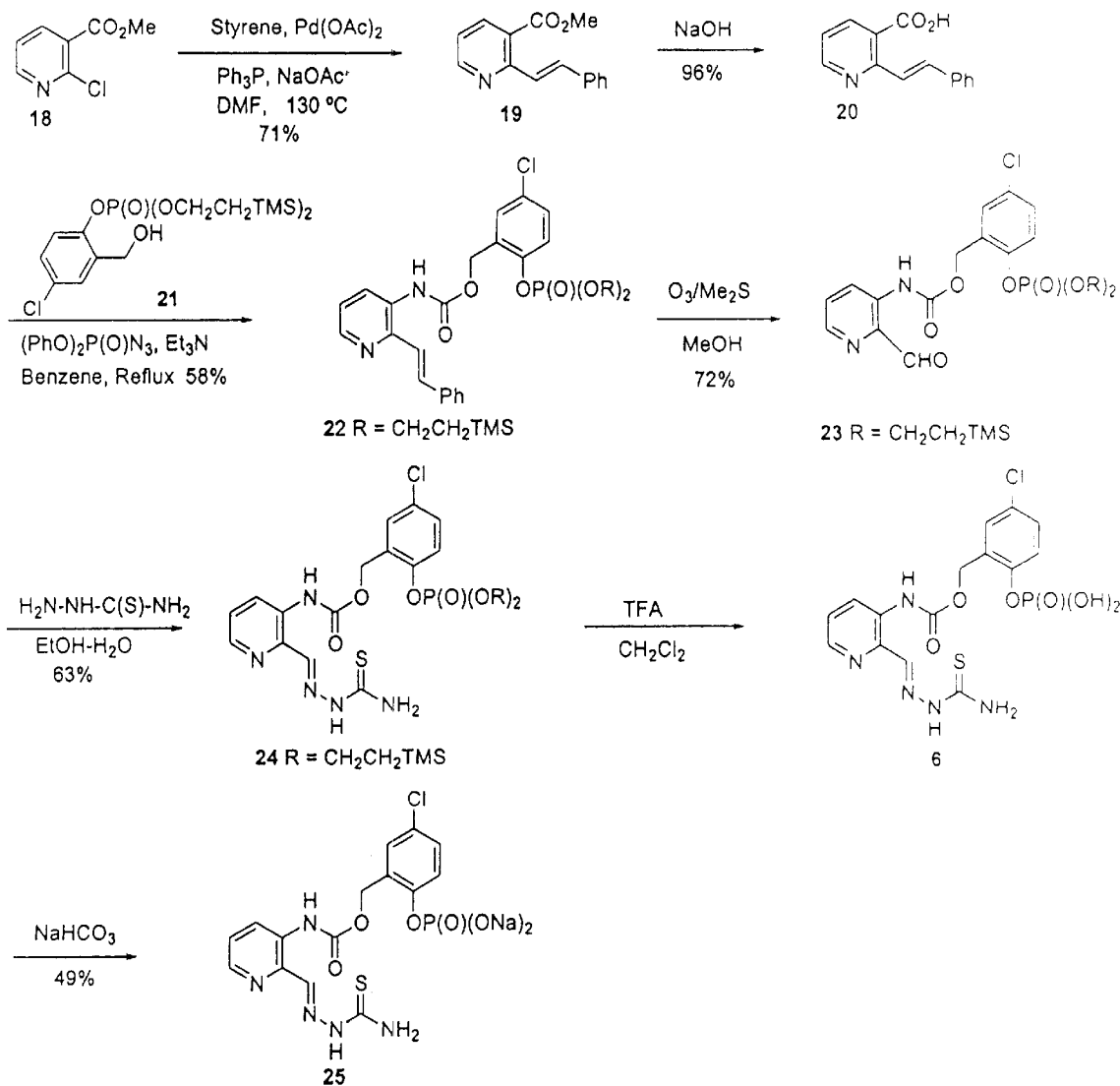
FIGS. 2–3 are representations of chemical schemes for synthesizing compounds according to the present invention.

The 5-chloro prodrug compound 6 was synthesized as shown in FIG. 2. Thus, the acid 20 was prepared from, for example, 2-chloro-3-nicotinic acid methyl ester 18 or a related derivative in a two-step sequence consisting of a Heck reaction (See, Jeffery, *Tetrahedron* (1996), 52, 10113 and Dieck and Heck, *J. Org. Chem.* (1975), 40, 1083) and a NaOH promoted ester hydrolysis. The chloro orthophosphate linker 21 was prepared via an oxidative coupling between the bis-TMSE-phosphite (McCombie, et al., *J. Chem. Soc.* (1945), 381) and 2-hydroxybenzyl alcohol. Initially, problems were encountered in the large-scale preparation of linker 21 as it decomposed during purification giving low yields. The conditions were standardized by using $Et_3N$ as buffer to neutralize the acidity of silica gel to obtain the linker in good quantities (88%). Heating a reaction mixture consisting of the acid 20, the linker 21, triethylamine and diphenylphosphoryl azide under Curtius rearrangement conditions (Shipps, et al., *J. Bioorg. Med. Chem.* (1996), 4, 655) provided the desired carbamate 22 (58%), which was converted sequentially to the aldehyde 23 (72%) and its corresponding thio-semicarbazone 24 in 63% yield. The removal of the 2-trimethylsilylethyl(TMSE) group in 24 was effected cleanly with TFA (Chao, et al., *J. Org. Chem.* (1994), 59, 6687) and provided the 3-AP prodrug free acid 6, which was in turn converted to the disodium salt 25 upon treatment with saturated sodium bicarbonate solution and reverse phase column purification.

Figure 3:
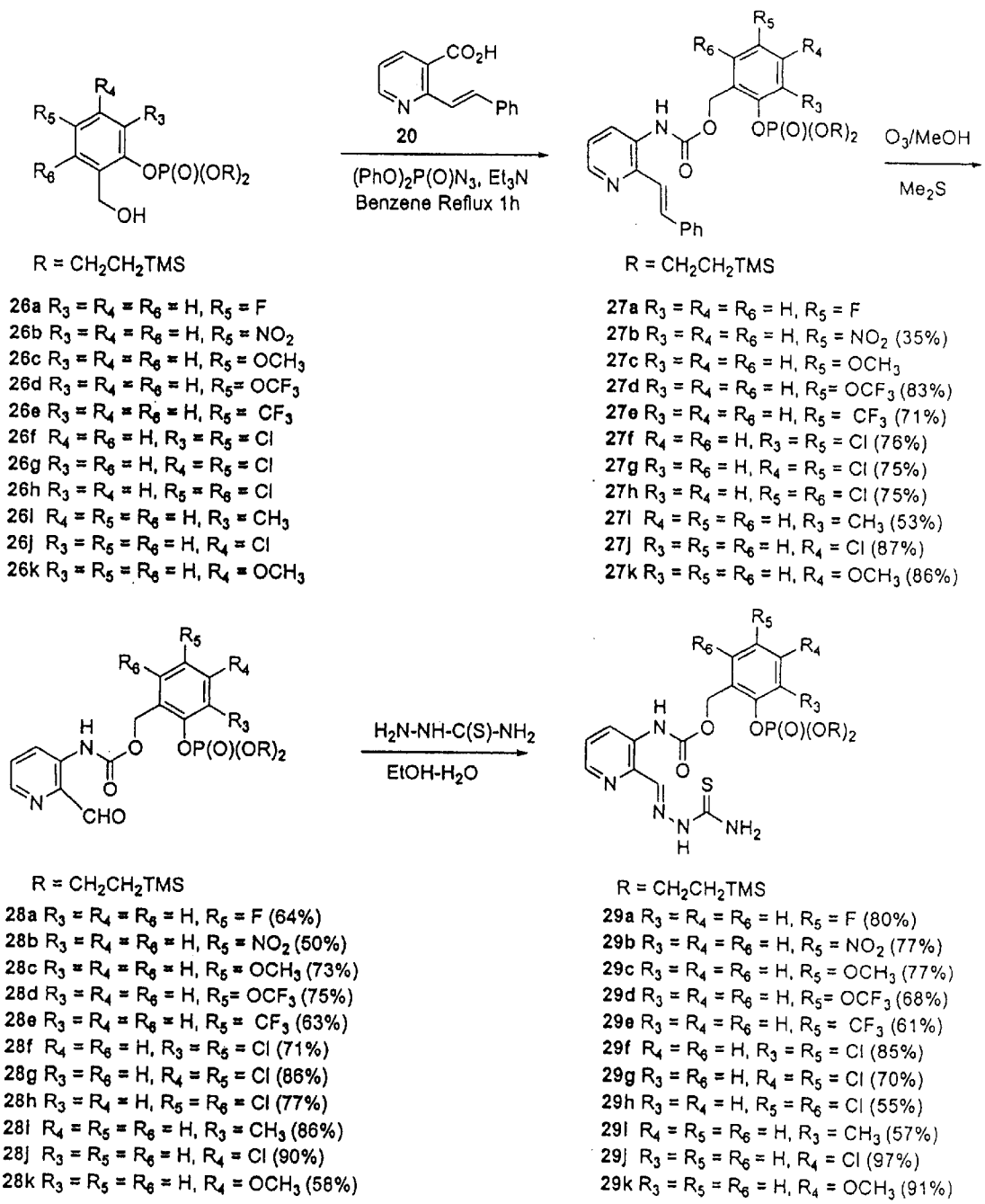

The other substituted ortho prodrugs were synthesized essentially following the same route using appropriate phosphate-bearing substituted benzyl linkers such as 21. Coupling of these linkers to 25, followed by functional group manipulations furnished the corresponding prodrugs (FIG. 3). The synthesis evidences that the prodrugs of the present invention may be readily converted to their corresponding phosphate salts. The water solubility of these phosphate salt compounds is excellent and is significantly greater than corresponding non-prodrug forms. The solubility of parental 3-AP in aqueous solution is less than 0.1 mg/ml, where as that of the prodrugs is between 16 and 35 mg/ml.

Having generally described the invention, reference is now made to the following specific examples which are intended to illustrate preferred and other embodiments and comparisons. The included examples are not to be construed as limiting the scope of this invention as is more broadly set forth above and in the appended claims. Other compounds not specifically presented in the examples section of this application may be readily synthesized following analogous methodologies and/or facile syntheses which are presented and known in the art. One of ordinary skill may readily synthesize all compounds set forth and described without engaging in undue experimentation by simply following the detailed synthetic methodology directly or adapting/modifying such synthetic methodology using techniques well known in the art.

EXAMPLES

All reagents were purchased at commercial quality and used without further purification, and solvents were dried and/or distilled before use where necessary. All NMR spectra ($^1H$, $^{13}C$, and $^{31}P$) were determined on a Brucker AC300 spectrometer. Chemical shifts are measured in parts per million (ppm) relative to tetramethylsilane. Coupling constants are reported in hertz (Hz). Flash column chromatography (FCC) was performed with Merck silica gel 60 (230–400 mesh), and pre-treated with triethylamine for all trimethylsilylethyl (TMSE) protected compounds. Reversed phase column chromatography (RPCC) was packed with CAT gel (Waters, preparative C18 125 Å, 55–105 µm), eluting with milli-Q de-ionized water.

Examples 1–3

General Procedures for Preparation of the Nicotinic Acid (20)

Example 1

Preparation of 2-chloronicotinic acid methyl ester (18)

To a mixture of 2-chloronicotinic acid (Aldrich, 100.0 g, 0.63 mol) in 1,4-dioxane (500 mL) was added thionyl chloride (70 mL, 0.96 mol). The suspension was heated under reflux for 22 h with a gas trap to absorb hydrogen chloride gas. After evaporation of the solvent, the residue was dissolved in methanol (300 mL). To the solution was added dropwise triethylamine (TEA, 120 mL, 1.26 mol) at 0° C. over 2 h. The solvents were evaporated and the residue was suspended in ethyl acetate. The precipitate was removed by filtration. The filtrate was concentrated to afford the ester 18 (92.3 g, 86%) as an oil:

Rf (1:5 v/v ethyl acetate-hexane) 0.38.

$^1H$ NMR (300 MHz, $CDCl_3$) δ8.53 (dd, 4.8 Hz, 1H), 8.19 (dd, 7.6 Hz, 1H), 7.37 (dd, 7.7 Hz, 1H) and 3.97 (s, 3H).

$^{13}C$ NMR (75 MHz, $CDCl_3$) δ164.5, 151.6, 149.6, 140.0, 126.4, 121.9 and 52.5.

Example 2

Preparation of 2-styrylnicotinic acid methyl ester (19)

To a solution of the ester 18 (48.8 g, 0.28 mol) in DMF (450 mL) was added styrene (165 mL, 1.42 mol), palladium acetate (6.5 g, 30 mmol), sodium acetate (47 g, 0.57 mol) and triphenyl phosphine (30 g, 0.11 mol). The mixture was heated under reflux for 22 h. The palladium-catalyst was removed by filtration through a Celite pad. The filtrate was concentrated under reduced pressure, and the residue was dissolved in a minimum amount of ethyl acetate. To the above solution was added hexane. After removal of the precipitate by filtration, the filtrate was concentrated. The resulting crude material was purified by FCC (1:1 v/v ethyl acetate-hexane) to afford the ester 19 (55.0 g, 81%) as a light yellow oil:

Rf (1:5 v/v ethyl acetate-hexane) 0.41.

$^1H$ NMR (300 MHz, $CDCl_3$) δ8.70 (dd, 1H), 8.10 (dd, 1H), 8.16 (d, 1H), 7.94 (d, 1H), 7.64 (d, 2H), 7.4–7.3 (m, 3H), 7.18 (dd, 1H) and 3.94 (s, 3H).

$^{13}C$ NMR (75 MHz, $CDCl_3$) δ166.7, 155.3, 152.0, 138.6, 136.7, 135.9, 128.6, 128.5, 127.5, 124.8, 123.8, 121.3 and 52.4.

Example 3

Preparation of 2-styrylnicotinic acid (20)

A solution of the ester 19 (55.0 g, 0.23 mol) in THF (100 mL) was treated with a 3 N NaOH solution (110 mL, 0.25 mol) for 21 h at ambient temperature. After removal of solvents, the residue was taken up in water and ethyl ether. The phases were separated, and the aqueous phase was washed with ether (2×). The resulting aqueous phase was neutralized with a 2 N HCl solution, and the precipitate was then collected by filtration to afford the acid 20 (50.2 g, 97%) as a cream solid:

$^{1}$H NMR (300 MHz, DMSO-d$_6$) δ8.72 (dd, 1H), 8.19 (dd, 1H), 8.10 (d, 1H), 7.86 (d, 1H), 7.62 (d, 2H) and 7.4–7.3 (m, 4H).

$^{13}$C NMR (75 MHz, DMSO-d$_6$) δ167.9, 153.7, 151.8, 138.6, 136.4, 134.5, 128.9, 128.7, 127.2, 125.3 and 122.1.

Examples 4–5

General Procedures for Preparation of the Phosphate Linkers (21, 26a–k)

Example 4

Preparation of bis(2-trimethylsilylethyl)phosphite (TMSE-phosphite)

To a solution of 2-(trimethylsilyl)ethanol (Aldrich, 25.0 g, 0.21 mol) in ethyl ether (200 mL) containing pyridine (11.4 mL, 0.14 mol) was added phosphorus trichloride (6.2 mL, 70 mmol) in one portion at −78° C. The reaction mixture was kept for 5 min while stirring, and then diluted with ethyl ether (500 mL). After warming to ambient temperature, the mixture was stirred for 18 h continually. The precipitate was removed by filtration, and the filtrate was then bubbled by ammonia gas for 10 min. The precipitate was removed by filtration through a Celite pad, and the filtrate was concentrated to afford TMSE-phosphite (20.7 g, 99%) as a colorless oil:

$^{1}$H NMR (300 MHz, CDCl$_3$) δ6.76 (d, 1H), 4.13 (m, 4H), 1.07 (m, 4H) and 0.0 (s, 18H).

$^{13}$C NMR (75 MHz, CDCl$_3$) δ64.0 (d), 19.6 (d) and −1.6 (d).

$^{31}$P NMR (121 MHz, CDCl$_3$) δ18.5.

Example 5

Preparation of 2-(TMSE-phosphonooxy)benzyl alcohols (21, 26a–k)

General Procedure. To a solution of the corresponding 2-hydroxybenzyl alcohol (10 mmol) in acetonitrile (40 mL) was added N,N'-diisopropylethylamine (DIEA, 11 mmol), 4-dimethylaminopyridine (DMAP, 1 mmol), and carbon tetrachloride (50 mmol). While stirring at −30° C., to the solution was added bis(2-trimethylsilylethyl)phosphite (stored in refrigerator, 11 mmol) immediately. After warming to ambient temperature, the reaction mixture was stirred for 3 h. The solvents were evaporated under reduced pressure, and the residual product was purified by FCC (1:1 v/v ethyl acetate-hexane) to afford the corresponding TMSE-protected phosphate linker (21, 26a–k).

2-Bis(2-trimethylsilylethyl)phosphonooxybenzyl alcohol (5 position on phenyl group is H, 21a)

Following the above procedure, 2-hydroxybenzyl alcohol (15.0 g, 0.12 mmol) gave the ortho phosphate linker 2-Bis (2-trimethylsilyethyl)phosphonooxybenzyl alcohol (39.78 g, 81%) as an oil:

$^{1}$H NMR (300 MHz, CDCl$_3$) δ7.43 (d, J=8.5 Hz, 1H), 7.27–7.16 (m, 3H), 4.63 (s, 2H), 4.29–4.19 (m, 4H), 4.12 (m, 4H), 1.14–1.08 (m, 4H), and 0.00 (s, 18H);

$^{13}$C NMR (75 MHz, CDCl$_3$) δ148.4 (d, J=8.84 Hz), 133.0 (d, J=4.59 Hz), 130.9, 129.1, 25.8, 121.0 (d, J=4.47 Hz), 67.5 (d, J=6.93), 60.1, 9.5 (d, J=5.76 Hz) and −1.563.

$^{31}$P NMR (121 MHz, CDCl$_3$) δ6.4.

2-Bis(2-trimethylsilylethyl)phosphonooxy-5-chlorobenzyl alcohol (21)

Following the above procedure, 5-chloro-2-hydroxybenzyl alcohol (5.0 g, 32 mmol) gave 21 (12.2 g, 88%) as an oil:

$^{1}$H NMR (300 MHz, CDCl$_3$) δ7.33 (d, 1H), 7.11 (m, 1H), 7.02 (m, 1H), 4.49 (s, 2H), 4.12 (m, 4H), 1.00 (m, 4H) and −0.07 (s, 18H).

$^{13}$C NMR (75 MHz, CDCl$_3$) δ146.5 (d), 134.7 (d), 130.8, 130.2, 128.6, 122.0 (d), 67.7 (d), 59.4, 19.5 (d) and −1.6.

$^{31}$P NMR (121 MHz, CDCl$_3$) δ6.1.

2-Bis(2-trimethylsilylethyl)phosphonooxy-5-fluorobenzyl alcohol (26a)

Following the above procedure, 5-fluoro-2-hydroxybenzyl alcohol (17.0 g, 119 mmol) gave 26a (31.7 g, 62%) as an oil:

$^{1}$H NMR (300 MHz, CDCl$_3$) δ7.2–7.1 (m, 1H), 7.0–6.9 (m, 1H), 4.63 (s, 1H), 4.3–4.1 (m, 4H), 1.2–1.1 (m, 4H) and 0.0 (s, 18H).

$^{13}$C NMR (75 MHz, CDCl$_3$) δ159.8 (d), 143.7 (dd), 135.2 (dd), 121.8 (dd), 116.4 (d), 115.0 (d), 67.6 (d), 59.4, 19.5 (d) and −1.6. $^{31}$P NMR (121 MHz, CDCl$_3$) δ6.4.

$^{19}$F NMR (282 MHz, CDCl$_3$) δ−59.8.

2-Bis(2-trimethylsilylethyl)phosphonooxy-5-nitrobenzyl alcohol (26b)

Following the above procedure, 2-hydroxy-5-nitrobenzyl alcohol (4.5 g, 27 mmol) gave 26b (6.4 g, 53%) as an oil:

$^{1}$H NMR (300 MHz, CDCl$_3$) δ8.14 (m, 1H), 7.81 (m, 1H), 7.14 (m, 1H), 4.48 (s, 2H), 4.06 (m, 4H), 0.90 (m, 4H) and −0.20 (m, 18H).

$^{13}$C NMR (75 MHz, CDCl$_3$) δ152.0 (d), 144.6, 134.7 (d), 123.7, 123.4, 119.8, 67.9 (d), 58.4, 19.3 (d) and −1.6.

$^{31}$P NMR (121 MHz, CDCl$_3$) δ4.4.

2-Bis(2-trimethylsilylethyl)phosphonooxy-5-methoxybenzyl alcohol (26c)

Following the above procedure, 2-hydroxy-5-methoxybenzyl alcohol (11.0 g, 25 mmol) gave 26c (7.7 g, 70%) as an oil:

$^{1}$H NMR (300 MHz, CDCl$_3$) δ7.06 (dd, 1H), 6.94 (d, 1H), 6.74 (dd, 1H), 4.57 (s, 2H), 4.3–4.1 (m, 4H), 3.74 (s, 3H), 1.1–1.0 (m, 4H) and 0.0 (m, 18H).

$^{13}$C NMR (75 MHz, CDCl$_3$) δ157.1, 141.7 (d), 134.0 (d), 121.9 (d), 125.3, 114.5, 67.5 (d), 60.2, 55.6, 19.6 (d) and −1.6.

$^{31}$P NMR (121 MHz, CDCl$_3$) δ6.9.

2-Bis(2-trimethylsilylethyl)phosphonooxy-5-trifluoromethoxybenzyl alcohol (26d)

Following the above procedure, 2-hydroxy-5-trifluoromethoxybenzyl alcohol (1.9 g, 9.1 mmol) gave 26d (3.3 g, 62%) as an oil:

$^{1}$H NMR (300 MHz, CDCl$_3$) δ7.20 (d, 1H), 7.19 (dd, 1H), 7.09 (dd, 1H), 4.61 (s, 2H), 4.24 (m, 4H), 1.08 (m, 4H) and 0.0 (s, 18H).

$^{13}$C NMR (75 MHz, CDCl$_3$) δ146.4 (dd), 135.0 (d), 123.0, 122.1, 121.4, 67.8 (d), 59.6, 19.6 (d) and −1.6.

$^{31}$P NMR (121 MHz, CDCl$_3$) δ6.2.

$^{19}$F NMR (282 MHz, CDCl$_3$) δ−58.7.

2-Bis(2-trimethylsilylethyl)phosphonooxy-5-trifluoromethylbenzyl alcohol (26e)

Following the above procedure, 2-hydroxy-5-trifluoromethylbenzyl alcohol (4.1 g, 22 mmol) gave 26e (7.9 g, 77%) as an oil:

$^{1}$H NMR (300 MHz, CDCl$_3$) δ7.72 (br s, 1H), 7.51 (dd, 1H), 7.29 (d, 1H), 4.66 (s, 2H), 4.23 (m, 4H), 1.09 (m, 4H) and 0.0 (s, 18H).

$^{13}$C NMR (75 MHz, CDCl$_3$) δ150.6 (d), 133.8 (d), 127.7 (d), 126.1, 121.3 (d), 68.0 (d), 59.6, 19.6 (d) and −1.6.

$^{31}$P NMR (121 MHz, CDCl$_3$) δ5.8.
$^{19}$F NMR (282 MHz, CDCl$_3$) δ−62.9.

2-Bis(2-trimethylsilylethyl)phosphonooxy-3,5-dichlorobenzyl alcohol (26f)

Following the above procedure, 3,5-dichloro-2-hydroxybenzyl alcohol (4.6 g, 24 mmol) gave 26f (7.2 g, 63%) as an oil:
$^1$H NMR (300 MHz, CDCl$_3$) δ7.34 (d, 1H), 7.32 (dd, 1H), 4.56 (s, 2H), 4.25 (m, 4H), 1.08 (m, 4H) and 0.0 (s, 18H).
$^{13}$C NMR (75 MHz, CDCl$_3$) δ149.9, 143.3 (d), 136.9 (d), 131.2 (d), 129.9, 129.5, 127.6 (d), 68.3 (d), 59.8, 19.5 (d) and −1.6.
$^{31}$P NMR (121 MHz, CDCl$_3$) δ5.7.

2-Bis(2-trimethylsilylethyl)phosphonooxy-4,5-dichlorobenzyl alcohol (26g)

Following the above procedure, 4,5-dichloro-2-hydroxybenzyl alcohol (3.6 g, 18 mmol) gave 26g (5.2 g, 59%) as an oil:
$^1$H NMR (300 MHz, CDCl$_3$) δ7.53 (s, 1H), 7.28 (s, 1H), 4.55 (s, 2H), 4.21 (m, 4H), 1.08 (m, 4H) and 0.0 (s, 18H).
$^{13}$C NMR (75 MHz, CDCl$_3$) δ146.6 (d), 133.5 (d), 131.9 (d), 131.6, 129.5 (d), 123.0 (d), 68.1 (d), 59.1, 19.6 (d) and −1.5.
$^{31}$P NMR (121 MHz, CDCl$_3$) δ6.0.

2-Bis(2-trimethylsilylethyl)phosphonooxy-5,6-dichlorobenzyl alcohol (26h)

Following the above procedure, 5,6-dichloro-2-hydroxybenzyl alcohol (4.8 g, 25 mmol) gave 26h (8.6 g, 73%) as an oil:
$^1$H NMR (300 MHz, CDCl$_3$) δ7.35 (d, 1H), 7.04 (dd, 1H), 4.76 (s, 2H), 4.22 (m, 4H), 1.08 (m, 4H) and 0.0 (s, 18H).
$^{13}$C NMR (75 MHz, CDCl$_3$) δ147.6 (d), 134.7, 133.5 (d), 130.6 (d), 129.9, 120.8 (d), 68.1 (d), 57.3, 19.6 (d) and −1.6.
$^{31}$P NMR (121 MHz, CDCl$_3$) δ6.4.

2-Bis(2-trimethylsilylethyl)phosphonooxy-3-methylbenzyl alcohol (26i)

Following the above procedure, 2-hydroxy-3-methylbenzyl alcohol (2.0 g, 14 mmol) gave 26i (1.7 g, 88%) as an oil:
$^1$H NMR (300 MHz, CDCl$_3$) δ7.16 (m, 1H), 7.0–6.9 (m, 2H), 4.48 (s, 2H), 4.13 (m, 4H), 2.22 (s, 3H), 0.97 (m, 4H) and −0.09 (s, 18H).
$^{13}$C NMR (75 MHz, CDCl$_3$) δ146.9 (d), 133.5 (d), 131.0, 130.4 (d), 129.4, 125.6 (d), 67.6 (d), 60.1, 19.5 (d), 16.8 and −1.6.
$^{31}$P NMR (121 MHz, CDCl$_3$) δ6.9.

2-Bis(2-trimethylsilylethyl)phosphonooxy-4-chlorobenzyl alcohol (26j).

Following the above procedure, 4-chloro-2-hydroxybenzyl alcohol (4.2 g, 26 mmol) gave 26j (9.6 g, 84%) as an oil:
R$_f$ (4:1 v/v ethyl acetate-hexane) 0.67.
$^1$H NMR (300 MHz, CDCl$_3$) δ7.27 (d, 1H), 7.2–7.1 (m, 2H), 4.55 (s, 2H), 4.21 (m, 4H), 1.07 (m, 4H) and 0.0 (s, 18H).
$^{13}$C NMR (75 MHz, CDCl$_3$) δ148.5 (d), 133.9, 131.7 (d), 131.5, 126.0, 121.4 (d), 67.9 (d), 59.4, 19.5 (d) and −1.6.
$^{31}$P NMR (121 MHz, CDCl$_3$) δ5.8.

2-Bis(2-trimethylsilylethyl)phosphonooxy-4-methoxybenzyl alcohol (26k)

Following the above procedure, 2-hydroxy-4-methoxybenzyl alcohol (2.7 g, 17 mmol) gave 26k (2.5 g, 33%) as an oil:
Rf (4:1 v/v ethyl acetate-hexane) 0.70.
$^1$H NMR (300 MHz, CDCl$_3$) δ7.29 (d, 1H), 6.8–6.7 (m, 2H), 4.53 (s, 2H), 4.22 (m, 4H), 3.75 (s, 3H), 1.09 (m, 4H) and 0.0 (s, 18H).
$^{13}$C NMR (75 MHz, CDCl$_3$) δ160.1 (d), 149.1 (d), 131.9, 125.3 (d), 111.2, 107.3 (d), 67.6 (d), 59.7, 55.5, 19.6 (d) and −1.6.
$^{31}$P NMR (121 MHz, CDCl$_3$) 67 6.4.

Examples 6–10

General Procedures for Preparation of the 3-AP Prodrugs (25, 30a–k)

Example 6

Preparation of (2-styrylpyridin-3-yl)carbamic acid 2-(TMSE-phosphonooxy)benzyl esters (22, 27a–k) (Curtius Rearrangement)

General Procedure. To a solution of 2-styrylnicotinic acid (20, 20 mmol) in benzene (100 mL) containing triethylamine (TEA, 32 mmol) was added diphenylphosphorylazide (32 mmol). The solution was heated at reflux for 10 min, and the corresponding TMSE-protected phosphate linker (21 or 26a–k, 20 mmol), prepared as described above, was then added. The reaction mixture was kept under reflux for 3 h. Next, the solvents were evaporated under reduced pressure. The residual product was purified by FCC (1:4 v/v ethyl acetate-hexane) to afford the corresponding carbamate (22 or 27a–k).

(2-Styrylpyridin-3-yl)carbamic acid 2-bis(2-trimethylsilylethyl)phosphonooxy-benzyl ester (22a). Following the above procedure, the crude carbamate obtained from 2-Bis(2-trimethylsilylethyl)phosphonooxybenzyl alcohol (21 a) (29.72 g, 0.073 mol) was directly used for the further reaction without purification.

(2-Styrylpyridin-3-yl)carbamic acid 2-bis(2-trimethylsilylethyl)phosphonooxy-5-chlorobenzyl ester (22)

Following the above procedure, 21 (9.4 g, 21 mmol) gave 22 (10.6 g, 58%) as an oil:
$^1$H NMR (300 MHz, CDCl$_3$) δ8.23 (d, 1H), 7.92 (br s, 1H), 7.56 (d, 1H), 7.4–7.0 (m, 11H), 5.11 (s, 2H), 4.10 (m, 4H), 0.94 (m, 4H) and −0.14 (s, 18H).
$^{13}$C NMR (75 MHz, CDCl$_3$) δ153.7, 151.9, 147.3 (d), 146.8, 145.2, 136.5, 134.8, 131.4, 130.2, 129.5, 129.3, 129.2, 128.5, 128.3, 127.2, 122.3, 121.3, 121.2, 67.4 (d), 61.6, 19.4 (d) and −1.7.
$^{31}$P NMR (121 MHz, CDCl$_3$) δ5.1.
Mass Calcd. For $C_{31}H_{42}ClN_2O_6PSi_2$: 661.277; Found: 661.2

(2-Styrylpyridin-3-yl)carbamic acid 2-bis(2-trimethylsilylethyl)phosphonooxy-5-fluorobenzyl ester (27a)

Following the above procedure, the crude carbamate 27a obtained from 26a (31.0 g, 73 mmol) was directly used for the further reaction without purification.

(2-Styrylpyridin-3-yl)carbamic acid 2-bis(2-trimethylsilylethyl)phosphonooxy-5-nitrobenzyl ester (27b).

Following the above procedure, 26b (4.3 g, 9.6 mmol) gave 27b (2.3 g, 35%) as an oil:
$^1$H NMR (300 MHz, CDCl$_3$) δ8.3–7.0 (m, 14H), 5.21 (s, 2H), 4.16 (m, 4H), 0.99 (m, 4H) and −0.12 (m, 18H).
$^{13}$C NMR (75 MHz, CDCl$_3$) δ153.5, 153.2 (d), 149.9, 145.6, 144.3, 136.4, 135.1, 131.1, 129.3, 129.0 (d), 128.5, 128.4, 127.2, 124.9, 124.8, 122.4, 120.9, 120.3, 68.0 (d), 62.1, 19.5 (d), 17.1 and −1.6.
$^{31}$P NMR (121 MHz, CDCl$_3$) δ4.5.

(2-Styrylpyridin-3-yl)carbamic acid 2-bis(2-trimethylsilylethyl)phosphonooxy-5-methoxybenzyl ester (27c)

Following the above procedure, the cruse carbamate 27c obtained from 26c (6.0 g, 26 mmol) was directly used for the further reaction without purification.

(2-Styrylpyridin-3-yl)carbamic acid 2-bis(2-trimethylsilylethyl)phosphonooxy-5-trifluoromethoxybenzyl ester (27d)

Following the above procedure, 26d (1.9 g, 8.5 mmol) gave 27d (3.4 g, 83%) as an oil:
$^1$H NMR (300 MHz, CDCl$_3$) δ8.39 (dd, 1H), 8.13 (br s, 1H), 7.74 (d, 1H), 7.60 (m, 2H), 7.60 (m, 2H), 7.4 1 (dd, 1H), 7.4–7.1 (m, 7H), 5.30 (s, 2H), 4.27 (m, 4H), 1,10 (m, 4H) and 0.0 (s, 18H).
$^{13}$C NMR (75 MHz, CDCl$_3$) δ153.4, 147.3 (d), 145.7, 145.4, 136.6, 135.4, 131.2, 129.8, 129.7, 129.2 (d), 128.6, 128.5, 127.4, 127.0, 125.2, 122.7, 122.5, 122.2, 121.5, 120.8, 120.0 (d), 118.6, 67.6 (d), 62.0, 19.6 (d) and –1.6.
$^{31}$P NMR (121 MHz, CDCl$_3$) δ5.3.
$^{19}$F NMR (282 MHz, CDCl$_3$) δ–58.7.

(2-Styrylpyridin-3-yl)carbamic acid 2-bis(2-trimethylsilylethyl)phosphonooxy-5-trifluoromethylbenzyl ester (27e)

Following the above procedure, 26e (5.1 g, 11 mmol) gave 27e (5.3 g, 71%) as an oil:
$^1$H NMR (300 MHz, CDCl$_3$) 67 8.40 (dd, 1 H), 8.14 (br s, 1H), 7.74 (d, 2H), 7.6–7.5 (m, 4H), 7.4–7.1 (m, 8H), 5.29 (s, 2H), 4.29 (m, 4H), 1.11 (m, 4H) and 0.0 (s, 18H).
$^{13}$C NMR (75 MHz, CDCl$_3$) δ153.4, 145.4 (m), 136.5, 135.4, 131.1, 129.7, 128.6, 128.5, 128.2, 128.1, 127.4, 127.1 (d), 122.5, 120.8, 120.5, 120.0 (d), 67.7 (d), 61.9, 19.6 (d) and –1.6.
$^{31}$P NMR (121 MHz, CDCl$_3$) δ5.0.
$^{19}$F NMR (282 MHz, CDCl$_3$) δ–62.7.

(2-Styrylpyridin-3-yl)carbamic acid 2-bis(2-trimethylsilylethyl)phosphonooxy-3,5-dichlorobenzyl ester (27f)

Following the above procedure, 26f (6.3 g, 13 mmol) gave 27f (7.1 g, 76%) as an oil:
$^1$H NMR (300 MHz, CDCl$_3$) δ8.39 (dd, 1H), 8.11 (br s, 1H), 7.74 (d, 1H), 7.59 (br d, 2H), 7.4–7.2 (m, 8H), 7.18 (dd, 2H), 5.35 (s, 2H), 4.29 (m, 4H), 1.11 (m, 4H) and 0.0 (s, 18H).
$^{13}$C NMR (75 MHz, CDCl$_3$) δ153.3, 145.4 (d), 136.5, 135.4, 131.9 (d), 131.1, 131.0, 130.2, 129.8, 129.7, 128.7, 128.6, 128.3, 128.0 (d), 127.4, 122.5, 120.8, 67.9 (d), 62.2, 19.5 (d) and –1.6.
$^{31}$P NMR (121 MHz, CDCl$_3$) δ5.0.

(2-Styrylpyridin-3-yl)carbamic acid 2-bis(2-trimethylsilylethyl)phosphonooxy4,5-dichlorobenzyl ester (27g).

Following the above procedure, 26g (11.3 g, 50 mmol) gave 27g (17.4 g, 75%) as an oil:
$^1$H NMR (300 MHz, CDCl$_3$) δ8.38 (dd, 1H), 8.12 (br s, 1H), 7.74 (d, 1H), 7.60 (dd, 2H), 7.53 (s, 1H), 7.51 (d, 1H), 7.4–7.2 (m, 6H), 7.17 (dd, 2H), 5.23 (s, 2H), 4.27 (m, 4H), 1.10 (m, 4H) and 0.0 (s, 18H).
$^{13}$C NMR (75 MHz, CDCl$_3$) δ153.4, 147.7 (d), 145.4, 136.6, 135.4, 133.1, 131.3, 131.2, 128.9, 128.6, 128.5, 127.7 (d), 127.4, 122.5, 120.8, 67.8 (d), 61.5, 19.6 (d) and –1.6.
$^{31}$P NMR (121 MHz, CDCl$_3$) δ5.2.

(2-Styrylpyridin-3-yl)carbamic acid 2-bis(2-trimethylsilylethyl)phosphonooxy-5,6-dichlorobenzyl ester (27h).

Following the above procedure, 26h (6.2 g, 28 mmol) gave 27h (9.6 g, 75%) as an oil:
$^1$H NMR (300 MHz, CDCl$_3$) δ8.38 (dd, 1H), 8.20 (br s, 1H), 7.73 (d, 1H), 7.60 (br d, 2H), 7.48 (d, 1H), 7.4–7.2 (m, 7H), 7.18 (dd, 2H), 5.48 (s, 2H), 4.28 (m, 4H), 1.10 (m, 4H), and 0.0 (s, 18H).
$^{13}$C NMR (75 MHz, CDCl$_3$) δ153.4, 149.2 (d), 145.2, 136.5, 135.4, 134.7, 131.3, 131.0, 129.8, 129.4, 128.6, 128.5, 127.4, 127.3 (d), 122.5, 120.7, 119.6 (d), 67.7 (d), 59.9, 19.6 (d) and –1.6.
$^{31}$P NMR (121 MHz, CDCl$_3$) δ5.0.

(2-Styrylpyridin-3-yl)carbamic acid 2-bis(2-trimethylsilylethyl)phosphonooxy-3-methylbenzyl ester (27i)

Following the above procedure, 26i (1.4 g, 6.2 mmol) gave 27i (1.5 g, 53%) as an orange oil:
$^1$H NMR (300 MHz, CDCl$_3$) δ8.23 (dd, 1H), 7.97 (br s, 1H), 7.66 (m, 1H), 7.58 (d, 1H), 7.4–6.9 (m, 10H), 5.27 (s, 2H), 4.11 (m, 4H), 2.27 (s, 3H), 0.94 (m, 4H) and –0.11 (s, 18H).
$^{13}$C NMR (75 MHz, CDCl$_3$) δ153.9, 147.6 (d), 146.4, 145.1, 136.6, 134.7, 131.7, 131.6, 131.0, 130.8 (d), 128.5, 128.4 (d), 128.3, 127.6, 127.3, 125.3, 122.3, 121.2, 67.1 (d), 62.9, 19.5 (d), 17.1 and –1.6.
$^{31}$P NMR (121 MHz, CDCl$_3$) δ5.6.
Mass Calcd. For C$_{32}$H$_{45}$N$_2$O$_6$PSi$_2$: 640.859; Found: 640.2

(2-Styrylpyridin-3-yl)carbamic acid 2-bis(2-trimethylsilylethyl)phosphonooxy-4-chlorobenzyl ester (27j)

Following the above procedure, 26j (9.3 g, 21 mmol) gave 27j (12.6 g, 87%) as an oil:
Rf (1:1 v/v ethyl acetate-hexane) 0.82.
$^1$H NMR (300 MHz, CDCl$_3$) δ8.28 (dd, 1H), 8.15 (br s, 1H), 7.72 (d, 1H), 7.60 (d, 2H), 7.4–7.3 (m, 7H), 7.2–7.1 (m, 2H), 5.26 (s, 2H), 4.28 (m, 4H), 1.11 (m, 4H) and 0.0 (s, 18H).
$^{13}$C NMR (75 MHz, CDCl$_3$) δ153.6, 149.7 (d), 145.2, 136.6, 135.3, 135.1, 131.4, 131.3, 128.6, 128.5, 127.4, 125.9 (d), 125.4, 122.4, 120.9 (d), 120.8, 67.6 (d), 62.1, 19.5 (d) and –1.6.
$^{31}$P NMR (121 MHz, CDCl$_3$) δ5.1.

(2-Styrylpyridin-3 -yl)carbamic acid 2-bis(2-trimethylsilylethyl)phosphonooxy-4-methoxybenzyl ester (27k).

Following the above procedure, 26k (2.8 g, 6.5 mmol) gave 27k (3.7 g, 86%) as an oil:
Rf (1:1 v/v ethyl acetate-hexane) 0.50.
$^1$H NMR (300 MHz, CDCl$_3$) δ8.36 (dd, 1H), 8.18 (br s, 1H), 7.72 (d, 1H), 7.4–7.3 (m, 6H), 7.62 (d, 2H), 7.2–7.1 (m, 1H), 6.97 (m, 1H), 6.71 (dd, 1H), 5.24 (s, 2H), 4.29 (m, 4H), 3.80 (s, 3H), 1.11 (m, 4H) and 0.0 (s, 18H).
$^{13}$C NMR (75 MHz, CDCl$_3$) δ160.5, 153.9, 150.0 (d), 145.0, 136.7, 135.1, 131.9, 131.6, 130.0, 128.6, 128.4, 127.4, 122.4, 120.9, 119.2 (d), 110.4, 67.3 (d), 62.4, 55.5, 19.6 (d) and –1.6.
$^{31}$P NMR (121 MHz, CDCl$_3$) δ5.2.

(2-formylpyridin-3-yl)carbamic acid 2-(TMSE-phosphonooxy)benzyl esters (23, 28a–k) (ozonolysis)

General Procedure. The corresponding 2-styrylpyridine (22 or 27a–k, 10 mmol) was dissolved in dichloromethane (50 mL) and ethanol (40 mL). The light yellow solution was ozonized at –50° C. till the solution turned to light blue. Nitrogen gas was bubbled through the solution for 30 min to expel excess ozone. To the solution was then added dimethyl sulfide (5 mL), and the mixture was stirred for 2 h at room temperature. The solvent was evaporated under reduced pressure, and the residual product was purified by FCC (1:9 v/v ethyl acetate-hexane) to afford the corresponding pyridine-2-carboxaldehyde (23 or 28a–k).

(2-Formylpyridin-3-yl)carbamic acid 2-(trimethylsilylethylphosphonooxy)benzyl ester (23a). Following the above procedure, the crude 22a, prepared above, gave 23a (29.81 g, 73%) as an oil:

$^1$H NMR (300 MHz, CDCl$_3$) δ10.49 (s, 1H), 10.06 (s, 1H), 8.84 (d, J=8.36 Hz, 1H), 8.43 (d, J =5.36 Hz, 1H), 7.49–7.16 (m, 5H), 5.34 (s, 2H), 4.32–4.24 (m, 4H), 1.11 (dd, J=8.59 Hz, 6.57 Hz, 4H) and 0.0 (18H).

$^{13}$C NMR (75 MHz, CDCl$_3$) δ197.0, 153.2, 149.1 (d, J=6.45 Hz), 143.7, 138.5, 136.7, 130.1, 129.8, 128.6 (d, J =6.68 Hz), 126.3, 124.9, 120.0, 67.2 (d, J=5.39 Hz, 2C), 62.5, 19.5 (d, J=6.58 Hz, 2C), −1.6.

$^{31}$P NMR (121 MHz, CDCl$_3$) δ5.2.

(2-Formylpyridin-3-yl)carbamic acid 2-bis(2-trimethylsilylethyl)phosphonooxy-5-chlorobenzyl ester (23).

Following the above procedure, 22 (2.4 g, 3.7 mmol) gave 23 (1.6 g, 72%) as an oil:

$^1$H NMR (300 MHz, CDCl$_3$) δ10.38 (br s, 1H), 9.90 (s, 1H), 8.67 (d, 1H), 8.28 (dd, 1H), 7.4–7.3 (m, 2H), 7.23 (dd, 1H), 7.13 (dd, 1H), 5.14 (s, 2H), 4.12 (m, 4H), 0.97 (m, 4H) and −0.14 (m, 18H).

$^{13}$C NMR (75 MHz, CDCl$_3$) δ197.0, 152.9, 147.3 (d), 143.7, 138.3, 136.7, 130.1, 129.6, 129.5, 128.6, 128.5, 126.2, 121.3, 67.4 (d), 61.6, 19.4 (d) and −1.7.

$^{31}$P NMR (121 MHz, CDCl$_3$) δ5.1.

(2-Formylpyridin-3-yl)carbamic acid 2-bis(2-trimethylsilylethyl)phosphonooxy-5-fluorobenzyl ester (28a)

Following the above procedure, the crude 27a (31.0 g, 73 mmol) gave 28a (26.9 g, 64%) as an oil:

$^1$H NMR (300 MHz, CDCl$_3$) δ10.58 (s, 1H), 10.0 (s, 1H), 8.86 (d, 1H), 8.48 (dd, 1H), 7.52 (m, 1H), 7.4–7.3 (m, 1H), 7.21 (dd, 1H), 7.1–6.9 (m, 1H), 5.30 (s, 2H), 4.4–4.2 (m,4H), 1.2–1.0 (m, 4H) and 0.0 (s, 18H).

$^{13}$C NMR (75 MHz, CDCl$_3$) δ197.1, 159.3 (d), 152.9, 144.5 (dd), 143.7, 143.5, 138.4, 136.8, 121.4 (dd), 116.2 (d), 115.9 (d), 67.3 (d), 61.8, 19.5 (d) and −1.6.

$^{31}$P NMR (121 MHz, CDCl$_3$) δ5.5.

$^{19}$F NMR (282 MHz, CDCl$_3$) δ−59.3.

(2-Formylpyridin-3-yl)carbamic acid 2-bis(2-trimethylsilylethyl)phosphonooxy-5-nitrobenzyl ester (28b)

Following the above procedure, 27b (4.2 g, 9.4 mmol) gave 28b (2.8 g, 50%) as an oil:

$^1$H NMR (300 MHz, CDCl$_3$) δ10.42 (br s, 1H), 9.89 (s, 1H), 8.64 (d, 1H), 8.28 (dd, 1H), 8.21 (d, 1H), 8.05 (dd, 1H), 7.47 (d, 1H), 7.33 (dd, 1H), 5.21 (s, 2H), 4.17 (m, 4H), 0.98 (m,4H) and −0.13 (m, 18H).

$^{13}$C NMR (75 MHz, CDCl$_3$) δ197.0, 153.5 (d), 152.7, 144.3, 143.9, 138.1, 136.8, 128.6, 128.3 (d), 126.2, 125.4, 125.2, 120.3, 67.9 (d), 61.4, 19.5 (d) and −1.7. $^{31}$P NMR (121 MHz, CDCl$_3$) δ4.5.

(2-Formylpyridin-3-yl)carbamic acid 2-bis(2-trimethylsilylethyl)phosphonooxy-5-methoxybenzyl ester (28c)

Following the above procedure, the crude 27c (7.5 g, 17 mmol) gave 28c (9.8 g, 73%) as an oil:

$^1$H NMR (300 MHz, CDCl$_3$) δ10.37 (s, 1H), 9.93 (s, 1H), 8.71 (d, 1H), 8.30 (d, 1H), 7.34 (dd, 1H), 7.19 (d, 1H), 6.85 (d, 1H), 6.70 (d, 1H), 5.18 (s, 2H), 4.2–4.0 (m, 4H), 3.66 (s, 3H), 1.1–0.9 (m, 4H) and 0.0 (s, 18H).

$^{13}$C NMR (75 MHz, CDCl$_3$) δ196.9, 156.4, 153.1, 143.6, 142.4 (d), 138.5, 136.7, 128.6, 127.7(d), 126.2, 120.9, 115.1, 114.3, 67.1 (d), 62.3, 55.5, 19.4(d) and −1.7.

$^1$P NMR (121 MHz, CDCl$_3$) δ5.8.

(2-Formylpyridin-3-yl)carbamic acid 2-bis(2-trimethylsilylethyl)phosphonooxy-5-trifluoromethoxybenzyl ester (28d)

Following the above procedure, 27d (4.7 g, 6.6 mmol) gave 28d (3.2 g, 75%) as an oil:

$^1$H NMR (300 MHz, CDCl$_3$) δ10.54 (br s, 1H), 10.06 (s, 1H), 8.82 (d, 1H), 8.44 (dd, 1H), 7.48 (dd, 1H), 7.44 (dd, 1H), 7.32 (d, 1H), 7.25 (s, 1H), 7.2–7.1 (m, 1H), 5.30 (s, 2H), 4.26 (m, 4H), 1.10 (m, 4H) and 0.0 (s, 18H).

$^{13}$C NMR (75 MHz, CDCl$_3$) δ197.2, 153.0, 147.1 (d), 145.7, 143.9, 138.4, 136.9, 129.8, 128.8, 128.7, 126.4, 122.6, 122.2, 121.3, 120.0, 119.9, 67.6 (d), 61.8, 19.5 (d) and −1.6.

$^{31}$P NMR (121 MHz, CDCl$_3$) δ5.3.

$^{19}$F NMR (282 MHz, CDCl$_3$) δ−58.8.

(2-Formylpyridin-3-yl)carbamic acid 2-bis(2-trimethylsilylethyl)phosphonooxy-5-trifluoromethylbenzyl ester (28e)

Following the above procedure, 27e (12.2 g, 18 mmol) gave 28e (6.9 g, 63%) as an oil:

$^1$H NMR (300 MHz, CDCl$_3$) δ10.54 (br s, 1H), 10.06 (d, 1H), 8.82 (br d, 1H), 8.44 (dd, 1H), 7.72 (br s, 1H), 7.6–7.5 (m, 2H), 7.48 (dd, 1H), 7.3–7.1 (m, 2H), 5.33 (s, 2H), 4.27 (m,4H), 1.10 (m, 4H) and 0.0 (s, 18H).

$^{13}$C NMR (75 MHz, CDCl$_3$) δ197.1, 153.0, 151.5 (d), 143.9, 138.4, 136.9, 129.8, 129.7, 128.7, 127.7, 127.6, 127.3 (d), 127.1, 127.0, 126.4, 126.3, 125.2, 120.3 (d), 120.0 (d), 67.7 (d), 61.8, 19.6 (d) and −1.6.

$^{31}$P NMR (121 MHz, CDCl$_3$) δ4.9.

$^{19}$F NMR (282 MHz, CDCl$_3$) δ−62.7.

(2-Formylpyridin-3-yl)carbamic acid 2-bis(2-trimethylsilylethyl)phosphonooxy-3,5-dichlorobenzyl ester (28f)

Following the above procedure, 27f (8.0 g, 12 mmol) gave 28f (5.1 g, 71%) as an oil:

$^1$H NMR (300 MHz, CDCl$_3$) δ10.54 (br s, 1H), 10.05 (s, 1H), 8.79 (d, 1H), 8.42 (dd, 1H), 7.46 (dd, 1H), 7.35 (dd, 2H), 7.24 (s, 1H), 5.38 (s, 2H), 4.27 (m, 4H), 1.12 (m, 4H) and 0.0 (m, 18H).

$^{13}$C NMR (75 MHz, CDCl$_3$) δ197.2, 152.8, 149.9, 143.9, 143.6 (d), 138.4, 136.8, 131.8 (d), 131.0 (d), 130.1, 128.7, 128.0 (d), 127.8 (d), 126.3, 120.0 (d), 67.8 (d), 62.0, 19.6 (d) and −1.6.

$^{31}$P NMR (121 MHz, CDCl$_3$) δ5.1.

(2-Formylpyridin-3-yl)carbamic acid 2-bis(2-trimethylsilylethyl)phosphonooxy-4,5-dichlorobenzyl ester (28g)

Following the above procedure, 27g (17.4 g, 25 mmol) gave 28g (13.4 g, 86%) as an oil:

$^1$H NMR (300 MHz, CDCl$_3$) δ10.51 (br s, 1H), 10.05 (s, 1H), 8.79 (d, 1H), 8.42 (dd, 1H), 7.53 (dd, 1H), 7.5–7.4 (m, 1H), 7.24 (s, 1H), 6.96 (dd, 1H), 5.23 (s, 2H), 4.28 (m,4H), 1.10 (m, 4H) and 0.0 (m, 18H).

$^{13}$C NMR (75 MHz, CDCl$_3$) δ197.2, 152.9, 147.4 (d), 144.0, 138.3, 136.9, 133.1, 131.0, 128.8 (d), 128.7, 127.2 (d), 126.3, 122.2, 122.0, 67.8 (d), 61.3, 19.6 (d) and −1.6.

$^{31}$P NMR (121 MHz, CDCl$_3$) δ5.1.

(2-Formylpyridin-3-yl)carbamic acid 2-bis(2-trimethylsilylethyl)phosphonooxy-5,6-dichlorobenzyl ester (28h)

Following the above procedure, 27h (9.5 g, 14 mmol) gave 28h (6.5 g, 77%) as an oil: $^1$H NMR (300 MHz, CDCl$_3$) δ10.44 (br s, 1H), 10.05 (s, 1H), 8.86 (d, 1H), 8.44 (dd, 1H), 7.50 (d, 1H), 7.47 (d, 1H), 7.41 (d, 1H), 7.38 (m, 1H), 5.46 (s, 2H), 4.25 (m, 4H), 1.10 (m, 4H) and 0.0 (m, 18H).

$^{13}$C NMR (75 MHz, CDCl$_3$) δ197.0, 153.0, 149.9, 149.2 (d), 143.8, 138.5, 136.8, 135.0, 131.2, 129.8, 129.6, 128.7, 126.6 (d), 126.3, 119.5 (d), 67.7 (d), 59.9, 19.5 (d) and −1.6.

$^1$P NMR (121 MHz, CDCl$_3$) δ4.9.

(2-Formylpyridin-3-yl)carbamic acid 2-bis(2-trimethylsilylethyl)phosphonooxy-3-methylbenzyl ester (28i)

Following the above procedure, 27i (1.5 g, 2.2 mmol) gave 28i (1.1 g, 86%) as an oil:
$^1$H NMR (300MHz, CDCl$_3$)δ10.35 (br s, 1H),9.92 (s, 1H), 8.71 (d, 1H), 8.28(dd, 1H), 7.32 (dd, 1H), 7.16 (d, 1H), 7.05 (d, 1H), 6.96 (dd,1H), 5.31 (s, 2H), 4.12 (m, 4H), 2.28 (s, 3H), 0.97 (m, 4H) and −0.12 (m, 1H).
$^{13}$C NMR(75 MHz, CDCl$_3$)δ196.9, 153.2, 147.2(d), 143.6, 138.6, 131.6, 130.9(d), 128.6, 128.0 (d), 127.4, 126.2, 125.3, 67.1 (d), 62.9, 19.4(d), 17.0 and −1.7.
$^{31}$P NMR (121 MHz, CDCl$_3$) δ5.8.

(2-Formylpyridin-3-yl)carbamic acid 2-bis(2-trimethylsilylethyl)phosphonooxy-4-chlorobenzyl ester (28j)

Following the above procedure, 27j (12.2 g, 19 mmol) gave 28j (8.9 g, 80%) as an oil:
Rf (1:1 v/v ethyl acetate-hexane) 0.66.
$^1$H NMR (300 MHz, CDCl$_3$) δ10.49 (br s, 1H), 10.04 (s, 1H), 8.80 (d, 1H), 8.42 (dd, 1H), 7.5–7.4 (m, 3H), 7.16 (dd, 1H), 5.26 (s, 2H), 4.27 (m, 4H), 1.11 (m, 4H) and 0.0 (s, 18H).
$^{13}$C NMR (75 MHz, CDCl$_3$) δ197.1, 153.1, 149.3 (d), 143.8, 138.5, 136.8, 135.0, 131.0, 128.7, 126.3, 125.3 (d), 125.2, 120.5 (d), 67.5 (d), 61.9, 19.5 (d) and −1.6.
$^{31}$P NMR (121 MHz, CDCl$_3$) δ5.0.

(2-Formylpyridin-3-yl)carbamic acid 2-bis(2-trimethylsilylethyl)phosphonooxy-4-methoxybenzyl ester (28k)

Following the above procedure, 27k (5.1 g, 8.0 mmol) gave 28k (2.7 g, 58%) as an oil:
Rf (1:1 v/v ethyl acetate-hexane) 0.44.
$^1$H NMR (300 MHz, CDCl$_3$) δ10.50 (br s, 1H), 10.05 (s, 1H), 8.84 (d, 1H), 8.42 (dd, 1H), 7.46 (dd, 1H), 7.36 (dd, 1H), 7.01 (s, 1H), 6.71 (dd, 1H), 5.24 (s, 2H), 4.27 (m, 4H), 3.80 (s, 3H), 1.10 (m, 4H) and 0.0 (s, 18H).
$^{13}$C NMR (75 MHz, CDCl$_3$) δ197.0, 160.9, 153.4, 150.2 (d), 143.6, 138.7, 136.7, 131.7, 128.7, 126.3, 118.5 (d), 110.6, 106.1 (d), 67.3 (d), 62.4, 55.5, 19.5 (d) and −1.6.
$^{31}$P NMR (121 MHz, CDCl$_3$) ⌐5.0.

Example 8

Preparation of pyridine-2-carboxaldehyde thiosemicarbazones (24, 29a–k)

General Procedure. The corresponding pyridine-2-formaldehyde (23, 23a or 28a–k, 10 mmol) was dissolved in ethanol-water (2:1 v/v, 150 mL). To the solution was added thiosemicarbazide (11 mmol). The solution was stirred for 30 min at ambient temperature. After addition of water (50 mL), the reaction mixture was stirred vigorously for 2 h at room temperature. The yellow precipitate was collected by filtration, washed with ethanol-water (1:4 v/v) and dried in vacuum to afford the corresponding pyridine-2-carboxaldehyde thiosemicarbazone (24, 24a, 29a–k).

(2-Thiosemicarbazonomethylpyridin-3-yl)carbamic acid 2-bis(2-trimethyl silyl ethyl)phosphonooxy-5-chlorobenzyl ester (24)

Following the above procedure, 23 (6.9 g, 12 mmol) gave 24 (4.9 g, 63%) as a yellow solid:
$^1$H NMR (300 MHz, DMSO-d$_6$) δ11.77 (br s, 1H), 10.03 (br s, 1H), 8.40 (dd, 1H), 8.28 (br s, 1H), 8.26 (s, 1H), 7.94 (br s, 1H), 7.5–7.4 (m, 4H), 5.20 (s, 2H), 4.06 (m, 4H), 0.98 (m,4H) and −0.03 (m, 18H).
$^{13}$C NMR (75 MHz, DMSO-d$_6$) δ178.5, 153.4, 148.0 (d), 144.2, 142.9, 141.0, 133.9, 129.5 (d), 128.9, 128.4, 128.0, 124.4, 121.6, 65.1 (d), 61.2, 18.9 and −1.5.
$^{31}$P NMR (121 MHz, DMSO-d$_6$) δ9.8.

Mass Calcd. For C$_{25}$H$_{39}$ClN$_5$O$_6$PSSi$_2$: 660.267; Found: 660.2

(2-Thiosemicarbazonomethylpyridin-3-yl)carbamic acid 2-bis(2-trimethyl silyl ethyl)phosphonooxy benzyl ester (24a). Following the above procedure, 23a (29.74 g, 0.54 mol) gave 24a (33.67 g, 90%)) as a yellow solid: $^1$H NMR (DMSO-d$_6$, 300 MHz): d 11.76 (s, 1H), 10.04 (s, 1H), 8.38 (d, J=4.32 Hz, 1H ), 8.29 (s, 2H), 7.86–7.26 (m, 5H), 5.27 (s, 2H), 4.26–4.18 (m, 4H), 1.05 (dd, J=9.08 Hz, 7.64 Hz, 4H), 0.0 (s, 18H); $^{13}$C NMR (DMSO-d$_6$, 75 MHz): d 178.9, 153.3, 148.0(d, J=6.42 Hz),144.6, 144.3, 140.6, 133.9, 129.5, 127.2(d, J=5.54 Hz), 125.2, 124.1, 119.8 (d, J=4.32 Hz), 119.6, 66.7 (d, J=7.8 Hz, 2C), 61.3, 18.9 (d, J=6.5 Hz, 2C),−1.6; $^{31}$P NMR(DMSO-d$_6$, 121 MHz): d9.7

(2-Thiosemicarbazonomethylpyridin-3-yl)carbamic acid 2-bis(2-trimethylsilylethyl)phosphonooxy-5-fluorobenzyl ester (29a)

Following the above procedure, 28a (14.3 g, 25 mmol) gave 29a (12.9 g, 80%) as a yellow solid:
$^1$H NMR (300 MHz, DMSO-d$_6$) δ11.85 (s, 1H), 10.13 (s, 1H), 8.45 (d, 1H), 8.26 (s, 1H), 7.5–7.1 (m, 5H), 5.21 (s, 2H), 4.2–4.0 (m, 4H), 1.0–0.9 (m, 4H) and 0.0 (s, 18H).
$^{13}$C NMR(75 MHz, DMSO-d$_6$) δ178.6, 159.8, 156.0, 153.4, 145.1 (d), 143.5, 141.5, 140.4, 134.2, 129.5, 124.5, 121.4 (d), 115.5, 64.4 (d), 61.3, 18.9 (d) and −1.6.
$^{31}$P NMR (121 MHz, DMSO-d$_6$) δ10.5.
$^{19}$F NMR (282 MHz, DMSO-d$_6$) δ62.5.

Mass Calcd. For C$_{25}$H$_{39}$FN$_5$O$_6$PSSi$_2$: 643.813 Found: 644.2

(2-Thiosemicarbazonomethylpyridin-3-yl)carbamic acid 2-bis(2-trimethylsilylethyl)phosphonooxy-5-nitrobenzyl ester (29b)

Following the above procedure, 28b (1.6 g, 2.7 mmol) gave 29b (1.3 g, 77%) as a yellow solid:
$^1$H NMR (300 MHz, DMSO-d$_6$) δ11.86 (br s, 1H), 10.14 (br s, 1H), 8.4–8.2 (m, 4H), 7.87 (br s, 2H), 7.64 (m, 1H), 7.52 (m, 1H), 5.26 (s, 2H), 4.05 (m, 4H), 0.97 (m, 4H) and −0.03 (m, 18H).
$^{13}$C NMR (75 MHz, DMSO-d$_6$) δ178.6, 155.3 (d), 153.4, 143.7, 142.7, 140.7, 134.1, 128.1 (d), 125.2, 124.6, 124.5, 120.1, 64.8 (d), 61.2, 18.9 (d) and −1.5.
$^{31}$P NMR (121 MHz, DMSO-d$_6$) δ9.2.

(2-Thiosemicarbazonomethylpyridin-3-yl)carbamic acid 2-bis(2-trimethylsilylethyl)phosphonooxy-5-methoxybenzyl ester (29c)

Following the above procedure, 28c (5.0 g, 8.8 mmol) gave 29c (4.4 g, 77%) as a yellow solid:
$^1$H NMR (300 MHz, DMSO-d$_6$) δ11.85 (s, 1H), 10.08 (s, 1H), 8.41 (d, 1H), 8.35 (d, 1H), 8.30 (s, 1H), 8.03 (s, 2H), 7.51 (dd, 1H), 7.26 (d, 1H), 7.01 (d, 1H), 6.90 (dd, 1H), 5.26 (s, 2H), 4.2–4.0 (m, 4H), 3.75 (s, 3H), 1.1–0.9 (m, 4H) and 0.0 (s, 18H).
$^{13}$C NMR (75 MHz, DMSO-d$_6$) δ178.7, 155.7, 153.6, 143.9, 142.6 (d), 134.2, 129.4, 128.4 (d), 124.5, 121.1, 114.1, 113.9, 64.9 (d), 61.9, 55.6, 19.1 (d) and −1.4.
$^{31}$P NMR (121 MHz, DMSO-d$_6$) δ10.3.

Mass Calcd. For C$_{26}$H$_{42}$N$_5$O$_7$PSSi$_2$: 655.848 Found: 656.2

(2-Thiosemicarbazonomethylpyridin-3-yl)carbamic acid 2-bis(2-trimethylsilylethyl)phosphonooxy-5-trifluoromethoxybenzyl ester (29d)

Following the above procedure, 28d (2.5 g, 3.9 mmol) gave 29d (1.9 g, 68%) as a yellow solid:
$^1$H NMR (300 MHz, DMSO-d$_6$) δ11.81 (s, 1H), 10.04 (br s, 1H), 8.42 (d, 1H), 8.26 (s, 1H), 7.95 (br s, 1H), 7.5–7.2 (m, 4H), 5.24 (s, 2H), 4.07 (m, 4H), 0.96 (m, 4H) and −0.04 (m, 18H).

$^{13}$C NMR (75 MHz, DMSO-d$_6$) δ178.4, 153.4, 147.8 (d), 144.1, 144.0, 133.9, 129.4 (d), 124.4, 121.9, 121.7, 121.6, 121.4, 118.3, 65.1 (d), 61.2, 18.9 (d) and −1.6.

$^{31}$P NMR (121 MHz, DMSO-d$_6$) δ9.8.

$^{19}$F NMR (282 MHz, DMSO-d$_6$) δ−53.0.

(2-Thiosemicarbazonomethylpyridin-3-yl)carbamic acid 2-bis(2-trimethylsilylethyl)phosphonooxy-5-trifluoromethylbenzyl ester (29e)

Following the above procedure, 28e (5.3 g, 8.5 mmol) gave 29e (3.6 g, 61%) as a yellow solid:

$^1$H NMR (300 MHz, DMSO-d$_6$) δ11.81 (s, 1H), 10.03 (br s, 1H), 8.42 (d, 1H), 8.4–8.3 (m, 2H), 8.26 (s, 1H), 7.89 (br s, 1H), 7.79 (s, 1H), 7.75 (d, 2H), 7.56 (d, 2H), 7.49 (dd, 1H), 5.27 (s, 2H), 4.06 (m, 4H), 0.97 (m, 4H) and −0.04 (m, 18H).

$^{31}$P NMR (121 MHz, DMSO-d$_6$) δ9.5.

$^{19}$F NMR (282 MHz, DMSO-d$_6$) δ56.2.

(2-Thiosemicarbazonomethylpyridin-3-yl)carbamic acid 2-bis(2-trimethylsilylethyl) phosphonooxy-3,5-dichlorobenzyl ester (29f)

Following the above procedure, 28f (4.8 g, 7.7 mmol) gave 29f (4.6 g, 85%) as a yellow solid:

$^1$H NMR (300 MHz, DMSO-d$_6$) δ6 11.75 (s, 1H), 10.04 (s, 1H), 8.39 (d, 1H), 8.30 (d, 1H), 8.26 (s, 1H), 7.91 (br s, 1H), 7.69 (dd, 1H), 7.50 (d, 1H), 7.43 (dd, 1H), 5.29 (s, 2H), 4.24 (m, 4H), 1.03 (m, 4H) and −0.01 (m, 18H).

$^{31}$P NMR (121 MHz, DMSO-d$_6$) δ10.3.

(2-Thiosemicarbazonomethylpyridin-3-yl)carbamic acid 2-bis(2-trimethylsilylethyl) phosphonooxy-4,5-dichlorobenzyl ester (29g)

Following the above procedure, 28g (2.0 g, 3.2 mmol) gave 29g (1.5 g, 70%) as a yellow solid:

$^1$H NMR (300 MHz, DMSO-d$_6$) δ11.85 (s, 1H), 10.08 (s, 1H), 8.42 (d, 1H), 8.31 (d, 1H), 8.26 (s, 1H), 7.89 (m, 1H), 7.70 (s, 1H), 7.59 (s, 1H), 7.5–7.2 (m, 2H), 5.18 (s, 2H), 4.02 (m, 4H), 0.95 (m, 4H) and 0.0 (m, 18H).

$^{13}$C NMR (75 MHz, DMSO-d$_6$) δ178.6, 153.3, 148.8, 143.8, 142.4, 140.6, 134.0, 130.8, 130.2 (d), 129.5, 128.3 (d), 125.8 (d), 124.4, 121.5, 119.9, 64.9 (d), 60.8, 18.9 (d) and −1.5.

$^{31}$P NMR (121 MHz, DMSO-d$_6$) δ9.7.

(2-Thiosemicarbazonomethylpyridin-3-yl)carbamic acid 2-bis(2-trimethylsilylethyl) phosphonooxy-5,6-dichlorobenzyl ester (29h)

Following the above procedure, 28h (5.9 g, 9.5 mmol) gave 29h (3.6 g, 55%) as a yellow solid:

$^1$H NMR (300 MHz, DMSO-d$_6$) δ11.82 (s, 1H), 9.97 (br s, 1H), 8.50 (m, 1H), 8.41 (d, 1H), 8.27 (d, 1H), 8.23 (s, 1H), 7.72 (m, 1H), 7.67 (d, 1H), 7.48 (m, 1H), 7.41 (d, 1H), 7.3–7.1 (m, 1H), 5.32 (s, 2H), 4.03 (m, 4H), 0.96 (m, 4H) and −0.06 (m, 18H).

$^{13}$C NMR (75 MHz, DMSO-d$_6$) δ178.3, 153.3, 150.6 (d), 143.8, 140.8, 134.0, 133.8, 133.3, 131.2, 130.3, 129.4, 126.7 (d), 124.4, 120.1, 119.9 (d), 64.8 (d), 59.4, 18.9 (d) and −1.6.

$^{31}$P NMR (121 MHz, DMSO-d$_6$) δ9.6.

2-Thiosemicarbazonomethylpyridin-3-yl)carbamic acid 2-bis(2-trimethylsilylethyl) hosphonooxy-3-methylbenzyl ester (29i)

Following the above procedure, 28i (1.1 g, 1.9 mmol) gave 29i (0.7 g, 57%) as a yellow solid:

$^1$H NMR (300 MHz, DMSO-d$_6$) δ11.76 (br s, 1H), 9.99 (br s, 1H), 8.42 (br s, 1H), 8.37 (m, 1H), 8.27 (br s, 1H), 8.24 (m, 1H), 8.03 (br s, 1H), 7.45 (dd, 1H), 7.25 (d, 1H), 7.19 (d, 1H), 7.11 (dd, 1H), 5.30 (s, 2H), 4.08 (m, 4H), 2.29 (s, 3H), 1.01 (m, 4H) and −0.03 (m, 18H).

$^{13}$C NMR (75 MHz, DMSO-d$_6$) δ178.7, 153.8, 147.5 (d), 144.4, 143.2, 141.2, 134.3, 131.1, 130.7 (d), 128.9 (d), 126.4, 124.9, 124.6, 65.4 (d), 62.4, 19.2 (d), 16.9 and −1.4.

$^{31}$P NMR (121 MHz, DMSO-d$_6$) δ10.4.

(2-Thiosemicarbazonomethylpyridin-3 -yl)carbamic acid 2-bis(2-trimethylsilylethyl) phosphonooxy-4-chlorobenzyl ester (29j)

Following the above procedure, 28j (10.5 g, 18.5 mmol) gave 29j (11.8 g, 97%) as a yellow solid:

$^1$H NMR (300 MHz, DMSO-d$_6$) δ11.74 (s, 1H), 10.05 (br s, 1H), 8.4–8.3 (m, 3H), 7.85 (br s, 1H), 7.56 (d, 1H), 7.5–7.4 (m, 3H), 5.21 (s, 2H), 4.22 (m, 4H), 1.04 (m, 4H) and −0.01 (s, 18H).

$^{13}$C NMR (75 MHz, DMSO-d$_6$) δ153.2, 148.5, 148.4, 144.8, 144.5, 133.8, 133.0, 130.8, 126.5, 126.4, 125.4, 124.1, 119.7, 67.2 (d), 60.8, 18.9 (d) and −1.6.

$^{31}$P NMR (121 MHz, DMSO-d$_6$) δ9.5.

(2-Thiosemicarbazonomethylpyridin-3-yl)carbamic acid 2-bis(2-trimethylsilylethyl) phosphonooxy-4-methoxybenzyl ester (29k)

Following the above procedure, 28k (2.6 g, 4.5 mmol) gave 29k (2.7 g, 91%) as a yellow solid:

$^1$H NMR (300 MHz, DMSO-d$_6$) δ11.74 (d, 1H), 9.98 (br s, 1H), 8.4–8.3 (m, 3H), 7.82 (br s, 1H), 7.44 (m, 1H), 6.87 (m, 3H), 5.16 (s, 2H), 4.19 (m, 4H), 3.77 (s, 3H), 1.03 (m, 4H) and −0.01 (s, 18H).

$^{13}$C NMR (75 MHz, DMSO-d$_6$) δ178.4, 160.0, 153.2, 150.2, 148.4, 144.8, 144.5, 133.8, 133.0, 130.8, 124.1, 119.0, 110.4, 106.0, 66.8 (d), 61.4, 55.3, 18.9 (d) and −1.6.

$^{31}$P NMR (121 MHz, DMSO-d$_6$) δ9.6.

Example 9

Preparation of free phosphonic acids (6–17)

General Procedure. To a solution of the corresponding TMSE-protected phosphate (24, 24a or 29a–k, 10 mmol) in dichloromethane (300–500 mL) was added trifluoroacetic acid (TFA, 20–50 mL) at 0° C. The reaction mixture was stirred vigorously for 2 h in an ice bath. A precipitate was collected by filtration, washed with cold dichloromethane, and then dried in vacuum. More commonly, the solvents were evaporated, and the resulting residual mixture was then dried in vacuum. The corresponding free phosphonic acid (6–17 and 6a not shown) was obtained as a yellow solid or glassy solid.

Example 10

Preparation of disodium salt of phosphonic acid (25, 30a–k)

General Procedure. The corresponding free phosphonic acid (6–17, 10 mmol) was neutralized with an aqueous saturated sodium bicarbonate (NaHCO$_3$) solution (50–100 mL). The suspension was stirred for 2 h at ambient temperature, and then added a minimum amount of water to make homogenous. The aqueous solution was purified by reversed phase column chromatography with de-ionized water. The fractions were monitored by $^{31}$P NMR and combined. After lyophylization, the corresponding disodium salt (25 or 30a–k) was obtained as a pale yellow powder.

(2-Thiosemicarbazonomethylpyridin-3-yl)carbamic acid 2-(disodium phosphonooxy)-5-chlorobenzyl ester (25)

Following the above procedure, 24 (1.1 g, 1.7 mmol) gave 25 (0.4 g, 49%) as a pale yellow powder:

$^1$H NMR (300 MHz, D$_2$O) δ7.94 (br s, 2H), 7.72 (s, 1H), 7.2–7.0 (m, 3H) and 4.98 (s, 2H).

$^{13}$C NMR (75 MHz, D$_2$O) δ179.6, 157.0, 153.2, 147.2 (d), 145.2, 136.8, 131.4, 130.5, 128.8, 127.8, 123.6 and 65.4.

$^{31}$P NMR (121 MHz, D$_2$O) δ14.3.

(2-Thiosemicarbazonomethylpyridin-3-yl)carbamic acid 2-(disodium phosphonooxy)-5-fluorobenzyl ester (30a)

Following the above procedure, 29a (10.5 g, 16 mmol) gave 7 (6.2 g, 86%), which upon treatment with NaHCO$_3$ gave 30a (4.0 g, 59%) as a pale yellow powder:

$^1$H NMR (300 MHz, D$_2$O) δ8.2 (br s, 1H), 7.8 (br m, 1H), 7.57 (br s, 1H), 7.15 (m, 1H), 6.93 (m, 1H), 6.81 (m, 1H), 6.78 (m, 1H) and 4.93 (s, 2H).

$^{13}$C NMR (75 MHz, D$_2$O) δ179.4, 161.5, 158.4, 156.5, 150.3, 147.3, 146.5, 136.7, 130.8, 130.4, 127.7, 123.5, 117.5, 117.2 and 65.2.

$^{31}$P NMR (121 MHz, D$_2$O) δ14.5.

$^{19}$F NMR (282 MHz, D$_2$O) δ−57.4.

(2-Thiosemicarbazonomethylpyridin-3-yl)carbamic acid 2-(disodium phosphonooxy)-5-nitrobenzyl ester (30b)

Following the above procedure, 29b (2.1 g, 3.0 mmol) gave 30b (1.0 g, 73%) as a dark yellow powder:

$^1$H NMR (300 MHz, D$_2$O) δ8.0–7.8 (m, 4H), 7.40 (m, 1H), 7.17 (m, 1H) and 5.06 (s, 2H).

$^{31}$P NMR (121 MHz, D$_2$O) δ13.8.

(2-Thiosemicarbazonomethylpyridin-3-yl)carbamic acid 2-(disodium phosphonooxy)-5-methoxybenzyl ester (30c)

Following the above procedure, 29c (4.3 g, 16 mmol) gave 9 (2.9 g, 98%), which upon treatment with NaHCO$_3$ gave 30c (1.6 g, 43%) as a pale yellow powder:

$^1$H NMR (300 MHz, D$_2$O) δ7.96 (br s, 1H), 7.70 (br s, 1H), 7.21 (br s, 1H), 7.08 (br s, 1H), 6.73 (s, 2H), 5.05 (s, 2H) and 3.65 (s, 3H).

$^{13}$C NMR (75 MHz, D$_2$O) δ174.5, 151.8, 151.1, 143.4, 142.1, 141.7, 135.9, 131.6, 126.4, 124.9, 122.6, 118.4, 111.7, 60.8 and 53.2.

$^{31}$P NMR (121 MHz, D$_2$O) δ14.6.

(2-Thiosemicarbazonomethylpyridin-3-yl)carbamic acid 2-(disodium phosphonooxy)-5-trifluoromethoxybenzyl ester (30d)

Following the above procedure, 29d (1.9 g, 2.6 mmol) gave 30d (0.5 g, 31%) as a pale yellow powder:

$^1$H NMR (300 MHz, D$_2$O) δ7.93 (br s, 1H), 7.86 (br d, 1H), 7.71 (s, 1H), 7.25 (d, 1H), 7.02 (m, 4H) and 5.01 (s, 2H).

$^{13}$C NMR (75 MHz, D$_2$O) δ179.5, 173.5, 157.1, 153.3, 147.1, 146.8, 145.5, 141.2 (m), 136.5, 132.4 (m), 130.2 (d), 127.7 (d), 124.5, 124.0, 123.1, 122.6, 121.0 and 65.4.

$^{31}$P NMR (121 MHz, D$_2$O) δ14.3.

$^{19}$F NMR (282 MHz, D$_2$O) δ−56.3.

(2-Thiosemicarbazonomethylpyridin-3-yl)carbamic acid 2-(disodium phosphonooxy)-5-trifluoromethylbenzyl ester (30e)

Following the above procedure, 29e (3.6 g, 5.2 mmol) gave 30e (1.3 g, 45%) as a pale yellow powder:

$^1$H NMR (300 MHz, D$_2$O) δ7.98 (br s, 1H), 7.89 (d, 1H), 7.77 (s, 1H), 7.4–7.3 (m, 3H), 7.08 (m, 1H) and 5.04 (s, 2H).

$^{31}$P NMR (121 MHz, D$_2$O) δ14.0.

$^{19}$F NMR (282 MHz, D$_2$O) δ−59.4.

(2-Thiosemicarbazonomethylpyridin-3-yl)carbamic acid 2-(disodium phosphonooxy)-3,5-dichlorobenzyl ester (30f).

Following the above procedure, 29f (4.5 g, 6.5 mmol) gave 30f (0.8 g, 24%) as a pale yellow powder:

$^1$H NMR (300 MHz, D$_2$O) δ8.31 (br s, 1H), 7.88 (br d, 2H), 7.6–7.5 (m, 2H), 7.2–6.8 (m, 5H) and 5.07 (s, 2H).

$^{13}$C NMR (75 MHz, D$_2$O) δ179.6, 156.6 (d), 149.4 (d), 147.4, 146.8 (d), 136.6, 134.2, 131.5, 131.1, 130.7(d), 130.1, 128.5, 127.7(d) and 65.6.

$^{31}$P NMR (121 MHz, D$_2$O) δ14.4.

(2-Thiosemicarbazonomethylpyridin-3-yl)carbamic acid 2-(disodium phosphonooxy)-4,5-dichlorobenzyl ester (30g)

Following the above procedure, 29g (2.5 g, 3.0 mmol) gave 30g (0.4 g, 23%) as a pale yellow powder:

$^1$H NMR (300 MHz, D$_2$O) δ8.07 (s, 1H), 7.99 (m, 1H), 7.85 (s, 1H), 7.39 (s, 1H), 7.19 (m, 2H) and 4.99 (s, 2H).

$^{31}$P NMR (121 MHz, D$_2$O) δ14.3.

(2-Thiosemicarbazonomethylpyridin-3-yl)carbamic acid 2-(disodium phosphonooxy)-5,6-dichlorobenzyl ester (30h)

Following the above procedure, 29h (4.6 g, 6.6 mmol) gave 30h (2.3 g, 64%) as a pale yellow powder:

$^1$H NMR (300 MHz, D$_2$O) δ8.01 (s, 1H), 7.91 (br s, 1H), 7.73 (s, 1H), 7.23 (dd, 2H), 7.12 (m, 1H) and 5.18 (s, 2H).

$^{31}$P NMR (121 MHz, D$_2$O) δ14.2.

(2-Thiosemicarbazonomethylpyridin-3-yl)carbamic acid 2-(disodium phosphonooxy)-3-methylbenzyl ester (30i)

Following the above procedure, 29i (1.2 g, 1.8 mmol) gave 30i (0.5 g, 57%) as a yellow powder:

$^1$H NMR (300 MHz, D$_2$O) δ8.11 (br s, 2H), 7.91 (m, 2H), 7.71 (m, 1H), 7.00 (m, 2H), 6.84 (m, 1H), 5.22 (s, 2H) and 2.14 (s, 3H).

$^{13}$C NMR (75 MHz, D$_2$O) δ146.1, 134.6, 133.6, 131.1, 128.8, 127.9, 125.7, 66.6 and 19.1.

$^{31}$P NMR (121 MHz, D$_2$O) δ14.2.

(2-Thiosemicarbazonomethylpyridin-3-yl)carbamic acid 2-(disodium phosphonooxy)-4-chlorobenzyl ester (30j)

Following the above procedure, 29j (4.2 g, 6.6 mmol) gave 30j (1.6 g, 48%) as a pale yellow powder:

$^1$H NMR (300 MHz, D$_2$O) δ7.98 (s, 1H), 7.90 (m, 1H), 7.74 (s, 1H), 7.31 (s, 1H), 7.09 (m, 3H), 6.85 (m, 1H) and 5.00 (s, 2H).

$^{13}$C NMR (75 MHz, D$_2$O) δ180.0, 157.7,155.9, 147.6, 147.4, 142.3, 137.1, 136.8, 133.2, 132.9, 128.3, 127.9, 124.9 and 65.9.

$^{31}$P NMR (121 MHz, D$_2$O) δ14.3.

(2-Thiosemicarbazonomethylpyridin-3-yl)carbamic acid 2-(disodium phosphonooxy)-4-methoxybenzyl ester (30k)

Following the above procedure, 29k (2.9 g, 4.4 mmol) gave 30k (1.2 g, 54%) as a pale yellow powder:

$^1$H NMR (300 MHz, D$_2$O) δ8.06 (s, 1H), 7.94 (s, 1H), 7.64 (s, 1H), 7.13 (m, 1H), 7.0–6.8 (m, 3H), 6.43 (m, 1H), 4.06 (s, 2H) and 3.58 (s, 3H).

$^{13}$C NMR (75 MHz, D$_2$O) δ161.5, 161.3, 155.1, 133.1, 127.3, 127.0, 111.4, 108.3 and 57.9.

$^{31}$P NMR (121 MHz, D$_2$O) δ14.3.

Biological Testing/Data

Bioconversion of prodrugs to 3-AP catalyzed by alkaline phosphatase. The bioactivation of dimethyl para-prodrug and a subset of the ortho phosphate prodrugs was studied using 4.65×10$^{-5}$ unit of phosphatase enzyme solution (Type VII-SA, from Bovine Intestinal Mucose, Sigma). Upon incubation with phosphatase, all the prodrugs were converted cleanly to the parent drug 3-AP. Under these experimental conditions, there was no significant increase in the half-life (T$_{1/2}$) of bioactivation of ortho phosphate prodrugs compared to that of unsubstituted ortho prodrug (Table 1, below). Human serum stability studies were conducted by incubating the prodrugs at 37° C. in human serum. This study showed that 4-chloro phosphate prodrug 16 is the slowest releasing prodrug which has a half life of 1.5 times that of ortho-prodrug.

TABLE 1

Enzymatic Bioconversion and Serum Stability of 3-AP Phosphate Prodrugs
Half-life

| Prodrugs | Alkaline phosphatase 37° C. | Human Serum 37° C. | Buffered Saline pH 7.6, 37° C. |
|---|---|---|---|
| Ortho- (2) | 16.3 min | 2.7 hr | No hydrolysis |
| Para- (3) | 9.2 min | 1.2 hr | 5.5 hr |
| 5-Cl- (6) | 30.5 min | 3.4 hr | 162 hr |

TABLE 1-continued

Enzymatic Bioconversion and Serum Stability of
3-AP Phosphate Prodrugs
Half-life

| Prodrugs | Alkaline phosphatase 37° C. | Human Serum 37° C. | Buffered Saline pH 7.6, 37° C. |
|---|---|---|---|
| 5-F- (7) | Not Tested | 3.8 hr | No hydrolysis |
| 5-CH$_3$O (9) | 22.1 min | 3.2 hr | 151 hr |
| 4-Cl- (16) | 29.9 min | 4.0 hr | No hydrolysis |
| 4-CH$_3$O (17) | Not Tested | 13.3 hr | 15.7 hr |

In Vivo PK Studies of Ortho Phosphate Bearing 3-AP Prodrugs

The pharmacokinetics of 3-AP prodrugs were characterized following administration of a single intravenous dose of 7.2–8.5 mg/kg of 3-AP phosphate prodrugs (equivalent to 3 mg/kg of 3-AP) to a beagle dog. The animal was dosed once with each prodrug weekly. After each dose, a washout period of at least 6 days was maintained before the next dose was administered. Concentrations of 3-AP (Triapine) and prodrug in serum were determined by HPLC and used to calculate various PK parameters. These PK parameters were compared to those of 3-AP from equimolar doses from a separate study. Mean serum drug concentration versus time data were analyzed by both compartmental and non-compartmental models. AUC, total body clearance (Cl), steady-state volume of distribution (Vd,ss), terminal half-life (T1/2), Cmax, Tmax were calculated for both 3-AP and the prodrugs.

Pharmacokinetic parameters of the prodrugs at equimolar i.v. doses are presented in Table 2 below. Ortho-phosphate prodrug was shown previously to undergo rapid bioconversion to 3-AP when incubated in vitro with alkaline phosphatase. In vivo, the conversion was considerably retarded suggesting that in vivo the off-rate of the drug from the alkaline phosphatase is retarded. At no time have we been able to detect the presence of the intermediary phenol which is the expected cleavage product. The serum half-lives of several of the ortho prodrugs were extended relative to the half life of 3-AP itself in the dog (~1.5 hrs) which is comparable to that seen in humans for Triapine™ (3-AP). The 4-chloro (16), 5-methoxy (9) and 5-fluoro (7) analogs were promising in this regard as reflected in their AUCs and half-lives.

TABLE 2

PK Values of Ortho Phosphate Bearing 3-AP Prodrugs in the Dog

| Prodrugs | C$_{max}$ (μg/mL) | AUC (μg.min/L) | T$_{1/2}$ | Cl (mL/min/kg) | Vss (L/kg) |
|---|---|---|---|---|---|
| Ortho- (3) | 125 | 63309 | 5.9 hr | 0.11 | 0.14 |
| 5-Cl- (6) | 136 | 24263 | 2.1 hr | 0.32 | 0.08 |
|  | 139 | 27939 | 2.3 hr | 0.28 | 0.09 |
| 5-F- (7) | 114 | 44829 | 4.5 hr | 0.47 | 0.11 |
| 5-NO$_2$- (8) | 126 | 3396 | 19 min | 2.33 | 0.12 |
| 5-CH$_3$O- (9) | 126 | 51460 | 4.7 hr | 0.15 | 0.12 |
| 5-CF$_3$O- (10) | 144 | 17584 | 1.4 hr | 0.48 | 0.09 |
| 5-CF$_3$- (11) | 156 | 9579 | 43 min | 0.86 | 0.08 |
| 3,5-Di-Cl- (12) | 140 | 6939 | 34 min | 1.2 | 0.08 |
| 4,5-Di-Cl- (13) | 220 | 21499 | 1.1 hr | 0.39 | 0.15 |
| 5,6-Di-Cl- (14) | 202 | 34211 | 2.0 hr | 0.24 | 0.12 |
| 3-CH$_3$- (15) | 147 | 66756 | 5.3 hr | 0.11 | 0.08 |
| 4-Cl- (16) | 120 | 46321 | 4.5 hr | 0.17 | 0.10 |

Pharmacokinetic parameters of 3-AP itself following i.v. administration of equimolar doses of the prodrugs are presented in Table 3, below. The results of the study evidence that the prodrugs ortho (3), 5-fluoro (7), and 4-chloro (16) appeared to provide an extended release of the parent 3-AP, resulting in sustained concentrations of 3-AP in serum compared to the other prodrugs in the study. These compounds also exhibited increased stability in aqueous solution.

TABLE 3

PK Values of 3-AP in the Dog

| Prodrugs | C$_{max}$ (μg/mL) | AUC (μg.min/L) | T$_{max}$ (min) | T$_{1/2}$ (hour) | V/F (L/kg) |
|---|---|---|---|---|---|
| Para- (2) | 1.6 | 74.5 | — | 1.5 | 2.80 |
| Ortho- (3) | 0.6 | 698 | 8.6 | 14.2 | 1.77 |
| 5-Cl- (6) | 2.2 | 456 | 16.7 | 2.2 | 0.42 |
|  | 2.1 | 395 | — | 2.2 | 3.67 |
| 5-F- (7) | 0.5 | 619 | 1.2 | 13.2 | 1.85 |
| 5-NO$_2$- (8) | 1.9 | 84 | — | 0.5 | 4.27 |
| 5-CH$_3$O- (9) | 1.5 | 987 | 7.9 | 7.7 | 0.67 |
| 5-CF$_3$O- (10) | 9.2 | 709 | — | 0.9 | 0.92 |
| 5-CF$_3$- (11) | 3.0 | 280 | — | 1.1 | 2.74 |
| 3,4-Di-Cl- (12) | 2.1 | 163 | — | 0.9 | 3.99 |
| 4,5-Di-Cl- (13) | 2.7 | 392 | — | 1.7 | 3.14 |
| 5,6-Di-Cl- (14) | 3.6 |  | — | 1.6 | 2.32 |
| 3-CH$_3$- (15) | 1.5 | 998 | 7.8 | 7.8 | 5.18 |
| 4-Cl- (16) | 0.8 | 888 | 9.0 | 12.4 | 1.21 |

Initially, both prodrugs were studied at a single dose of 7.5–7.7 mg/kg (equivalent to 3 mg/kg of Triapine). Based on the findings, a rising dose pharmacokinetic and toxicokinetic study was conducted for the 5-fluoro-prodrug at 20, 40, and 80 mg/kg, and the 4-chloro-prodrug at 20, and 30 mg/kg.

PK parameters of Triapine and the two prodrugs are presented in Tables 4 and 5 and are compared to those obtained, in a separate study, from administration of 3 mg/kg of Triapine (equivalent to approximately 7.5 mg/kg of prodrugs). When compared to dogs treated with Triapine, dogs receiving the 4-chloro- and 5-fluoro-prodrug (at equimolar doses) showed an increased Triapine exposure (expressed as AUC). The dose escalation study showed that the peak serum concentrations and AUCs of Triapine were linearly related to the dose of the prodrug.

TABLE 4

Comparative Pharmacokinetics of Triapine Phosphate Prodrugs
in Dogs - PK Values of Triapine.

| Prodrugs | Dose (mg/kg) | Cmax (μg/mL) | AUC (mg.min/L) | Tmax (min) | T½ (hour) | V/F (L/kg) |
|---|---|---|---|---|---|---|
| 5-Fluoro- (7) | 7.5 | 0.5 | 619 | 1.2 | 13.2 | 1.85 |
|  | 20 | 6.8 | 490 | — | 0.8 | 2.90 |
|  | 40 | 12.4 | 1153 | — | 1.1 | 3.22 |
|  | 80 | 32.0 | 2713 | — | 1.0 | 2.50 |
| 4-Chloro- (16) | 7.7 | 0.8 | 888 | 9.0 | 12.4 | 1.21 |
|  | 20 | 13.0 | 2592 | — | 2.3 | 1.53 |
|  | 30 | 31.9 | 5905 | — | 2.1 | 0.94 |
| Triapine | 3 | 2.3 | 124 | — | 1.8 | 3.57 |

TABLE 5

Comparative Pharmacokinetics of Triapine Phosphate Prodrugs
in Dogs - PK Values of Prodrug.

| Prodrugs | Dose (mg/kg) | Cmax (μg/mL) | AUC (mg.min/L) | T½ (hour) | Cl (mL/min/kg) | Vss (L/kg) |
|---|---|---|---|---|---|---|
| 5-Fluoro- (7) | 7.5 | 114 | 44829 | 4.5 hr | 0.47 | 0.11 |
|  | 20 | 299.6 | 35877 | 1.4 hr | 0.56 | 0.11 |
|  | 40 | 412.0 | 56679 | 1.6 hr | 0.35 | 0.07 |
|  | 80 | 377.4 | 43863 | 1.3 hr | 0.46 | 0.06 |

TABLE 5-continued

Comparative Pharmacokinetics of Triapine Phosphate Prodrugs in Dogs - PK Values of Prodrug.

| Prodrugs | Dose (mg/kg) | Cmax (μg/mL) | AUC (mg.min/L) | T½ (hour) | Cl (mL/ min/kg) | Vss (L/kg) |
|---|---|---|---|---|---|---|
| 4-Chloro- (16) | 7.7 | 120 | 46321 | 4.5 hr | 0.17 | 0.10 |
|  | 20 | 464 | 63080 | 1.6 hr | 0.32 | 0.07 |
|  | 30 | 556 | 90291 | 1.9 hr | 0.33 | 0.15 |
| Triapine | 3 | 2.3 | 124 | — | 1.8 | 3.57 |

Figure 4:
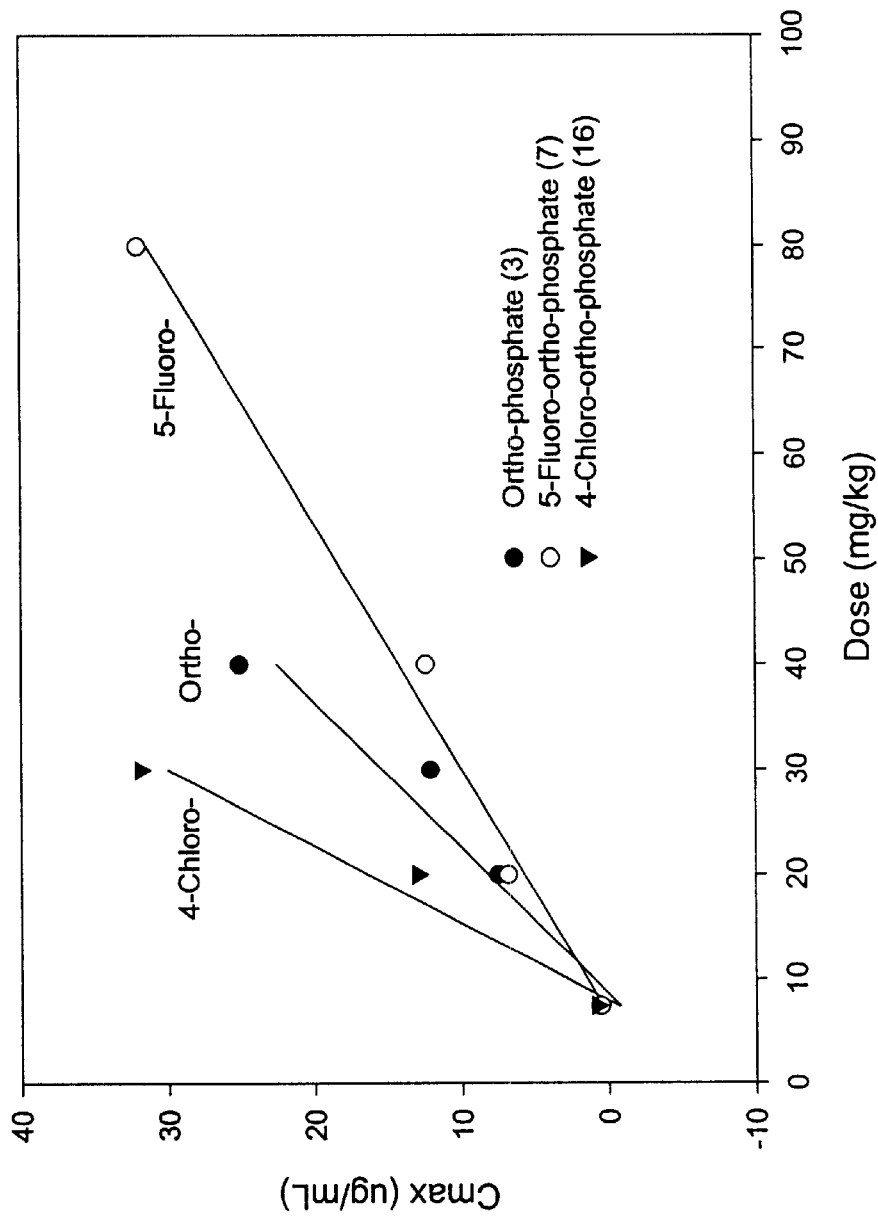
Figure 5:
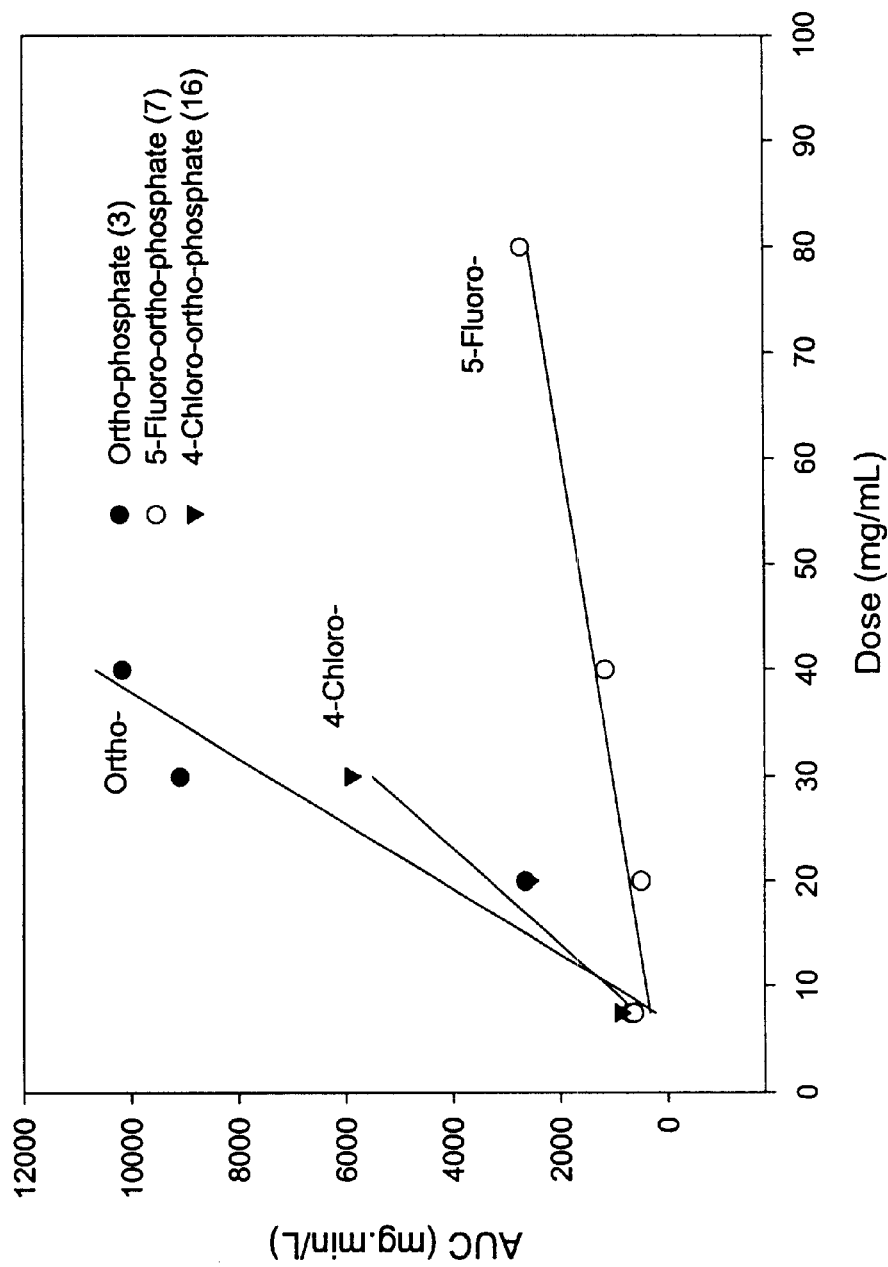
Figure 6:
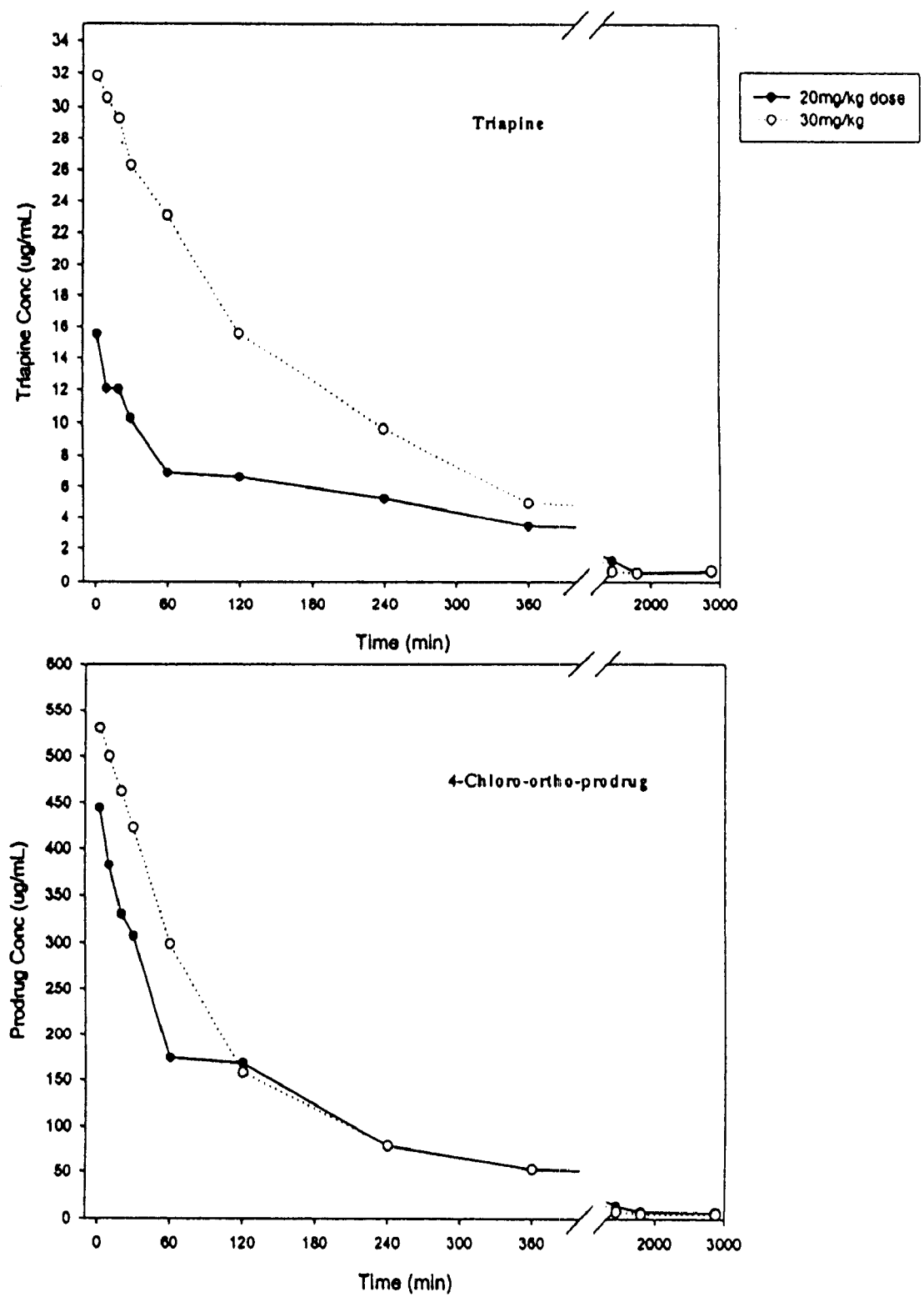
Figure 12:
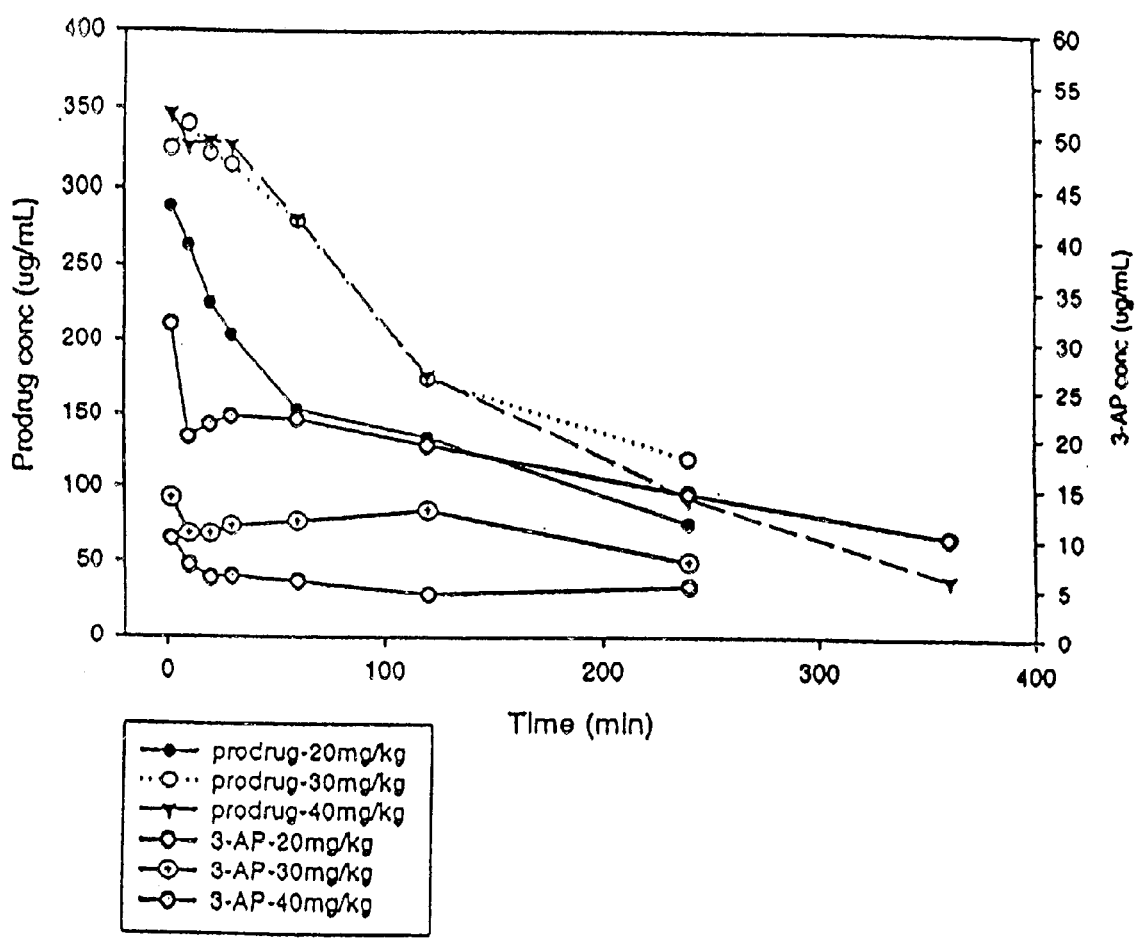

Serum prodrug peak concentrations and AUCs, on the other hand, were not linear with dose, and appeared to be saturated at the doses investigated. Serum concentration-time profiles of prodrugs and Triapine are presented in attached FIGS. 4 and 5. This data suggests that at IV doses ≧20 mg/kg, both prodrugs exhibited an extended bioconversion to parent Triapine, which persisted above 1 μM (0.2 μg/mL) for 24 hours. The sustained serum Triapine levels were presumably attributable to the high serum levels of prodrugs as well as their low total body clearance. The pharmacokinetics of the 4-chloro Prodrug and of the Triapine are shown in FIG. 6. High blood levels of Triapine (<1 μM) were observed at 24 hours at doses that were well tolerated in the dog.

Clinical observations: For dogs which received the 4-chloro-prodrug, there were no early deaths. Treatment-related clinical observations were recorded for both dogs. The male treated at 20 mg/kg exhibited loose stool on days 2 and 3 (day 1=day of dosing). The female treated at 40 mg/kg exhibited emesis, diarrhea, yellow mucous in the stool, reduced activity and was cyanotic (the mouth was grey) on day 1 after dosing. These observations were not present on day 2. The only adverse clinical sign on day 2 was the absence of stool. The male dog treated at 30 mg/kg showed similar clinical sign as the female at 40 mg/kg. The MTD for 4-chloro-prodrug was therefore established at 30–40 mg/kg.

For dogs which received 5-fluoro-prodrug, there were no early deaths. There were no adverse observations from dogs treated at 20 (female), and 40 mg/kg (male). Treatment-related clinical observations were recorded for the female treated at 80 mg/kg. This female exhibited emesis during the infusion and post infusion. In addition, the dog was pale (pallor), diarrhea was noted, and had yellow mucous in the stool. All observations were noted on day 1 and the dog was recovered on day 2. Based on the findings, the MTD for 5-fluoro-prodrug was established at 80 mg/kg.

It should be noted that at MTDs (30 mg/kg for 4-chloro-, and 80 mg/kg for 5-fluoro-prodrug), both prodrugs achieved peak serum levels of Triapine at approximately 32 μg/mL, suggesting the toxicity observed in dogs was due to Triapine, not the prodrug itself.

In Vivo Anti-Tumor Efficacy

Twelve (12) 3-AP prodrugs have been evaluated for efficacy and toxicity using the M109 murine lung carinoma model in Balb/c mice. The procedure of the experiment is as follows: eight week aged female Balb/c mice (about 20 grams) were subcutaneously inoculated with 5×10⁵/mouse of M109 murine lung carinoma cells at the right flank on day 0. The mice were then randomly grouped and each group consisted of 8–10 mice. The treatment was started on day 3 or 5 according to the schedule shown in Table 6, below. 3-AP was used with the Triapine™ formulation while all 3-AP prodrugs were either dissolved or suspended in sterile deionized water. The body weight of mice and the tumor volume were measured twice weekly until the tumor in the control group became necrotic or at least one animal was dead in the control group.

The results are summarized in Table 6, below. Based upon the stability, pharmacokinetics and activity of these agents, it is evident that the 5-fluoro and 4-chloro analogs (7 and 16, respectively) exhibited the greatest activity as anti-cancer agents. In addition, the 5-trifluoromethoxy derivative (10), the 4,5-dichloro derivative (13) and the 5,6-dichloro derivative (14) also evidenced unexpectedly good activity.

TABLE 6

Activity in the M109 Lung Carcinoma Model

| Prodrugs | Dose (mpk,ip) | Schedule (day) | Inhibition (%) | BW Loss (%) | Relative Activity |
|---|---|---|---|---|---|
| 3-AP (1A) | 5.5 (bid) | 3–7, 10–14 | 60 | 8.09 | <CTX |
| Ortho- (3) | 48QD | 5–9, 12–16 | 70 | 12.6 | <CTX |
| 5-Cl- (6) | 60QD | 5–9, 12–16 | 67 | 5.3 | =CTX |
| 5-Fl- (7) | 60QD | 5–9, 12–16 | 75 | 4.7 | =CTX |
| 5-NO₂- (8) | 60QD | 3–7, 10–14, 17–21 | 33 | 9.7 | <<CTX |
| 5-CH₃O- (9) | 48QD | 5–9, 12–16 | 73 | 13.5 | ND |
| 5-CF₃O- (10) | 100QD | 3–7, 10–14, 17–21 | 81 | 8.7 | =CTX |
| 5-CF₃- (11) | 100QD | 3–7, 10–14, 17–21 | 77 | 9.1 | <CTX |
| 3,5-Di-Cl- (12) | 60QD | 3–7, 10–14, 17–21 | 58 | 9.0 | <CTX |
| 4,5-DiCl- (13) | 60 QD | 3–7, 10–14, 17–21 | 57 | 10.0 | <CTX |
| 5,6-Di-Cl- (14) | 60 QD | 3–7, 10–14, 17–21 | 59 | 7.0 | <CTX |
| 3-CH₃- (15) | 60QD | 3–7, 10–14 | 64 | 7.9 | <CTX |
| 4-Cl- (16) | 60QD | 5–9, 12–16 | 74 | 12.6 | =CTX |

CTX=Cytoxan

In general, the prodrugs of 3-AP could be administered at doses as high as 8 times greater than the MTD of 3-AP on amolar basis. These agents could also be given on a QD1-5 schedule weekly for an extended period without excessive mortality in the mice. Treatment with compounds 3, 6, 7, 9, 10 and 16 gave better efficacy on M109 lung carcinoma compared with the 3-AP parent drug at the MTD. Subsequent studies on M109 lung carcinoma were performed using prodrugs 7 and 16 according to the schedule set forth in FIG. 7c and evidenced effective inhibition against M109 lung carcinoma. These agents (prodrugs 7 and 16) were also tested on other cancer cell lines in mice such as HTB Human Lung Carcinoma, B16-F10 Melanoma, DLD-1 Colon Carcinoma, with results evidencing effectiveness significantly greater than cytoxan (see FIGS. 7D, E and F)

5-Chloro (6), 5-Fluoro (7) and 4-Chloro (16), analogs were engaged in further study such as the optimal dose and dosing schedule, different dosing routes, as well as use in combination chemotherapy. The results of these experiments are shown on the appended graphs (see attached as FIGS. 4–10). The results which may be readily obtained from the figures evidence that the prodrugs of the present invention combine well with the DNA damaging agents cytoxan and mitomycin C (FIGS. 8A–D and 9A–C). Similar results, evidence that the present compounds also may be combined to great effect with Etoposide (FIG. 9D) and cisplatin against human colon carcinoma and human lovo colon carcinoma (FIGS. 10A and B).

Efficacy of 3-AP prodrugs on M109 Lung Carcinoma in Balb/c Mice

Materials: M109 lung carinoma cells; BALB/c mice (female, 9 weeks, 18–20 g); cytoxan (Sigma); 3-AP prodrug (ortho 3-AP prodrug(3), 5-methoxy 3-AP prodrug (9), 5-chloro 3-AP prodrug (6), 4-chloro 3-AP prodrug (16) and 5-fluoro 3-AP prodrug (7). 110 Balb/c mice were randomly divided into twelve groups:

| | Groups: | Mice |
|---|---|---|
| 1. | Vehicle 0.2 ml Qd (day 5–9; 12–16; 19–23) | 10 |
| 2. | 200 mpk cytoxan I.p. 1/w | 10 |

3-AP Prodrug Preparation: Each 3-AP prodrug stocking solution (10.0 mg/ml) was made by dissolving the prodrug in deionized sterile water before each injection. The following 3-AP prodrug stock solutions were made for each prodrug by further diluting the stocking solution with water.

| Tube | Stocking | Water | Conc. Of prodrug | Volume |
|---|---|---|---|---|
| 1. | 1.8 ml | 1.2 ml | 6.0 mg/ml | 3 ml |
| 2. | 1.65 ml | 1.35 ml | 5.5 mg/ml (Methoxy 3-AP) | 3 ml |
| 3. | 1.44 ml | 1.56 ml | 4.8 mg/ml | 3 ml |

The M109 cells in log phase were removed by trypsinization, washed with PBS, and reconstituted to 2.5× $10^6$ cells/ml PBS. The M109 suspensions were implanted into the animals subcutaneously on day 0 (0.2 ml, 5×$10^5$ cells/mouse) at the right flank. The mice were randomly regrouped as per the above. Drug treatment was started on day 5 according to the above schedule. The mice were maintained in a clean temperature constant laboratory. The bedding was changed at least twice a week. The mice were provided enough food and drinking water. The drinking water was autoclaved before use. The treatment with orthophosphate 3-AP prodrug (3) and 5-methoxy 3-AP prodrug (9) was stopped before the end of the experiment due to the severe toxic reactions or mortality of the mice. The body weight and tumor were measured twice per week until the end of the experiment. The mortality and the appearance of mice were observed daily.

FIGS. 7A, 7B and 7C evidence the efficacy exhibited by 5-fluoro 3-AP prodrug (7)and the 4-chloro 3-AP prodrug (16) relative to 200 mpk cytoxan in comparison to controls. The 3-AP prodrugs evidenced exceptional tumor shrinking efficacy comparable to cytoxan, with no mortality.

3-AP Prodrug/Cytoxan Combination Chemotherapy on M109 Lung Carcinoma in Balb/c Mice Materials: M109 lung carinoma cells; BALB/c mice (female, 9 weeks, 19–21 g); cytoxan (Sigma); mitomycin C; 4-chloro 3-AP prodrug (16) and 5-fluoro 3-AP prodrug (7). 120 Balb/c mice were randomly divided into fifteen groups, each group consisting of 8 mice:

| | Groups: | Mice |
|---|---|---|
| 1. | Vehicle 0.2 ml Qd (day 3–7; 10–14) | 8 |
| 2. | 200 mpk cytoxan I.P. 1/w × 3 (Start on Day 3) | 8 |
| 3. | 3 mpk mitomycin C, I.V. QD (Day 3 & 17) | 8 |
| 4. | 45 mpk 5-chloro 3-AP prodrug I.P./ Qd (day 3–7; 10–14) + 100 mpk cytoxan, I.P. 1/W (Start on day 4) | 8 |
| 5. | 45 mpk 5-chloro 3-AP prodrug I.P./ Qd (day 3–7; 10–14) + 150 mpk cytoxan, I.P. 1/W (Start on day 4) | 8 |
| 6. | 45 mpk 5-chloro 3-AP prodrug I.P./ Qd (day 3–7; 10–14) + 200 mpk cytoxan, I.P. 1/W (Start on day 4) | 8 |
| 7. | 60 mpk 5-chloro 3-AP prodrug I.P./ Qd (day 3–7; 10–14) + 100 mpk cytoxan, I.P. 1/W (Start on day 4) | 8 |
| 8. | 60 mpk 5-chloro 3-AP prodrug I.P./ Qd (day 3–7; 10–14) + 150 mpk Cytoxan, I.P. 1/W (Start on day 4) | 8 |
| 9. | 60 mpk 5-chloro 3-AP prodrug I.P./ Qd (day 3–7; 10–14) + 200 mpk Cytoxan, I.P. 1/W (Start on day 4) | 8 |
| 10. | 45 mpk 5-fluoro 3-AP prodrug I.P./ Qd (day 3–7; 10–14) + 100 mpk cytoxan, I.P. 1/W (Start on day 4) | 8 |
| 11. | 45 mpk 5-fluoro 3-AP prodrug I.P./ Qd (day 3–7; 10–14) + 150 mpk cytoxan, I.P. 1/W (Start on day 4) | 8 |
| 12. | 45 mpk 5-fluoro 3-AP prodrug I.P./ Qd (day 3–7; 10–14) + 200 mpk cytoxan, I.P. 1/W (Start on day 4) | 8 |
| 13. | 60 mpk 5-fluoro 3-AP prodrug I.P./ Qd (day 3–7; 10–14) + 100 mpk cytoxan, I.P. 1/W (Start on day 4) | 8 |
| 14. | 60 mpk 5-fluoro 3-AP prodrug I.P./ Qd (day 3–7; 10–14) + 150 mpk cytoxan, I.P. 1/W (Start on day 4) | 8 |
| 15. | 60 mpk 5-fluoro 3-AP prodrug I.P./ Qd (day 3–7; 10–14) + 200 mpk cytoxan, I.P. 1/W (Start on day 4) | 8 |

3-AP prodrug preparation: Each 3-AP prodrug stocking solution (10.0 mg/ml) was made by dissolving the prodrug in deionized sterile water before each injection. The following 3-AP prodrug stock solutions were made for each prodrug by further diluting the stocking solution with water.

| Tube | Stocking | Water | Conc. Of prodrug | Volume |
|---|---|---|---|---|
| 1. | 1.8 ml | 1.2 ml | 6.0 mg/ml | 3 ml |
| 2. | 1.35 ml | 1.65 ml | 4.5 mg/ml | 3 ml |

The M109 cells in log phase were removed by trypsinization, washed with PBS, and reconstituted to 2.5× $10^6$ cells/ml PBS. The M109 suspensions were implanted into the animals subcutaneously on day 0 (0.2 ml, 5×$10^5$ cells/mouse) at the right flank. The mice were randomly regrouped as per the above. Drug treatment was started on day 3 according to the above schedule. The mice were maintained in a clean temperature constant laboratory. The bedding was changed at least twice a week. The mice were provided enough food and drinking water. The drinking water was autoclaved before use. The body weight and tumors were measured twice per week until the end of the experiment. The mortality and the appearance of mice were observed daily. FIG. 7C depicts another experiment with a comparison to cytoxan and prodrug (3).

FIGS. 7D–F, evidence the activity exhibited by 5-fluoro 3-AP prodrug (7) and 4-chloro prodrug (16) under the indicated conditions against HTB177 Human Lung Carcinoma, B16-F10 Melanoma and DLD-1 Colon Carcinoma, all carried in mice.

FIG. 8A–D evidence the efficacy exhibited by 5-chloro 3-AP prodrug (6) and the 5-fluoro 3-AP prodrug (7) in combination chemotherapy (with cytoxan) relative to 200 mpk cytoxan against M109 Lung Carcinoma sssin comparison to controls. The 3-AP prodrugs in combination with cytoxan evidenced exceptional synergistic tumor shrinking efficacy when compared to cytoxan alone. Note that no mortality was exhibited during this experiment.

5-Fluoro 3-AP Prodrug/Cytoxan or Mitomycin C Based Combination Chemotherapy on M109 Lung Carcinoma in Balb/c Mice Materials: M 109 lung carinoma cells; BALB/c mice (female, 9 weeks, 19–21 g); cytoxan (Sigma); mitomycin C and 5-fluoro ortho-3-AP prodrug (7). 121 Balb/c mice were randomly divided into twelve groups, each group consisting of 10 mice:

| Groups: | Mice |
| --- | --- |
| 1. Vehicle 0.2 ml Qd (day 3–7; 10–14) | 11 |
| 2. 200 mpk cytoxan I.P. 1/w × 3 (Start on Day 3) | 10 |
| 3. 3 mpk mitomycin C, I.V. QD (Day 3 & 13) | 10 |
| 4. 45 mpk 5-fluoro 3-AP prodrug I.P./ Qd (day 3–7; 10–14) + 150 mpk cytoxan, I.P. 1/W (Start on day 4) | 10 |
| 5. 45 mpk 5-fluoro 3-AP prodrug I.P./ Qd (day 3–7; 10–14) + 200 mpk cytoxan, I.P. 1/W (Start on day 4) | 10 |
| 6. 60 mpk 5-fluoro 3-AP prodrug I.P./ Qd (day 3–7; 10–14) + 150 mpk cytoxan, I.P. 1/W (Start on day 4) | 10 |
| 7. 60 mpk 5-fluoro 3-AP prodrug I.P./ Qd (day 3–7; 10–14) + 200 mpk cytoxan, I.P. 1/W (Start on day 4) | 10 |
| 8. 45 mpk 5-fluoro 3-AP prodrug I.P./ Qd (day 3–7; 10–14) + 2 mpk mitomycin C, I.V. QD (Day 3 & 13) | 10 |
| 9. 60 mpk 5-fluoro 3-AP prodrug I.P./ Qd (day 3–7; 10–14) + 2 mpk mitomycin C, I.V. QD (Day 3 & 13) | 10 |
| 10. 120 mpk 5-fluoro 3-AP, S.C. Qd (day 3–7)* | 10 |
| 11. 150 mpk 5-fluoro 3-AP, S.C. Qd (day 3–7; 10–14)** | 10 |
| 12. 200 mpk 5-fluoro 3-AP, S.C. Qd (day 3–6)*** | 10 |

*Only one dosing schedule was given due to mortality of mice;
**Treatment was stopped after two dosing schedules due to the body weight loss
***Treatment was stopped after four days because of mortality of mice.

3-AP Prodrug Preparation: 5-fluoro 3-AP prodrug (7) stocking solution (20.0 mg/ml) was made by dissolving the prodrug in deionized sterile water before each injection. The following 3-AP prodrug stock solutions were made for each prodrug by further diluting the stocking solution with water.

| Tube | Stocking | Water | Conc. of prodrug | Volume |
| --- | --- | --- | --- | --- |
| 1. | 3.0 ml | 0 ml | 20.0 mg/ml | 3 ml |
| 2. | 2.25 ml | 0.75 ml | 15.0 mg/ml | 3 ml |
| 3. | 1.8 ml | 1.2 ml | 12.0 mg/ml | 3 ml |
| 4. | 1.5 ml | 1.5 ml | 10.0 mg/ml | 3 ml |
| 2. | 0.9 ml | 2.1 ml | 6.0 mg/ml | 3 ml |
| 2. | 0.68 ml | 2.32 ml | 4.5 mg/ml | 3 ml |

Liquid nitrogen stored M109 lung and carcinoma cells ($1 \times 10^6$ cels/ml×1 ml) were recovered by rapidly thawing the cells at 37° C. and cultured with 25 ml of DMEM culture medium containing 10% FCS at 37° C., in 5% $CO_2$. After passing two generations, the cells were washed twice with PBS, pH 7.2, trypsinized and subcultured in the flasks containing 50 ml culture medium. Finally, M109 cells in log phase (about 90–95% saturation) were removed by trypsinization, washed with PBS, and reconstituted to $5 \times 10^6$ cells/ml PBS for tumor implantation. The M109 suspensions were implanted into the animals subcutaneously on day 0 (0.2 ml, $5 \times 10^5$ cells/mouse) at the right flank. The mice were randomly regrouped as per the above. Drug treatment was started on day 3 according to the above schedule. The mice were maintained in a clean temperature constant laboratory. The bedding was changed at least twice a week. The mice were provided enough food and drinking water. The drinking water was autoclaved before use. The body weight and tumors were measured twice per week until the end of the experiment. The mortality and the appearance of mice were observed daily.

FIGS. 9A–C evidence the efficacy exhibited by 5-fluoro 3-AP prodrug (7) and 5-chloro 3-AP prodrug (6) in combination chemotherapy with mitomycin C relative to 200 mpk cytoxan and in comparison to controls. These 3-AP prodrugs in combination with cytoxan and mitomycin C evidenced exceptional synergistic tumor shrinking efficacy when compared to cytoxan or mytomycin C alone. In FIG. D, the results of an experiment comparing the efficacy of a combination of 5-chloro 3-AP prodrug (6) with Etoposide compared with Etoposide alone or control are presented. Synergistic activity was evidenced by the drug combination in this experiment against M109 lung carcinoma.

FIGS. 10A and 10B evidence the effect of combination therapy utilizing 4-chloro 3-AP (16) and cisplatin against DLD-1 Human Colon Carcinoma (FIG. 10A) and Human LoVo Colon Carcinoma (FIG. 10B). In both of these experiments, combination therapy evidenced synergistic activity against the tumors tested.

LD 50 of 5-Fluoro 3-AP Prodrug in C57BL/6J Mice

Materials: C57BL/6J Mice (female, 8 weeks); 5-fluoro 3-AP prodrug (7). 55 C57BL/6J mice were randomly divided into 11 groups, each group consisting of 5 mice:

| Groups: | Mice |
| --- | --- |
| 1. Vehicle 0.2 ml Sterilized deionized water, I.P. QD | 5 |
| 2. 100 mpk 5-fluoro 3-AP prodrug, I.P. Qd | 5 |
| 3. 125 mpk 5-fluoro 3-AP prodrug, I.P. Qd | 5 |
| 4. 150 mpk 5-fluoro 3-AP prodrug, I.P. Qd | 5 |
| 5. 175 mpk 5-fluoro 3-AP prodrug, I.P. Qd | 5 |
| 6. 200 mpk 5-fluoro 3-AP prodrug, I.P. Qd | 5 |
| 7. 175 mpk 5-fluoro 3-AP prodrug, S.C.. Qd | 5 |
| 8. 200 mpk 5-fluoro 3-AP prodrug, S.C.. Qd | 5 |
| 9. 225 mpk 5-fluoro 3-AP prodrug, S.C.. Qd | 5 |
| 10. 250 mpk 5-fluoro 3-AP prodrug, S.C.. Qd | 5 |
| 11. 300 mpk 5-fluoro 3-AP prodrug, S.C.. Qd | 5 |

3-AP prodrug preparation. 5-fluoro 3-AP prodrug (7) was dissolved into sterile deionized water to make the stock solution (30 mg/ml). The following 3-AP prodrug stock solutions were made for each prodrug by further diluting the stocking solution with water.

| Tube | Stocking | Water | Conc. Of prodrug | Volume |
| --- | --- | --- | --- | --- |
| 1. | 3.0 ml | 0 ml | 30.0 mg/ml | 3 ml |
| 2. | 2.5 ml | 0.5 ml | 25.0 mg/ml | 3 ml |
| 3. | 2.25 ml | 0.75 | 22.5 mg/ml | 3 ml |
| 4. | 2 ml | 1 ml | 20 mg/ml | 3 ml |
| 5. | 1.75 ml | 1.25 ml | 17.5 mg/ml | 3 ml |
| 6. | 1.5 ml | 1.5 ml | 15 mg/ml | 3 ml |
| 7. | 1.25 ml | 1.75 ml | 12.5 mg/ml | 3 ml |
| 8. | 1 ml | 2 ml | 10 mg/ml | 3 ml |

Treatment was started on day 0 following the above schedules. The mortality of the animals was recorded daily. The body weight was measured twice per week and the appearance and behavior of the mice were observed daily. FIG. 11 shows the estimation of the LD 50 of 5-fluoro AP prodrug, which is approximately 160 mpk.

Pharmacokinetic Study

The pharmacokinetics of 3-AP (1A) the orthophosphate prodrug (2), and 5-F orthophosphate prodrug (7, 30a, FIG. 3) were determined in beagle dogs (*Canis familiaris*). The dogs were dosed at 20 mg/kg, 30 mg/kg and 40 mg/kg in the case of 3-AP and the orthophosphate prodrug and at 20 mg/kg, 40 mg/kg and 80 mg/kg for the 5-Fluoro orthophosphate prodrug. The dosing schedule for each compound was based upon the Maximum Tolerated Dose for each prodrug, which was significantly higher for the 5-Fluoro orthophosphate produrg than for either 3-AP or the orthophosphate prodrug (3). (It is noted here that even at doses of 80 mg/kg, the 5-Fluoro orthophosphate was not toxic to the animals, whereas in the case of the 3-AP and the orthophosphate prodrug (3), the drug was toxic at the 30 and 40 mg/kg level.

Drug levels were determined for the animals at the intervals which are indicated in attached FIGS. 12–15. These figures evidence that the orthophosphate prodrug had a significant impact on the bioavailability of 3-AP and that the 5-fluorophosphate prodrug provided a significantly greater bioavailabiity and high concentrations of 3-AP for long duration. The pharmacokinetic data for 3-AP and the orthophosphate prodrug (3) is presented in FIG. 12.

Figure 13:
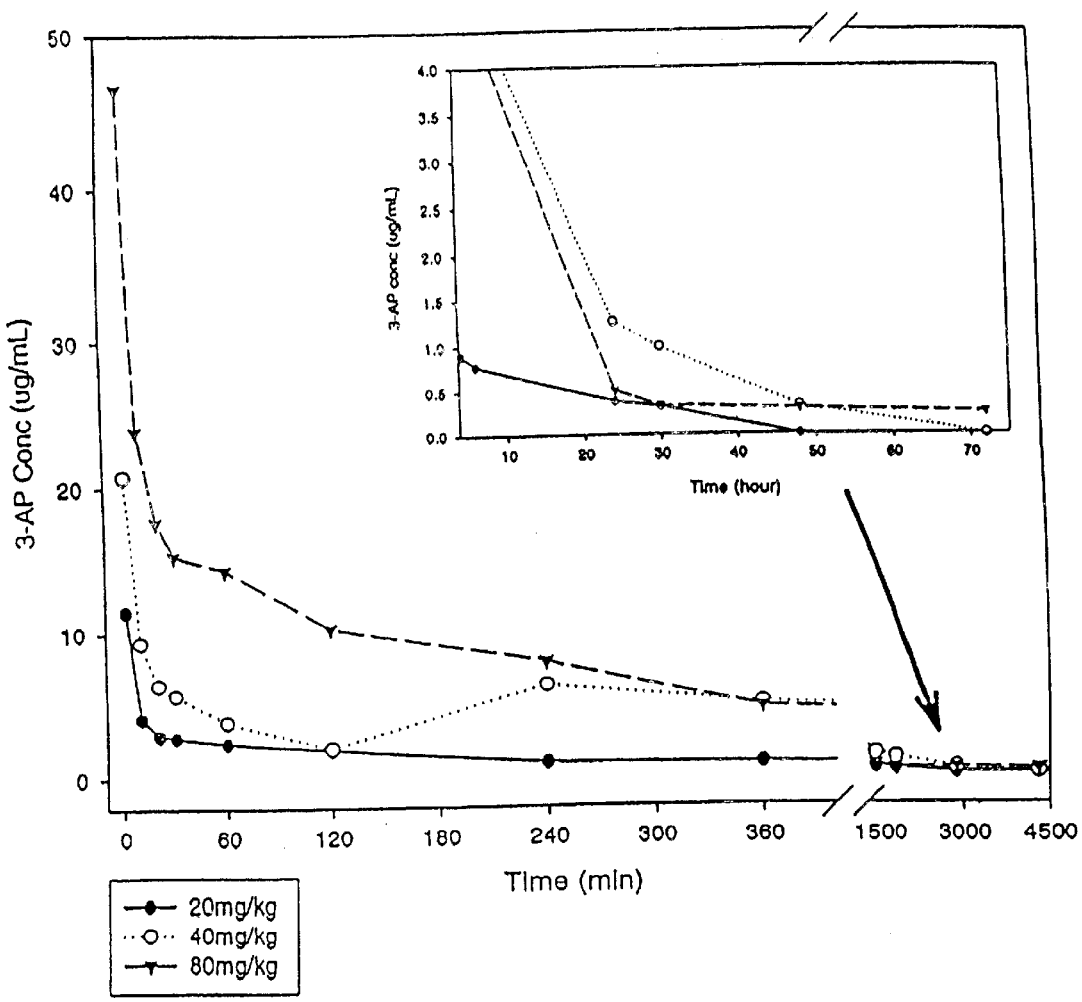
Figure 14:
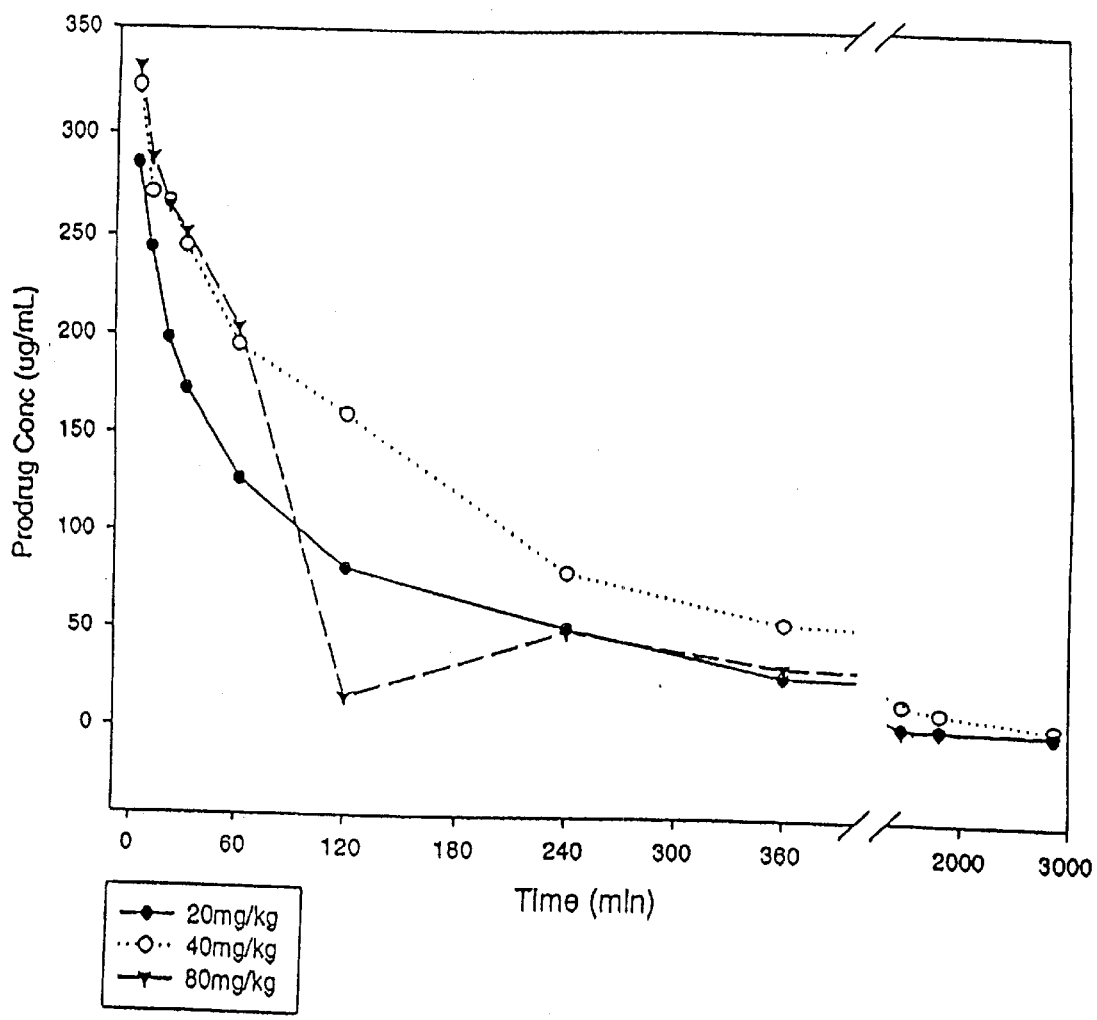
Figure 15:
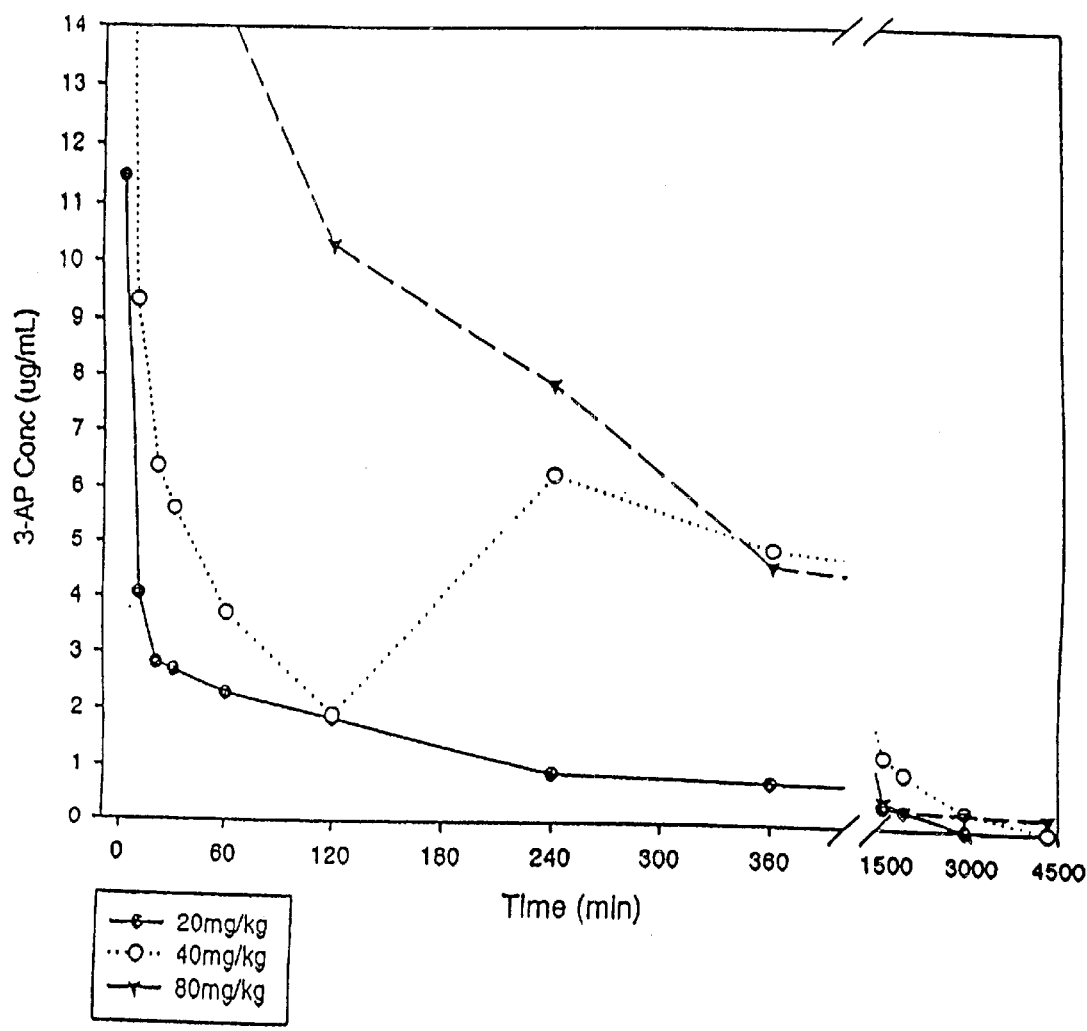

In the case of the 5-fluorophosphate prodrug (7), FIGS. 13–15 set forth the data evidencing that the 5-fluorophosphate derivative provided greater bioavailability of the prodrug compound itself and greater bioavailability of 3-AP resulting from degradation of the prodrug. In addition, the duration of the higher levels of 3-AP was longer in the case of the 5-Fluoro phosphate prodrug (see inset in FIG. 13) tan in the case of 3-AP or the orthophosphate prodrug.

From the studies, it was shown that the 5-fluorophosphate prodrug (7) was tolerated at higher levels (MTD) than either 3-AP or the orthophosphate prodrug (3), and further, provided delivery of 3-AP at higher blood concentrations initially and for a longer duration than either the orthophosphate prodrug form or the 3-AP drug itself.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. A compound according to the structure:

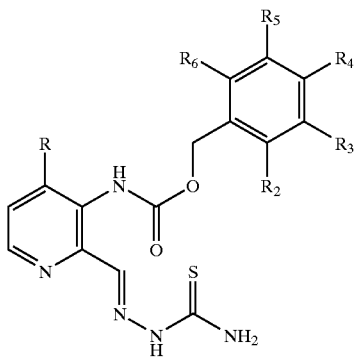

Where
  R is H or CH$_3$;
  R$_2$ is phosphate which can be free acid or salt;
  R$_3$ is H, F, Cl, Br, I, OCH$_3$, OCF$_3$, CF$_3$ or a C$_1$–C$_3$ alkyl group;
  R$_4$ is H, F, Cl, Br, I, OCH$_3$, OCF$_3$ or CF$_3$; and
  R$_5$ and R$_6$ are each independently H, F, Cl, Br, I, OCH$_3$, OCF$_3$ or CF$_3$,
  with the proviso that at least one of R$_3$, R$_4$, R$_5$ or R$_6$ are other than H and when any two of R$_3$, R$_4$, R$_5$ or R$_6$ are other than H, the other two of R$_3$, R$_4$, R$_5$ or R$_6$ are H.

2. The compound according to claim 1 wherein R$_4$ is Cl, F or Br when R$_3$, R$_5$ and R$_6$ are each H.

3. The compound according to claim 2 wherein R$_4$ is Cl.

4. The compound according to claim 1 wherein R$_5$ is F, Cl, OCH$_3$ or OCF$_3$ when R$_3$, R$_4$ and R$_6$ are each H.

5. The compound according to claim 4 wherein R$_5$ is F or Cl.

6. The compound according to claim 5 wherein R$_5$ is F.

7. The compound according to claim 5 wherein R$_5$ is Cl.

8. The compound according to claim 1 wherein two of R$_3$, R$_4$, R$_5$ or R$_6$ are other than H and are selected from F, Cl, Br or I.

9. The compound according to claim 8 wherein two of R$_3$, R$_4$, R$_5$ or R$_6$ are each F or Cl.

10. The compound according to claim 8 wherein R$_4$ and R$_5$ are F or Cl.

11. The compound according to claim 8 wherein or R$_5$ and R$_6$ are F or Cl.

12. The compound according to claim 10 wherein R$_4$ and R$_5$ are Cl.

13. The compound according to claim 11 wherein R$_5$ and R$_6$ are Cl.

14. A pharmaceutical composition comprising an effective amount of a compound for treating neoplasia according to the structure:

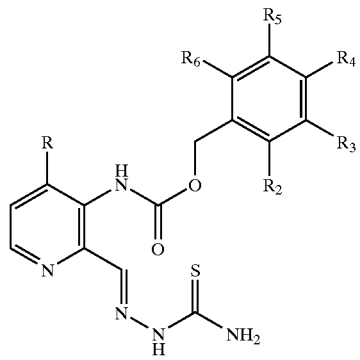

Where
  R is H or CH$_3$;
  R$_2$ is free acid phosphate or phosphate salt;
  R$_3$ is H, F, Cl, Br, I, OCH$_3$, OCF$_3$, CF$_3$ or a C$_1$–C$_3$ alkyl group;
  R$_4$ is H, F, Cl, Br, I, OCH$_3$, OCF$_3$ or CF$_3$; and
  R$_5$ and R$_6$ are each independently H, F, Cl, Br, I, OCH$_3$, OCF$_3$ or CF$_3$,
  with the proviso that at least one of R$_3$, R$_4$, R$_5$ or R$_6$ is other than H and when any two of R$_3$, R$_4$, R$_5$ or R$_6$ are other than H, the other two of R$_3$, R$_4$, R$_5$ or R$_6$ are H, optionally, in combination with a pharmaceutically acceptable additive, carrier or excipient.

15. The composition according to claim 14 wherein R$_4$ is Cl, F or Br when R$_3$, R$_5$ and R$_6$ are each H.

16. The composition according to claim 15 wherein R$_4$ is Cl.

17. The composition according to claim 14 wherein R$_5$ is F, Cl, OCH$_3$ or OCF$_3$ when R$_3$, R$_4$ and R$_6$ are each H.

18. The composition according to claim 17 wherein R$_5$ is F or Cl.

19. The composition according to claim 18 wherein R$_5$ is F.

20. The composition according to claim 18 wherein R$_5$ is Cl.

21. The composition according to claim 14 wherein two of R$_3$, R$_4$, R$_5$ or R$_6$ are other than H and are selected from F, Cl, Br or I.

22. The composition according to claim 21 wherein two of R$_3$, R$_4$, R$_5$ or R$_6$ are each F or Cl.

23. The composition according to claim 21 wherein R$_4$ and R$_5$ are F or Cl.

24. The composition according to claim 21 wherein or R$_5$ and R$_6$ are F or Cl.

25. The composition according to claim 23 wherein $R_4$ and $R_5$ are Cl.

26. The composition according to claim 24 wherein $R_5$ and $R_6$ are Cl.

27. The composition according to claim 14 wherein said neoplasia is cancer.

28. A method of treating neoplasia in a patient in need of therapy comprising administering to said patient an effective amount of a compound according to the structure:

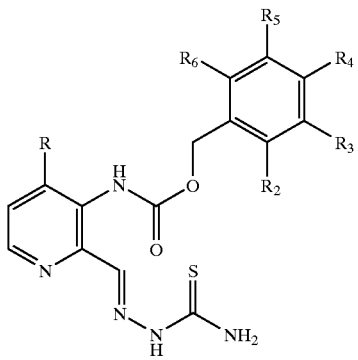

Where

R is H or $CH_3$;

$R_2$ is phosphate which can be free acid or phosphate salt;

$R_3$ is H, F, Cl, Br, I, $OCH_3$, $OCF_3$, $CF_3$ or a $C_1$–$C_3$ alkyl group;

$R_4$ is H, F, Cl, Br, I, $OCH_3$, $OCF_3$ or $CF_3$; and $R_5$ and $R_6$ are each independently H, F, Cl, Br, I, $OCH_3$, $OCF_3$ or $CF_3$, with the proviso that at least one of $R_3$, $R_4$, $R_5$ or $R_6$ is other than H and when any two of $R_3$, $R_4$, $R_5$ or $R_6$ are other than H, the other two of $R_3$, $R_4$, $R_5$ or $R_6$ are H, optionally, in combination with a pharmaceutically acceptable additive, carrier or excipient.

29. The method according to claim 28 wherein $R_4$ is Cl, F or Br when $R_3$, $R_5$ and $R_6$ are each H.

30. The method according to claim 29 wherein $R_4$ is Cl.

31. The method according to claim 28 wherein $R_5$ is F, Cl, $OCH_3$ or $OCF_3$ when $R_3$, $R_4$ and $R_6$ are each H.

32. The method according to claim 31 wherein $R_5$ is F or Cl.

33. The method according to claim 32 wherein $R_5$ is F.

34. The method according to claim 32 wherein $R_5$ is Cl.

35. The method according to claim 28 wherein two of $R_3$, $R_4$, $R_5$ or $R_6$ are other than H and are selected from F, Cl, Br or I.

36. The method according to claim 35 wherein two of $R_3$, $R_4$, $R_5$ or $R_6$ are each F or Cl.

37. The method according to claim 35 wherein $R_4$ and $R_5$ are F or Cl.

38. The method according to claim 35 wherein or $R_5$ and $R_6$ are F or Cl.

39. The method according to claim 37 wherein $R_4$ and $R_5$ are Cl.

40. The method according to claim 38 wherein $R_5$ and $R_6$ are Cl.

41. The method according to claim 28 wherein said neoplasia is cancer.

42. The method according to claim 41 wherein said cancer is stomach cancer, colon cancer, rectal cancer, liver cancer, pancreatic cancer, lung cancer, breast cancer, cervix uteri cancer, corpus uteri cancer, ovary cancer, prostate cancer, testis cancer, bladder cancer, renal cancer, brain/cns cancer, head and neck cancer, throat cancer, Hodgkins disease, non-Hodgkins leukemia, multiple myeloma leukemias, melanoma, acute lymphocytic leukemia, acute mylogenous leukemia, Ewings Sarcoma, small cell lung cancer, choriocarcinoma, rhabdomyosarcoma, Wilms Tumor, neuroblastoma, hairy cell leukemia, mouth/pharynx, oesophagus, larynx, melanoma, kidney or lymphoma.

43. The method according to claim 41 wherein said cancer is lung cancer, breast cancer or prostate cancer.

44. A method of treating neoplasia in a patient in need of therapy comprising administering to said patient in combination an effective amount of a compound according to the structure:

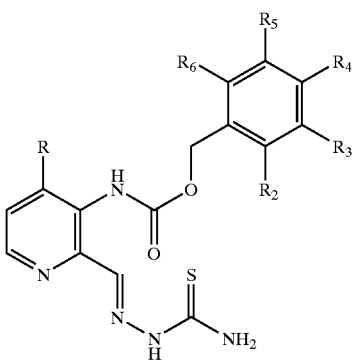

Where

R is H or $CH_3$;

$R_2$ is phosphate which can be free acid or salt;

$R_3$ is H, F, Cl, Br, I, $OCH_3$, $OCF_3$, $CF_3$ or a $C_1$–$C_3$ alkyl group;

$R_4$ is H, F, Cl, Br, I, $OCH_3$, $OCF_3$ or $CF_3$; and $R_5$ and $R_6$ are each independently H, F, Cl, Br, I, $OCH_3$, $OCF_3$ or $CF_3$ with the proviso that when any two of $R_3$, $R_4$, $R_5$ or $R_6$ are other than H, the other two of $R_3$, $R_4$, $R_5$ or $R_6$ are H, optionally, in combination with a pharmaceutically acceptable additive, carrier or excipient and an effective amount of at least one anti-cancer agent which acts to damage DNA.

45. The method according to claim 44 wherein $R_4$ is Cl, F or Br when $R_3$, $R_5$ and $R_6$ are each H.

46. The method according to claim 45 wherein $R_4$ is Cl.

47. The method according to claim 44 wherein $R_5$ is F, Cl, $OCH_3$ or $OCF_3$ when $R_3$, $R_4$ and $R_6$ are each H.

48. The method according to claim 47 wherein $R_5$ is F or Cl.

49. The method according to claim 48 wherein $R_5$ is F.

50. The method according to claim 48 wherein $R_5$ is Cl.

51. The method according to claim 44 wherein two of $R_3$, $R_4$, $R_5$ or $R_6$ are other than H and are selected from F, Cl, Br or I.

52. The method according to claim 51 wherein two of $R_3$, $R_4$, $R_5$ or $R_6$ are each F or Cl.

53. The method according to claim 52 wherein $R_4$ and $R_5$ are Cl.

54. The method according to claim 52 wherein or $R_5$ and $R_6$ are Cl.

55. The method according to claim 44 wherein said neoplasia is cancer.

56. The method according to claim 55 wherein said cancer is stomach cancer, colon cancer, rectal cancer, liver cancer, pancreatic cancer, lung cancer, breast cancer, cervix uteri cancer, corpus uteri cancer, ovary cancer, prostate cancer, testis cancer, bladder cancer, renal cancer, brain/cns cancer, head and neck cancer, throat cancer, Hodgkins disease, non-Hodgkins leukemia, multiple myeloma leukemias, skin melanoma, acute lymphocytic leukemia, acute mylogenous leukemia, Ewings Sarcoma, small cell lung cancer, choriocarcinoma, rhabdomyosarcoma, Wilms Tumor, neuroblastoma, hairy cell leukemia, mouth/pharynx, oesophagus, larynx, melanoma, kidney or lymphoma.

57. The method according to claim 56 wherein said anti-cancer agent is selected from the group consisting of cytoxan, mitomycin C, Etoposide, adriamycin, topotecan, irinotecan, gemcitabine, campothecin, cis-platin, chlorambucil, melphalan and mixtures thereof.

58. The method according to claim 56 wherein $R_3$, $R_4$ and $R_6$ are H, $R_5$ is F or Cl and said anti-cancer agent is cytoxan or mitomycin C.

59. The method according to claim 58 wherein said cancer is lung cancer, prostate cancer, colon cancer, melanoma or breast cancer.

* * * * *